(12) United States Patent
Giedd et al.

(10) Patent No.: US 11,385,196 B2
(45) Date of Patent: Jul. 12, 2022

(54) ENERGETIC PULSE CLEARING OF ENVIRONMENTALLY SENSITIVE THIN-FILM DEVICES

(71) Applicant: Brewer Science Inc., Rolla, MO (US)

(72) Inventors: Ryan E. Giedd, Springfield, MO (US); Jonathan J. Fury, Springfield, MO (US); Erik Harker, Springfield, MO (US); Christopher Landorf, Springfield, MO (US)

(73) Assignee: Brewer Science, Inc., Rolla, MO (US)

(*) Notice: Subject to any disclaimer, the term of this patent is extended or adjusted under 35 U.S.C. 154(b) by 281 days.

(21) Appl. No.: 15/695,557

(22) Filed: Sep. 5, 2017

(65) Prior Publication Data

US 2018/0067066 A1    Mar. 8, 2018

Related U.S. Application Data

(60) Provisional application No. 62/516,491, filed on Jun. 7, 2017, provisional application No. 62/383,553, filed on Sep. 5, 2016.

(51) Int. Cl.
  *G01N 27/14*    (2006.01)
  *G01N 27/12*    (2006.01)
  *G01N 33/00*    (2006.01)

(52) U.S. Cl.
  CPC ........... *G01N 27/14* (2013.01); *G01N 27/124* (2013.01); *G01N 33/0031* (2013.01); *G01N 33/0036* (2013.01)

(58) Field of Classification Search
  None
  See application file for complete search history.

(56) References Cited

U.S. PATENT DOCUMENTS

| | | | |
|---|---|---|---|
| 8,895,997 B2 * | 11/2014 | Maki | H01L 51/0048 257/79 |
| 2004/0161949 A1 * | 8/2004 | Yadav | A61L 27/06 438/800 |

(Continued)

FOREIGN PATENT DOCUMENTS

| | | |
|---|---|---|
| WO | 02/095398 | 11/2002 |
| WO | 2012/168444 | 12/2012 |

OTHER PUBLICATIONS

0. Monereo', et al.; aSelf-heating in pulsed mode for signal quality improvement: Application to carbon nanostructures-based sensors; M[ND-JN7 UB, Department o(EJectronics, University of Barcelonr1, (;'Marti i f'r,-uuluils 1, E-08028 narcelona, Spain; 29 Nuv•ernlie1 2015 (Year: 2015).*

(Continued)

*Primary Examiner* — Nasima Monsur
(74) *Attorney, Agent, or Firm* — Hovey Williams LLP

(57) ABSTRACT

A process and electronic hardware and software system for rapidly heating and cooling an active sensing layer of a gas sensor is provided. A series of high-energy pulses is run through a CNT electrically-active layer, heating the layer to varying temperatures. The influence by various gases on the electrical conductivity of the layer can be used to identify gases (e.g., water vapor, alcohol, methane, $O_2$, $CO_2$, and CO). Advantageously, the same structure can also be used as a nanoheater, either within or outside the context of the gas sensor. The device can acquire a unique gas spectra in seconds, and thus accurately determine gas type and mixtures of gases based on a library of known spectra.

52 Claims, 42 Drawing Sheets

(56) References Cited

U.S. PATENT DOCUMENTS

| | | | | |
|---|---|---|---|---|
| 2004/0202547 | A1* | 10/2004 | Taylor | F24F 8/192 |
| | | | | 417/48 |
| 2005/0193800 | A1 | 9/2005 | DeBoer et al. | |
| 2008/0021339 | A1* | 1/2008 | Gabriel | A61B 5/4821 |
| | | | | 600/532 |
| 2008/0221806 | A1* | 9/2008 | Bryant | G01N 33/497 |
| | | | | 702/22 |
| 2009/0194525 | A1 | 8/2009 | Lee et al. | |
| 2011/0120866 | A1* | 5/2011 | Lee | G01N 27/127 |
| | | | | 204/431 |
| 2011/0263036 | A1* | 10/2011 | Blauw | G01N 27/4146 |
| | | | | 436/149 |
| 2011/0269648 | A1 | 11/2011 | Schwartz | |
| 2015/0200348 | A1* | 7/2015 | Lee | H01L 37/00 |
| | | | | 257/467 |
| 2015/0366005 | A1 | 12/2015 | Janas et al. | |
| 2016/0025517 | A1* | 1/2016 | Giedd | G01K 7/16 |
| | | | | 324/691 |
| 2016/0054258 | A1 | 2/2016 | Nicholas | |

OTHER PUBLICATIONS

Jiang et al., "Joule heating and thermoelectric properties in short single-walled carbon nanotubes: electron-phonon Interaction effect," J. Appl. Phys. 110, 124319 (2011).

Rutherglen et al. "Nanoelectromagnetics: Circuit and Electromagnetic Properties of Carbon Nanotubes," Small 5, No. 8, 884-906 (2009).

Kim et al., "Thermal Behavior of Transparent Film Heaters Made of Single-Walled Carbon Nanotubes," J. Phys. Chem. C 114, 5817-5821 (2010).

Wu et al., "Preparation of large-area double-walled carbon nanotube films and application as film heater," Physica E 42, 77-81 (2009).

Jang et al., "The manufacture of transparent film heater by spinning multi-walled carbon nanotubes," Carbon 49, 111-116(2011).

Sui et al., "Flexible and Transparent Electrothermal Film Heaters Based on Graphene Materials," Small 7, No. 22, 3186-3192 (2011).

Im et al., "Enhancement of Heating Performance of Carbon Nanotube Sheet with Granular Metal," ACS Appl. Mater. Interfaces 4, 2338-2342 (2012).

Liu et al., "Carbon-Nanotube-Film Microheater on a Polyethylene Terephthalate Substrate and Its Application in Thermochromic Displays," Small 7, No. 6, 732-736 (2011).

Mizuno et al., "A black body absorber from vertically aligned single-walled carbon nanotubes," Proc. Natl. Acad. Sci. U.S.A. vol. 106, No. 15, 6044-6047 (Apr. 14, 2009).

Liu et al., "Macroscopic Carbon Nanotube Assemblies: Preparation, Properties, and Potential Applications," Small 7, No. 11, 1504-1520 (2011).

Zhang et al., "High-Density Carbon Nanotube Buckypapers with Superior Transport and Mechanical Properties," Nano Lett. 12, 4848-4852 (2012).

Zhang et al., "Directly measuring of thermal pulse transfer in one-dimensional highly aligned carbon nanotubes," Scientific Reports 3, Article No. 2549, pp. 1-6 (Aug. 30, 2013).

Jiang et al. "Spinning continuous carbon nanotube yarns," Nature 419, 801 (Oct. 24, 2002).

Dalton et al., "Super-tough carbon-nanotube fibres," Nature 423, 703 (Jun. 12, 2003).

Nanot et al., "Broadband, Polarization-Sensitive Photodetector Based on Optically-Thick Films of Macroscopically Long, Dense, and Aligned Carbon Nanotubes," Scientific Reports 3, Article No. 1335, pp. 1-7 (Feb. 27, 2013).

Zhou et al., "Synthesis, Structure, and Properties of Single-Walled Carbon Nanotubes," Adv. Mater. 21, 4565-4583 (2009).

Zhang et al., "Electrical and thermal properties of carbon nanotube bulk materials: Experimental studies for the 328-958 K temperature range," Phys. Rev. B 75, 205407 (2007).

Jakubinek et al., "Thermal and electrical conductivity of array-spun multi-walled carbon nanotube yarns," Carbon 50, 244-248 (2012).

Wang et al., "Highly oriented carbon nanotube papers made of aligned carbon nanotubes," Nanotechnology 19, 075609, pp. 1-6 (2008).

Baughman et al., "Carbon Nanotube Actuators," Science 21, vol. 284, No. 5418, 1340-1344 (May 1999).

Wei et al., "Efficient Fabrication of Carbon Nanotube Micro Tip Arrays by Tailoring Cross-Stacked Carbon Nanotube Sheets," Nano Lett. 12, 2071-2076 (2012).

Yang et al., "Modified carbon nanotube composites with high dielectric constant, low dielectric loss and large energy density," Carbon 47, 1096-1101 (2009).

Kim et al., "Thermal Transport Measurements of Individual Multiwalled Nanotubes," Phys. Rev. Lett. 87, 215502, pp. 1-4 (2001).

Li et al., "Measuring the thermal conductivity of individual carbon nanotubes by the Raman shift method," Nanotechnology 20, 145702, pp. 1-5 (2009).

Pop et al., "Thermal Conductance of an Individual Single-Wall Carbon Nanotube above Room Temperature," Nano Lett. 6, No. 1, 96-100 (2006).

Aliev et al., "Thermal transport in MWCNT sheets and yarns," Carbon 45, 2880-2888 (2007).

Xie et al., "Thermal diffusivity and conductivity of multiwalled carbon nanotube arrays," Phys. Lett. A 369, 120-123 (2007).

Maklin et al., "Thermal diffusivity of aligned multi-walled carbon nanotubes measured by the flash method," Phys. Status Solidi B 248, No. 11, 2508-2511 (2011).

Yi et al., "Linear specific heat of carbon nanotubes," Phys. Rev. B, vol. 59, No. 14, R9015-R9018 (Apr. 1, 1999).

Hou et al., "Thermal characterization of single-wall carbon nanotube bundles using the self-heating 3 omega technique," J. Appl. Phys. 100, 124314 (2006).

Yue et al., "Thermal transport in multiwall carbon nanotube buckypapers," Phys. Lett. A 374, 4144-4151 (2010).

Hou et al., "Thermal characterization of micro/nanoscale conductive and non-conductive wires based on optical heating and electrical thermal sensing," J. Phys. D: Appl. Phys. 39, 3362-3370 (2006).

Hou et al., "Thermal characterization of submicron polyacrylonitrile fibers based on optical heating and electrical thermal sensing," Appl. Phys. Lett. 89, 152504 (2006).

Akoshima et al., "Thermal Diffusivity of Single-Walled Carbon Nanotube Forest Measured by Laser Flash Method," Jpn. J. Appl. Phys. 48, 05EC07 (2009).

Jiang et al., "Superaligned Carbon Nanotube Arrays, Films, and Yarns: A Road to Applications," Adv. Mater. 23, 1154-1161 (2011).

Kosky et al., "Angstrom methods applied to simultaneous measurements of thermal diffusivity and heat transfer coefficients: Part 1, theory," Int. Comm. Heat Mass Transfer, vol. 26, No. 8, 1051-1059 (1999).

Bodzenta et al., "Measurement of the thermal diffusivity of dental filling materials using modified Angstrom's method," Dent. Mater. 22, 617-621 (2006).

Heat Conduction. 3rd Edition. Hahn and Ozisik, John Wiley & Sons, Inc., 2012, Chapter 1, "Heat Conduction Fundamentals," pp. 1-39.

Kato et al., "Anisotropic thermal-diffusivity measurements by a new laser-spot-heating technique," Meas. Sci. Technol. 12, 2074-2080 (2001).

Min et al., "A new laser flash system for measurement of the thermophysical properties," Thermochimica Acta 455, 46-49 (2007).

Prasher R., "Thermal boundary resistance and thermal conductivity of multiwalled carbon nanotubes," Phys. Rev. B 77, 075424 (2008).

Yang et al., "Contact thermal resistance between individual multiwall carbon nanotubes," Appl. Phys. Lett. 96, 023109 (2010).

Zhang et al., "Temperature Dependence of Thermal Boundary Resistances between Multiwalled Carbon Nanotubes and Some Typical Counterpart Materials," ACS Nano, vol. 6, No. 4, 3057-3062 (2012).

Borca-Tasciuc et al., "Anisotropic thermal diffusivity of aligned multiwall carbon nanotube arrays," J. Appl. Phys. 98, 054309 (2005).

(56) References Cited

OTHER PUBLICATIONS

Diao et al., "Selectively enhanced sensing performance for oxidizing gases based on ZnO nanoparticle-loaded electrospun SnO2 nanotube heterostructures", RSC Adv., 2016, 6, 28419-28427.
Soundarrajan et al., "Hydrogen Sensing and Detection", in Hydrogen Fuel: Production, Transport, and Storage, ed. R. B. Gupta, CRC Press, 2009, Chapter 15, pp. 495-534, ISBN 9781420045758.
Wang et al., "Metal Oxide Gas Sensors: Sensitivity and Influencing Factors", Sensors 2010, 10, 2088-2106.
Wang et al., "A Room Temperature H2 Sensor Fabricated Using High Performance Pt-Loaded SnO2 Nanoparticles", Sensors 2015, 15, 14286-14297.
Gu et al., "Hydrogen Gas Sensors Based on Semiconductor Oxide Nanostructures", Sensors 2012, 12, 5517-5550.
Bochenkov et al., "Sensitivity, Selectivity, and Stability of Gas-Sensitive Metal-Oxide Nanostructures", in Metal Oxide Nanostructures and Their Applications, ed. A. Umar, Y. Hahn, American Scientific Publishers, 2010, Chapter 2, vol. 3: pp. 31-52, ISBN: 1-58883-176-0.
Fu et al., "Carbon Nanotubes Based Thin Films: Fabrication, Characterization and Applications", Rev. Adv. Mater. Sci. 36 (2014) 40-61.
Aroutiounian, V.M., "Metal Oxide Gas Sensors Decorated with Carbon Nanotubes", Lithuanian Journal of Physics, vol. 55, No. 4, pp. 319-329 (2015).
Dong et al., "Heme-Enabled Electrical Detection of Carbon Monoxide at Room Temperature Using Networked Carbon Nanotube Field-Effect Transistors", Chemistry of Materials, vol. 19, No. 25, Dec. 11, 2007.
Janas et al., "Improved Performance of Ultra-Fast Carbon Nanotube Film Heaters", Journal of Automation and Control Engineering vol. 2, No. 2, pp. 150-153, Jun. 2014.
Hone et al., "Thermal properties of carbon nanotubes and nanotube-based materials", Appl. Phys. A 74, 339-343 (2002).
Shim et al., "Polymer Functionalization for Air-Stable n-Type Carbon Nanotube Field-Effect Transistors", J. Am. Chem. Soc. 2001, 123, 11512-11513.
Star et al., "Nanoelectronic Carbon Dioxide Sensors", Adv. Mater., Nov. 18, 2004, 16, No. 22, 2049-2052.
Sayago et al., "Novel selective sensors based on carbon nanotube films for hydrogen detection," Sensors and Actuators B 122 (2007) 75-80.
Kaniyoor et al., "Nanostructured Pt decorated graphene and multi walled carbon nanotube based room temperature hydrogen gas sensor," Nanoscale, 2009, 1, 382-386.
Jung et al., "Flexible transparent conductive heater using multiwalled carbon nanotube sheet," Journal of Vacuum Science & Technology B 32(4), Jul./Aug. 2014, 04E105-1-04E105-6.
Kong et al., "Functionalized Carbon Nanotubes for Molecular Hydrogen Sensors," Adv. Mater. 2001, 13, No. 18, Sep. 14, 1384-1386.
International Search Report and Written Opinion dated Dec. 11, 2017 in corresponding PCT/US2017/050086 filed Sep. 5, 2017.
International Preliminary Report on Patentability dated Mar. 14, 2019 in corresponding PCT/US2017/050086 filed Sep. 5, 2017.
Extended European Search Report in corresponding European Patent Application No. 17847684.2, 9 pages.
Monereo et al., "A low-cost approach to low-power gas sensors based on self-heating effects in large arrays of nanostructures," Procedia Engineerig, vol. 120, pp. 787-7900 (2015).
Lu et al., "A carbon-nanotube-based sensor array for formaldehyde detection," Nanotechnology, vol. 22, No. 5, 2011 published Dec. 23, 2010, 4 pages.
Office action dated May 28, 2021 in corresponding Chinese Patent Application No. 201780068237.5, 9 pages.
Office Action dated Jul. 29, 2021 in corresponding European Patent Application No. 17847684.2, 3 pages.
Monereo et al., "Self-heating in pulsed mode for signal quality improvement: Application to carbon nanostructures-based sensors," Sensors and Actuators B: Chemical, 226 (2016) 254-265, 12 pages.
Office Action dated Aug. 17, 2021 in corresponding Korean Patent Application No. 10-2019-7009360, 8 pages.
Translation of Office Action dated Aug. 17, 2021 in corresponding Korean Patent Application No. 10-2019-7009360, 9 pages.

* cited by examiner

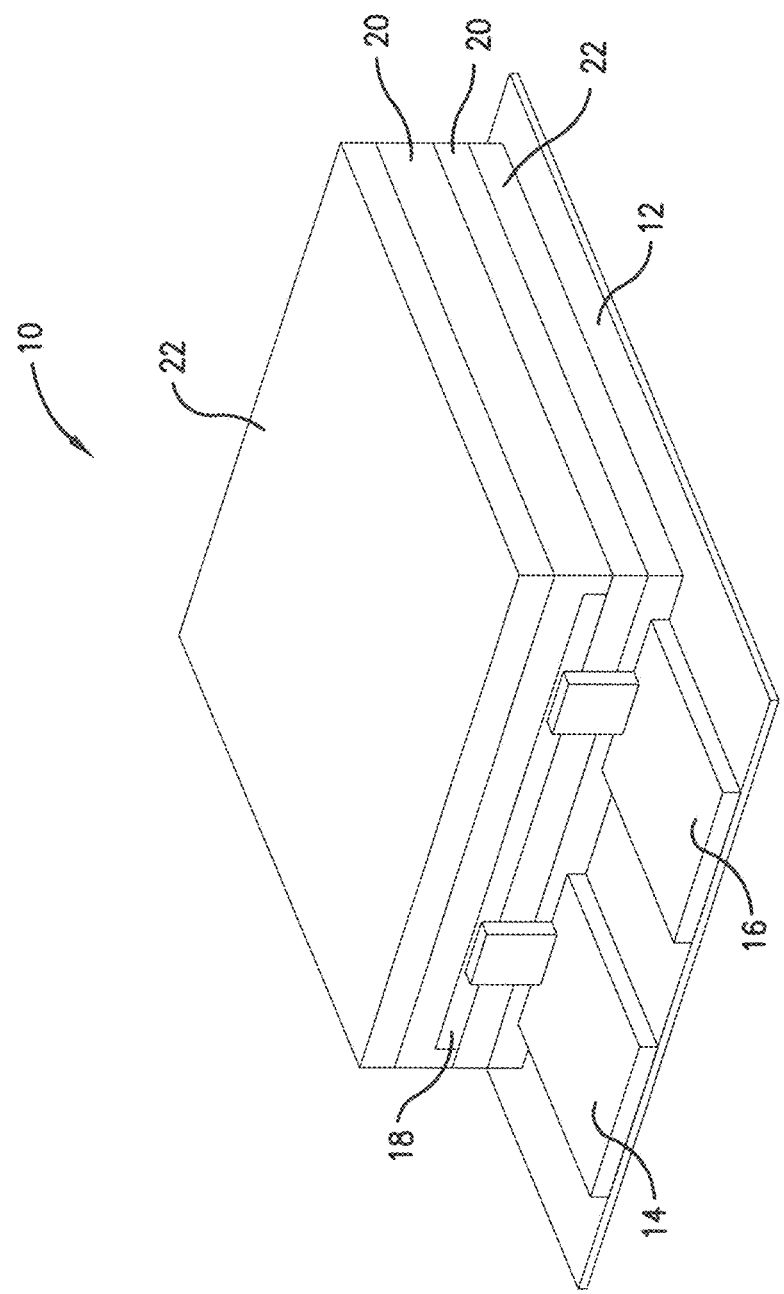

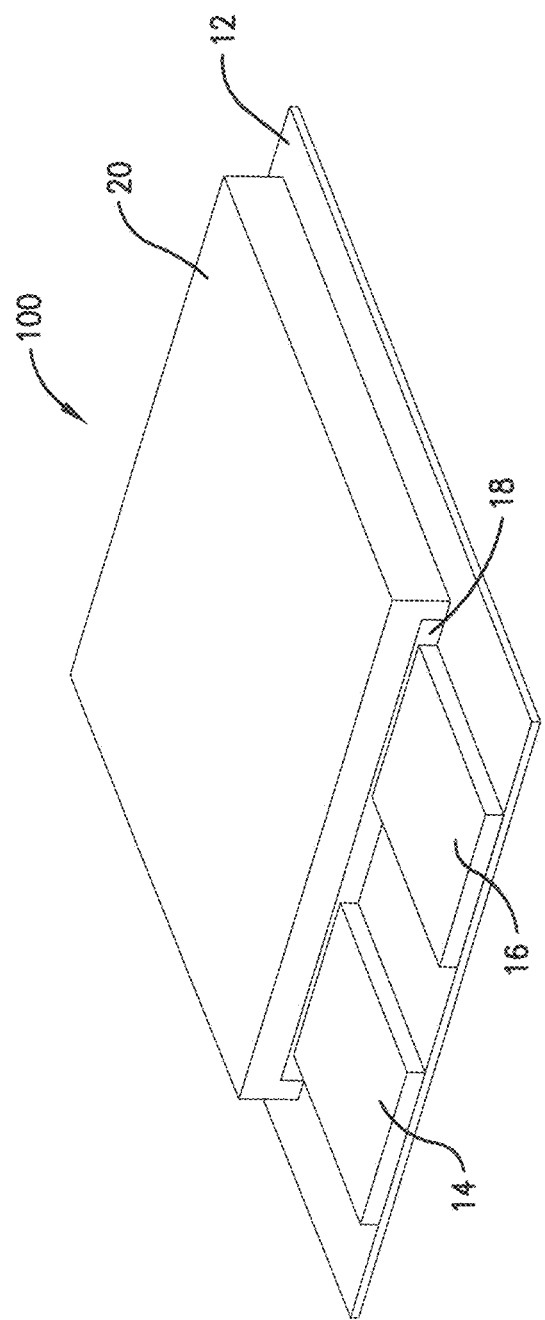

ENERGETIC PULSE CLEARING OF ENVIRONMENTALLY SENSITIVE THIN-FILM DEVICES

RELATED APPLICATION

The current patent application is a non-provisional application which claims priority benefit, with regard to all common subject matter, to U.S. Provisional Application No. 62/516,491, entitled "GAS SENSOR", and filed Jun. 7, 2017 and U.S. Provisional Application No. 62/383,553 entitled "ENERGETIC PULSE CLEARING OF ENVIRONMENTALLY SENSITIVE CNT THIN-FILM DEVICES", and filed Sep. 5, 2016. The earlier-filed provisional applications are hereby incorporated by reference in their entirety into the current application.

BACKGROUND OF THE INVENTION

Field of the Invention

This invention pertains to a method of sensing and clearing environmental signals in thin-film devices.

Description of the Related Art

Certain electronic sensor structures operate by causing a physical change (i.e. electric polarization, magnetic, structural, morphological, or phase changes) or chemical change (i.e. disassociation, reaction, or compositional change) within an "active" layer that results in a corresponding change in device resistance, capacitance, or inductance. In sensors, this could be the result of a change in the sensing material (or "active" layer) of a sensor, caused by a reaction to an external stimulus. Examples of such sensing applications are described in detail in U.S. patent application Ser. No. 14/806,238, filed Jul. 22, 2015, which is incorporated by reference herein.

In many existing CNT sensor technologies, the thin-film electrically active CNT layers generally consist of highly electrically conducting grains (along randomly oriented individual CNTs or ropes made of multiple CNTs) separated by insulating regions. The insulating regions bridge the ends or sidewalls of the CNTs and tend to trap charge carriers on the conducting grains. The process of electrical conduction in these thin film devices (within the active layers) is generally a variable range quantum mechanical hopping or tunneling process of charge transport across the insulating regions from two or more conducting regions. The pathway of carrier transport through this electrical layer is through a very large number of such processes that form a percolation network from electrical contact to electrical contact.

In these devices, it is well known that environmental gases interact with the conduction process through hydrogen or Vander Waals bonding at the interface between the electrical conducting and insulating grains in the thin CNT film. These interactions either tend to increase or decrease the effective carrier trapping potential of the conducting grains. These processes will either raise or lower the electrical conductivity of the CNT layer. Over time, these influences can cause the macroscopic electrical conductivity to drift and generally become unstable as the environment surrounding the films changes. In many cases, this unstable behavior results in poor performance of the device or sensor.

As sensor applications require the diffusion of the environmental constituent in order to operate, it is not possible to simply block the environmental constituent from the active surface. Therefore, for sensor applications, it is necessary to clear the active layer of the device so that there is no environmental constituent in or around the active layer and the electronic behavior of the active layer is stable over time.

For gas sensing, individual, discrete solid-state sensors that can operate in normal atmospheric conditions and can quickly and selectively sense gases, like $H_2$, CO, $CH_4$, $NO_2$, and $H_2O$, are desired by emerging industries for real-time analysis of environmental air. Such solid-state gas detectors could be used in a variety of applications. Many existing sensors are based on metal and/or metal oxide films, nanoclusters, or nanowires that typically detect gases through physisorption or reversible chemical reactions at temperatures from 100°-400° C. These types of devices have been widely utilized in a configuration utilizing a ceramic tube oven heated by a central tungsten or tantalum filament and coated with the gas-sensitive materials. The resistance of the coating is monitored once the oven reaches thermal equilibrium with the surrounding environment, which may take hours. The resistance of the metal film/metal oxide semiconductor fluctuates with the trace gas of interest.

However, the disadvantages of this technology are the lack of gas selectivity and the large power consumption. These devices also may be cross-sensitive to other gases, smoke, and water vapor. As a result, they are best used in a known environment where the gas of interest is generally expected to be present and the cross-sensitive effects are not expected. These devices are signal-enhanced so that they are more sensitive to the gas of interest, but false positive events can result from these cross-sensitivities. Since these devices operate best at temperatures well above room temperature, they tend to expend a significant amount of power, on the order of watts. Thus, additional technologies are being developed for room-temperature operation of these devices, but operation at elevated temperatures will generally enhance the signal. Nevertheless, these solid-state gas sensors have the advantage of having low cost, excellent stability, high sensitivity, and a relatively rapid response once thermal equilibrium is reached.

To increase the gas selectivity (or specificity) of existing solid-state technology, multiple-pixel sensor devices with different individual pixel compositions have been combined on the same heater so that the different absorptions (or other reactions to incoming gas) can be used to better determine unknown gas composition. In this configuration, the pixels are temperature-controlled to the same temperature, and the unknown gas can be identified by the different resistance changes exhibited by each of the pixels as a composite signal. The heater typically heats all pixels to the same temperature, requiring significant power and cannot ramp temperature of the pixels independently or quickly sweep temperature. These different resistance changes of the pixels when exposed to an unknown gas are a result of varying pixel chemical composition. These devices are more gas-selective than individual solid-state gas sensors. These devices are difficult to manufacture so that thermal isolation of the heater can be achieved (sometimes a MEMS device is required) and since each pixel has a slightly different material composition, they require many synthesis steps. Also, the relatively large heater requires a significant time (hours) to come to thermal equilibrium with the background and all pixels must operate at the same temperature. Consequently, these devices have limited selectivity, are difficult to manufacture, and have the same power consumption problems as the single-pixel solid-state devices.

Discrete individual gas-specific electrochemical sensors have also been used to detect gas type and concentration. These devices work on an electrochemical process that requires them to be in a liquid or liquid-containing matrix (such as a hydrogel) so that ions are free to react and diffuse to electrodes. These devices can be made very sensitive and selective. The major disadvantages of these devices are low speed (the time required for the ions to diffuse to electrodes), difficulty of manufacture (many different chemical processes involved in making an array and cannot in general be manufactured in an integrated fashion), short lifetime (the devices have a finite lifetime due to the loss or degradation of the ion-migration matrix), and the possibility of fouling in real-world applications. Nevertheless, this technology is preferred over the solid-state technology in many applications where a single gas-selective sensor is desired, because of the increased selectivity and the lower power consumption when compared to individual solid-state devices. As a result, a number of electrochemical devices would need to be operated in parallel in order to detect a range of different gases.

Other proposed solid-state discrete devices include a class that involves functionalized or "decorated" CNT and graphene gas-sensitive devices. Most of these devices are aimed at operating at room temperature to reduce power consumption compared to solid-state devices. However, these devices must also be temperature controlled to reduce errors associated with varying absorption as a result of fluctuations in environmental temperature.

Most of these devices utilize the properties of the carbon-based nanoparticles in the detection process that is enhanced by the presence of metal or metal oxide materials within the carbon nanoparticle microstructure. These room-temperature sensors are used in conjunction with a separate heater that extends over or under the device. A major problem with cross-sensitivity exists with these devices since they operate at only one temperature.

SUMMARY OF THE INVENTION

In one embodiment, the invention is directed towards an environmental sensor. The sensor comprises first and second electrodes formed from electrically conductive material, with the electrodes being spaced apart from one another and positioned on a substrate. The sensor also comprises an active sensing layer that is positioned on the substrate and in direct contact with at least a portion of each electrode. Additionally, the active sensing layer is configured to experience a change in an electrical characteristic in response to a change in a characteristic of a constituent gas in proximity to the active sensing layer and further configured to receive energy directly from the electrodes to set a temperature of the active sensing layer to a specific value.

In a further embodiment, the invention is concerned with an environmental sensor array. The array comprises a plurality of pixel sensors, with each pixel sensor including first and second electrodes formed from electrically conductive material. The electrodes are spaced apart from one another and positioned on a substrate; and each pixel sensor also includes an active sensing layer positioned on the substrate and in direct contact with at least a portion of each electrode. The active sensing layer of each pixel sensor is configured to experience a change in an electrical characteristic in response to a change in a characteristic of a specific constituent gas in proximity to the active sensing layer. The active sensing layer of each pixel is further configured to receive energy directly from the electrodes to set a temperature of the active sensing layer to a specific value.

The invention also provides a method of determining a constituent gas with an environmental sensor. The method comprises generating a train of electrical pulses that is received by first and second electrodes of an environmental sensor, with the train of electrical pulses being configured to set a temperature of the environmental sensor. A first electrical resistance is measured between first and second electrodes of the environmental sensor during the generation of the train of electrical pulses. The generating and measuring is repeated a plurality of times such that each train of electrical pulses sets the environmental sensor to a different temperature resulting in a first spectrum including a plurality of first resistance measurements, one first resistance measurement for each temperature. The first spectrum is compared to a plurality of response spectra, each response spectrum corresponding to a thermal spectral response of a successive one of a plurality of constituent gases.

The invention further provides a method of determining a constituent gas concentration with an environmental sensor. The method comprises measuring a first electrical resistance between first and second electrodes of an environmental sensor. A train of electrical pulses that is received by the first and second electrodes is generated, with the train of electrical pulses being configured to set a temperature of the environmental sensor. A second electrical resistance between the first and second electrodes is measured after the generation of the train of electrical pulses and the second electrical resistance measurement is subtracted from the first electrical resistance measurement. A value of constituent gas concentration in proximity to the environmental sensor corresponding to the difference between the first resistance measurement and the second resistance measurement is determined.

In yet a further embodiment, a method of heating an environmental sensor comprising first and second electrodes and an active sensing layer contacting the electrodes is provided. The method comprises applying a train of electrical pulses to the first and second electrodes. The train of electrical pulses is applied for a first time period and at a repetition rate, with each electrical pulse having a pulse width time duration and a magnitude value. The first and second electrodes transfer energy to the active sensing layer, which sets the environmental sensor to a temperature.

Finally, the invention is also directed towards a micro-heating method comprising applying an electrical pulse to a heating layer comprising carbon nanotubes, with the electrical pulse having a duration of less than about 100 microseconds.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

Embodiments of the current invention are described in detail below with reference to the attached drawing figures, wherein:

FIG. 1a is an isometric view of a single-pixel gas transducer according to the invention;

FIG. 1b is a plan view of the transducer of FIG. 1a;

FIG. 10a is an isometric view of the sensor devices used in Example 1;

FIG. 10b is a plan view of the device of FIG. 10a;

Figure 1B:
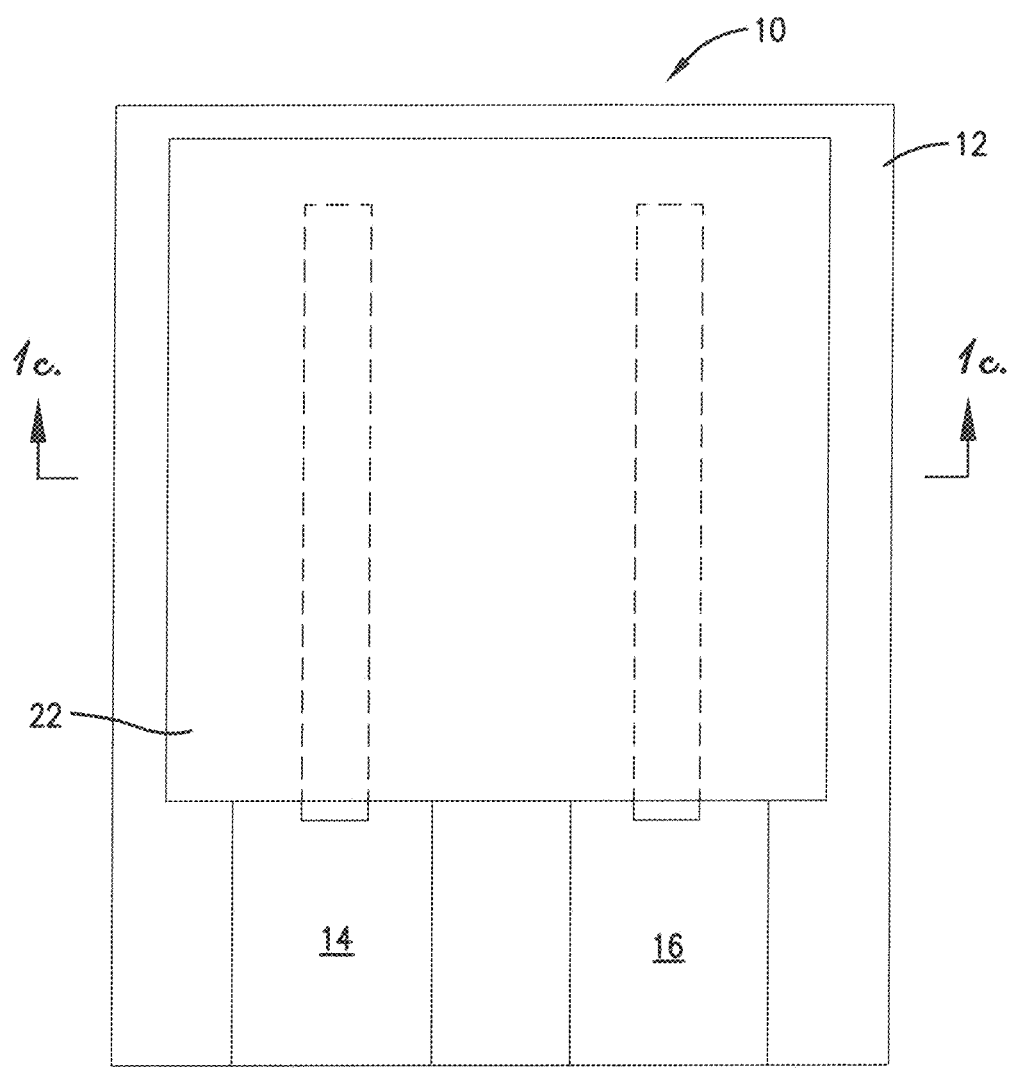

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Figure 1C:
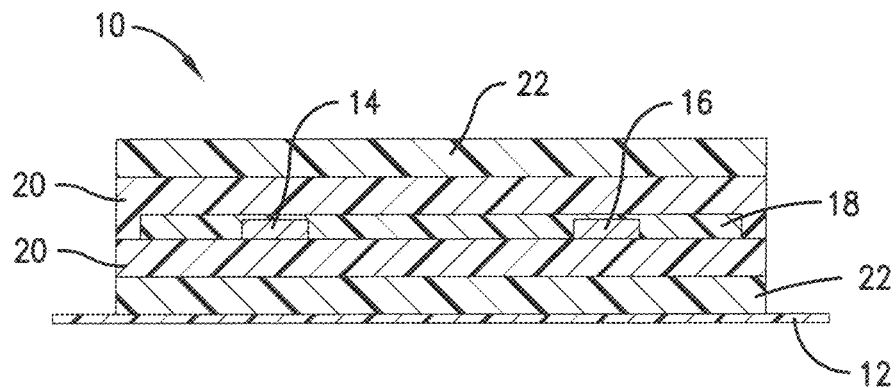
FIG. 1c is a cross-sectional view of the transducer of FIGS. 1a-1b, taken along lines 1c.

In more detail, and referring to FIGS. 1a, 1b, and 1c, one embodiment of a transducer 10 according to the invention is shown. The transducer 10 comprises a substrate 12, at least two electrodes 14, 16, and an active sensing layer 18. Each electrode 14, 16 has respective sidewalls as well as respective upper surfaces. The electrodes 14, 16 are positioned adjacent to the substrate 12, or on optional layers between the substrate 12 and electrodes 14, 16. Optional layers include, but are not limited to, signal enhancement layers 20 or filter layers 22 between the active sensing layer 18 and the environment, and isolation or filter layers 22 between the active sensing layer 18 and the substrate 12, as described in U.S. patent application Ser. No. 14/806,218, incorporated by reference herein. Importantly, the active sensing layer 18 is also in contact with each electrode.

Substrate

The substrate 12 may be formed from any number of materials, including those selected from the group consisting of polymers, ceramics, or single crystal. Preferably, the material is an organic polymer. Suitable organic polymers include those selected from the group consisting of polyimides (such as Kapton® film), polyamides, polysulfones, poly ether sulfones, polyether ether ketone (PEEK), polyethylene terpthalate (PET), polytetrafluoroethylene (PTFE, such as Teflon), acrylates, methacrylates, styrenics, cycloolefin polymers (such as Zeonor), cycloolefin copolymers, polyesters, and polyethylene naphthalates. The substrate 12 preferably has a low thermal conductivity, from 0.005 W/m-K to 1.0 W/m-K, more preferably from 0.01 W/m-K to 0.1 W/m-K.

Electrodes

Referring to FIGS. 1a, 1b, and 1c, it is noted that the active sensing layer 18 is touching the sidewall of both electrodes 14, 16. In another embodiment, the active sensing layer 18 conforms to electrodes 14, 16. That is, the active sensing layer 18 contacts the respective sidewalls and upper surfaces of the electrodes 14, 16. In another embodiment, the electrodes 14, 16 may be positioned on top of the active sensing layer 18 rather than under the active sensing layer 18 (i.e. their order could be "flipped"), provided contact is still achieved. Thus, any arrangement that results in the active sensing layer 18 contacting both electrodes 14, 16 is acceptable.

The electrodes 14, 16 are preferably planar electrodes, but could also be an inter-digitated electrode. Preferably, the electrodes 14, 16 have high electron or hole mobilities and large carrier concentrations. Suitable materials for forming electrodes 14, include those selected from the group consisting of silver, poly(3,4-ethylenedioxythiophene) (PEDOT), gold, highly-doped silicon, conductive carbon nanotubes (CNTs), and graphene inks, palladium, copper, aluminum, any conductive polymer, and CNT/graphene-conductive polymer composites. The preferred materials have a low Schottky barrier and low contact resistance to the active sensing layer 18. The electrode may be formed by any suitable technique, including those selected from the group consisting of screen printing, spray coating, Aerosol Jet® printing, ink-jet printing, flexographic printing, gravure printing, lithographic techniques, spin coating, evaporation, sputtering, and laser ablation.

Active Sensing Layer

The active sensing layer 18 provides an electronic signal that changes with a change in the active sensing layer 18. This change in electronic resistance may be the result of a change in its electronic structure, defect state, or electronic carrier density. Preferably, the electronic signal change is a change in resistance. Preferably, the resistance of the active sensing layer 18 is from about 5 k$\Omega$ to about 10 M$\Omega$, more preferably from about 100 k$\Omega$ to about 5 M$\Omega$, even more preferably from about 500 k$\Omega$ to about 2 M$\Omega$. Upon exposure to a gas, the resistance of the active sensing layer 18 should change proportionally to the change in the concentration of the gas. It will be appreciated that various gases and applications will require different sensitivities, but preferably the change in resistance should result in an output signal change of at least about 0.1% per 50 ppm change, and more preferably at least about 0.5% per 30 ppm change. Preferably, the material used to form the active sensing layer 18 is a planar material that can be provided as a film or fabric, as opposed to a wire, narrow bridge, rod, individual CNT, or the like. Additionally, the active sensing layer 18 preferably comprises a disordered conductor with a large number of defect states and a sheet or film morphology giving rise to irregular conduction paths. This disorder or irregularity leads to "junctions" among the particular component being utilized, and these junctions are important for the proper functioning of the active sensing layer 18. That is, ordered materials such as aligned CNTs are not suitable active layer materials. Suitable materials for the active sensing layer 18 include those selected from the group consisting of carbon nanotubes (metallic or semiconducting), a functionalized or non-functionalized carbon nanotube (CNT) fabric, amorphous carbon film, pyrolytic carbon, graphite, graphene, carbon fiber, fullerenes carbon soot, carbon black, silicon, ion-implanted and other conductive polymers (such as PEDOT:PSS, polyanilines, polyfluorenes, polyphenylenes, polypyrenes, polyazulenes, polynaphthalenes, polypyrroles, polycarbazoles, polyindoles, polyazepines, polyacetylenes, polyphenylenevinylenes, and polythiophenes), metal-particle-doped CNTs or graphene and composites and mixtures thereof.

The active sensing layer 18 is selected to be very thin, like a very thin "skin," approaching a 2-dimensional sheet or film. Thus, active sensing layer 18 should have an average thickness that is less than about 1000 nm, preferably less than about 200 nm, more preferably less than about 100 nm, and even more preferably from about 10 nm to about 100 nm. In a particularly preferred embodiment, the active sensing layer 18 has an average thickness of less than about 30 nm, and preferably from about 1 nm to about 30 nm. At such low thicknesses, active sensing layer 18 has negligible bulk properties such as mass, volume, and heat capacity. Therefore, this active sensing layer 18 takes on many of the chemical, physical, and biological characteristics of the surrounding layers. The active sensing layer 18 may be deposited by any suitable technique, including those selected from the group consisting of screen printing, spray coating, Aerosol Jet® printing, ink-jet printing, dip coating, airbrush techniques, flexographic printing, gravure printing, lithographic techniques, spin coating, evaporation, sputtering, lamination, ALD, CVD, and PECVD.

Signal Enhancement Layer

The signal enhancement layer 20 has a top surface and a bottom surface. The bottom surface of the signal enhancement layer 20 is adjacent to all or part of the active sensing layer 18, and preferably against an upper surface of the active sensing layer 18. The material of which signal enhancement layer 20 is formed is preferably selected from the group consisting of selective gas-absorbing materials, selective gas-adsorbing materials, and mixtures thereof. Suitable materials for signal enhancement layer 20 include those selected from the group consisting of metal oxides (such as tin oxide, iron oxides, vanadium oxide, and zinc oxide), metals (such as palladium, platinum, gold, silver, and iron), chalcogenide glasses (such as selenium, and arsenic selenide), and polymers (such as polyetherimides, pyrolyzed polysulfone, pyrolyzed polyacrylonitrile). That is, the signal enhancement layer 20 preferably has a conductivity of less than about $10^4$ S/m, more preferably less than about $10^3$ S/m, and even more preferably from about $10^{-2}$ S/m to about $10^2$ S/m. The sheet resistance of the signal enhancement layer 20 should be at least about 100 Ω/sq, preferably at least about 1,000 Ω/sq, and more preferably from about 1,000 Ω/sq to about 10,000 Ω/sq. The signal enhancement layer 20 may be deposited by any suitable technique, including those selected from the group consisting of screen printing, spray coating, Aerosol Jet® printing, ink-jet printing, flexographic printing, gravure printing, drawbar coating, dip coating, lithographic techniques, spin coating, evaporation, sputtering, lamination, ALD, CVD, and PECVD. The thickness of the signal enhancement layer 20 is preferably from about 50 nm to about 50 μm, more preferably from about 100 nm to about 4 μm, and even more preferably from about 100 nm to about 2 μm. The signal enhancement layer 20 should have a diffusion rate for the gas of at least about 50 g/m²/day, preferably at least about 500 g/m²/day, and more preferably from about 2000 g/m²/day to about 5000 g/m²/day, as measured by ASTM method F1249. In this embodiment, the signal enhancement layer 20 preferably has a diffusion rate for non-analytes of less than about 1 g/m²/day, more preferably less than about 0.01 g/m²/day, and even more preferably from about 0 g/m²/day to about 0.001 g/m²/day, as measured by ASTM method D-570.

In one embodiment, the signal enhancement layer 20 may react with the gas. For instance, the signal enhancement layer 20 may experience a chemical or physical change or reaction when contacted by the target gas. This chemical or physical change or reaction can further enhance or amplify the output signal from the active sensing layer 18 upon exposure to the gas. When the signal enhancement layer 20 is reactive, it should have an analyte solubility in the layer of at least about 0.8%, preferably at least about 2.0%, and more preferably from about 5.0% to about 10%, as measured by ASTM method D-570. The reactive signal enhancement layer 20 can be made of any non-conductive material or materials, including those selected from the group consisting of polymers (such as polyesters or polymethylmethacrylate [PMMA]), photoresists, ceramics, or metal composites, or mixtures thereof.

In another embodiment, the signal enhancement layer 20 may be intercalated into the active sensing layer 18. That is, rather than being deposited solely on top of or beneath the active sensing layer 18, it may be mixed in with the active sensing layer 18 or distributed within the active sensing layer 18 in some other fashion.

Filter Layer

The filter layer 22 comprises a top surface and a bottom surface and is located adjacent to the signal enhancement layer 20, and preferably the bottom surface is against the top surface of the signal enhancement layer 20. Alternatively, if a signal enhancement layer 20 is not present, the first side of the filter layer 22 is adjacent to the active sensing layer 18. More preferably, the first side of the filter layer 22 is against the second side the of active sensing layer 18 in this embodiment.

Regardless of the embodiment, the filter layer 22 is located between some or all of the electrodes 14, 16 and the environment. The filter layer 22 is designed to isolate the active sensing layer 18 from some environmental stimuli. That is, the filter layer 22 may enhance the function or selectivity of the transducer 10 by allowing only the desired environmental signal to contact and/or react with the active sensing layer 18. The material and properties of the filter layer 22 depend upon the type of transducer 10 being fabricated. The filter layer 22 is preferably formed from a material selected from the group consisting of metal films, polymeric films, ceramic films, single crystal films, ion-selective films, chemical-selective films, biological-selective films, metal oxide films, metal nitride films, organometallic films, and combinations of the foregoing. The filter layer 22 may be conductive or electrically insulating. Furthermore, the filter layer 22 may be deposited by any suitable technique, including those selected from the group consisting of screen printing, spray coating, Aerosol Jet® printing, ink-jet printing, flexographic printing, gravure printing, drawbar coating, dip coating, lithographic techniques, spin coating, evaporation, sputtering, lamination, laser ablation, ALD, CVD, and PECVD. The thickness of the filter layer 22 is preferably from about 10 nm to about 150 μm, more preferably from about 50 nm to about 100 μm, and even more preferably from about 100 nm to about 2 μm.

When present, the filter layer 22 preferentially allows the desired gas to pass through, while blocking any undesired environmental signals. Preferably, the filter layer 22 should have a high gas transmission rate and a low gas absorption and reflection rate. The filter layer 22 should have a diffusion rate for the gas of at least about 50 g/m²/day, preferably at least about 500 g/m²/day, and more preferably from about 2000 g/m²/day to about 5000 g/m²/day, as 10 measured by ASTM method F1249. For instance, for a humidity transducer 10, the filter layer 22 is a water-permeable membrane of a material, such as those selected from the group consisting of paper, cellulose paper, GoreTex materials, PVDF, and PTFE, and any porous, moisture-permeable layer. For non-analytes (gases or materials that are not the desired test gas), the filter layer 22 should have a diffusion rate with respect to non-analytes of less than about 1 g/m²/day, preferably less than about 0.01 g/m²/day, and more preferably less than about 0.001 g/m²/day, as measured by ASTM method F1249.

Multi-Pixel Transducer

Figure 2:
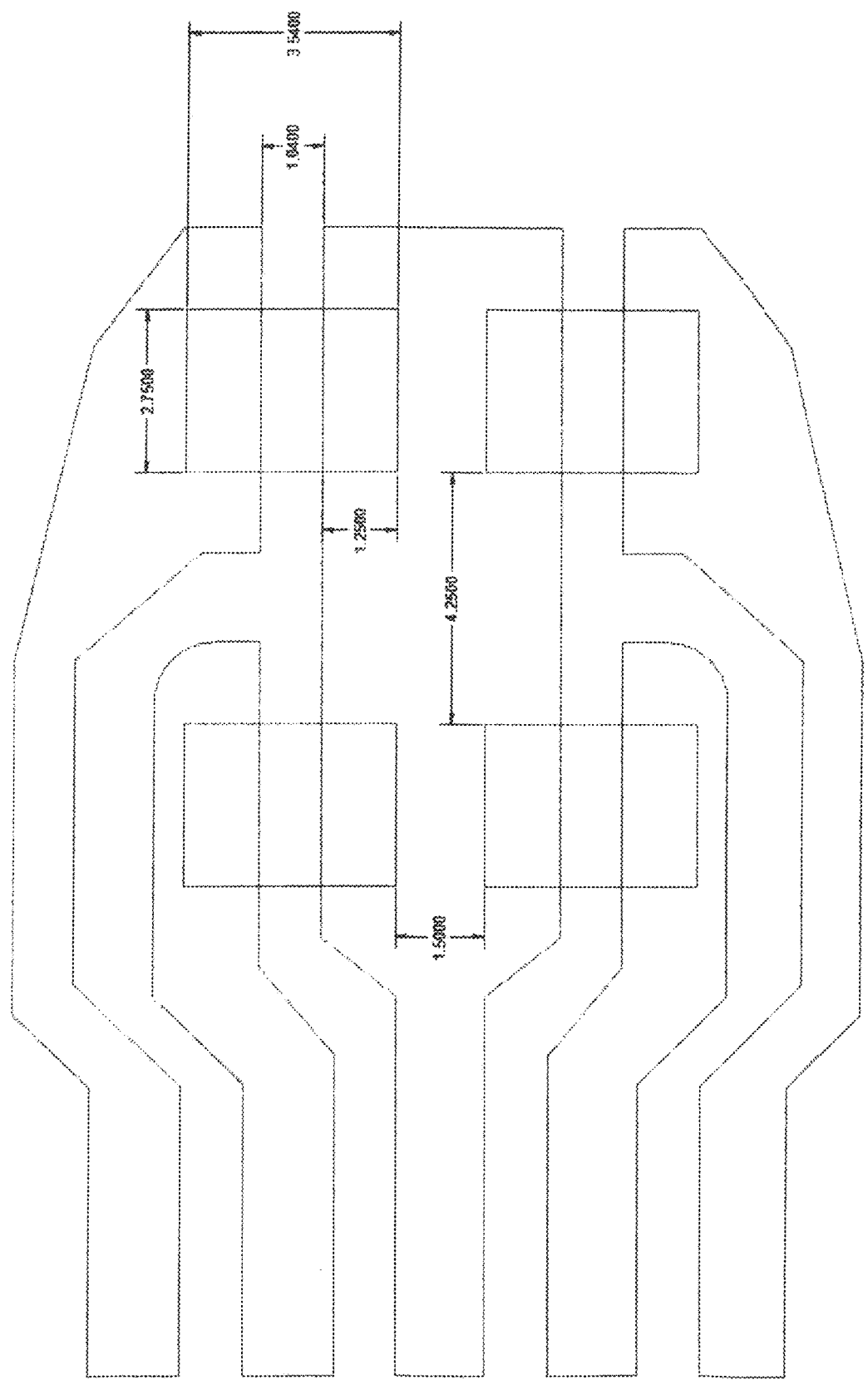
FIG. 2 is a plan view of a 4-pixel device according to the invention, where the units are in millimeters.

In another embodiment, multiple transducers may be arranged in a single device. Advantageously, the multiple transducers may be printed on an electrode configuration that minimizes the area of the device, allowing multiple "pixels" to be operated together or independently, to enable detection of more than one gas, or to enable more precise detection of a single gas. FIG. 2 shows a 4-pixel configuration.

Method of Use

It has been demonstrated that an electrical carrier current density of less than about 4,600 A/cm² can be applied to a 20-50-nm thick CNT active sensing layer 18 without damaging the layer, provided that the current is applied for a sufficiently short duration. Additionally, in some sensor structures, the polymer dielectric regions surrounding the active layer can withstand electric fields of about 4,200 V/cm for about 100 μs without dielectric breakdown. For such large energy densities (19×10⁶ W/cm³) to be maintained without material degradation, the energy must be delivered in a short pulse. The pulse must be less than about 100 μs, more preferably less than about 70 μs. For these short periods of time, this energy can be delivered along the carrier conduction pathway from electrical contact to electrical contact without harm to the physical morphology or chemical structure of the active sensing layer 18 and surrounding layers.

An environmental constituent that collects in and around the active layer will diffuse into the sensor structure from the immediate atmospheric environment surrounding the device. As the device comes to equilibrium, the environmental constituent diffuses into the structure, causing changes in the electrical conductivity of the active layer. For both analytes of interest as well as those not of interest, these changes can appear as hysteresis or instabilities in the device electrical conductivity.

The diffusion of the environmental constituent into and around the active layer can be reversed by putting energy into the system. However, for thin-film sensors, this can be difficult, as the energy density applied to the active layer must be sufficient to reverse the diffusion process, but low enough that it does not damage or otherwise irreversibly change the active layer and surrounding layers. Using the pulsed application of energy, the temperature of the active sensing layer 18 and surrounding layers can be precisely controlled, allowing the sensor to detect gases at elevated temperatures, as well as to raise the temperature of the device to a level sufficient to drive off gases or unwanted environmental constituents.

As this substantial energy density, u, is concentrated on the interfacial region between the conducting CNTs, where the Vander-Waals- and hydrogen-bonded environmental constituents interfere with the conduction process, substantial non-equilibrium heating is achieved. The temperature, T, of the region is determined by the following differential heat equation:

$$\rho c_p \frac{\partial T}{\partial t} - \nabla \cdot (\kappa \nabla T) = \frac{du}{dt}$$

where, ρ is the average density of the active and surrounding layers, $c_p$ is the specific heat of the active layer combined with surrounding regions, K is the thermal conductivity of the surrounding regions, and, t is time. If the temperature rise during the energy density pulse is to be maximized so that the environmental constituent can disassociate from the active layer and flow out of the region, then the lowest possible $c_p$ and κ are desired. For example, the CNT-based active layer combined with a polymer-based top layer (low κ) would allow for a much higher temperature spike in the active layer than if the CNT-based active layer was surrounded on one side with a silicon substrate (relatively high κ).

Figure 3:
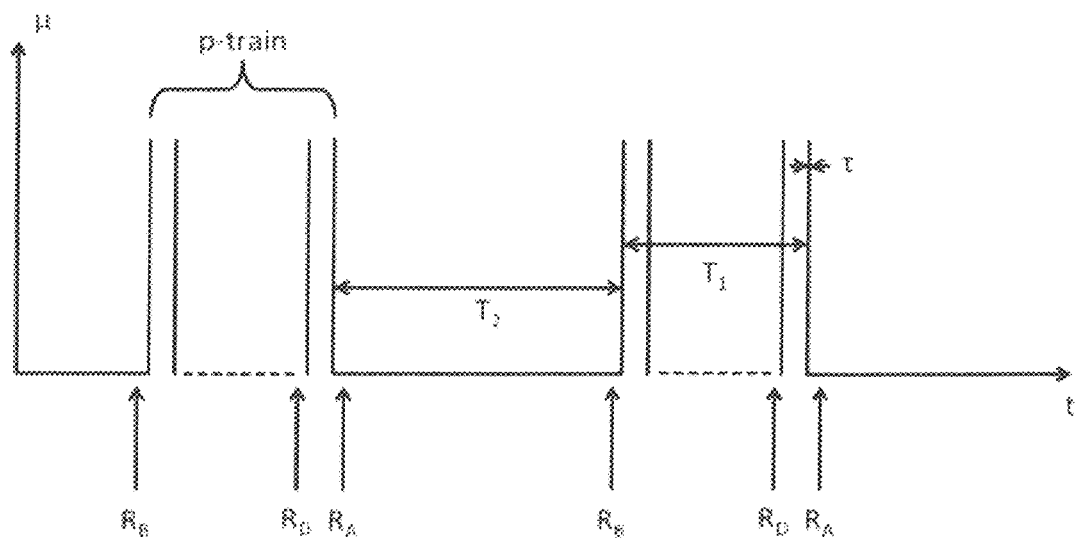
FIG. 3 is a pulse signal timing diagram showing one method of applying energy density according to the invention.

One especially preferred method of applying this energy density is by generating a "pulse train" of energy through the active layer. One such pulse train timing diagram is shown in FIG. 3. These electrical voltage pulses are connected through the device electrodes 14, 16 to heat the active sensing layer 18 in the sensor device. These pulses have a high enough average energy and repetition rate to quickly heat the active sensing layer 18 and surrounding region without thermal runaway, and a low enough peak energy so as to not permanently destroy the physical morphology and chemical structure of the active sensing layer 18 and surrounding layers. In FIG. 3, the vertical axis is the energy density and the horizontal axis is time. Individual energetic pulses of duration τ are shown as vertical lines. The pulses are arranged in pulse trains of a total number of pulses as determined by the product of the pulse time heating period, shown in the figure as $T_1$, and the pulse repetition rate. The resistance of the device is measured during the pulse heating period and is denoted by Rd. Immediately prior the pulse train, the resistance of active sensing layer 18 is measured as Rb in the figure. Immediately after the pulse train, the resistance of the active sensing layer 18 is measured as Ra in the figure. The time in the figure designated as $T_2$ is the time when the pixel is allowed to cool between pulse trains.

At time indicated by Ra in FIG. 3, electrical conductivity measurements of the active layer will represent the conductivity of the layer after heating. Depending on the length of the pulse train and the number of pulses, this measurement will either be the measurement without the influence of the analyte of interest or environmental interference, or the measurement of the analyte of interest of environmental influence at an elevated temperature.

The pulse train controls the final temperature. Each pixel receives a separate pulse train and comes to thermal equilibrium in less than about 100 ms as measured by an IR camera system. The thermal mass of the pixel/near substrate region prevents pixel temperature oscillation, provided the pulse train is correctly programmed. The parameters of the pulse train that control the final equilibrium temperature are pulse current, pulse repetition rate, and pulse duration. The amount of current necessary is dependent on pixel resistance and incident voltage, as pixel resistance changes during heating process and can be compensated by dynamically controlling the pulse duty cycle. The repetition rate and duration amount to the pulse duty cycle (percent of time where current is flowing). For example, to get a typical pixel to 200° C. requires an incident voltage of 100 V at a pixel resistance of about 10 kΩ with a duty cycle of about 8% (i.e. 10 mA flows through the pixel 8% of the time for an average current of 800 μA).

The duty cycle is used to control the temperature. The primary advantage of this approach is that the duty cycle is a timing signal that is derived (counted down) from a crystal oscillator. These oscillators have precisions of greater then 1 ppb, as opposed to controlling a voltage or current where the precision is limited to an order of 1 part per hundred (1%) or a few parts per thousand (0.3%). Therefore, timing signals in general allow for much finer control than voltage or current signals, a well-known principle of electronics. Thus, timing signals can be used to control the temperature very precisely.

The duty cycle (usually pulse repetition rate) is controlled to acquire a desired current flow through the pixel. The pixels have a calibration curve between pulse repetition rate and pixel temperature (this curve depends on pixel resistance, background temperature, architecture for thermal loss, radiation, conduction, and convection heat loss). This relationship between the current and pixel temperature is provided by a lookup table in the microcontroller.

As the current fluctuates, this error signal is fed back to the microcontroller and the pulse train is modified to keep the current (and thus temperature) constant. These error signals can be used to indicate the reaction of the pixel to the surrounding gas.

In a first mode of operation, only Rd is measured since the pulse train is never turned off, but instead measured (to determine current flow) to maintain a constant temperature. This mode of operation works for fast-reacting gases such as $H_2$ and CO.

In a second mode of operation, the temperature of the pixel can fluctuate between two or more temperatures, for example, the pulse train can be turned off for room temperature and then the pulse train turned on for another higher temperature. It should be noted that the system can be operated at many different pixel temperatures, or the pulse train never turns off but controls at a lower temperature between room temperature and then at a higher temperature.

In the mode described by Rb, Rd, and Ra, the system operates at two temperatures, room temperature (pulse train off) and a higher controlled temperature (pulse train on). Rb and Ra represent the resistance of the pixel at room/background temperature when the pulse train is off. Rd represents the resistance of the pixel when the pulse train is on at a higher temperature. This particular mode of operation is required when measuring water vapor gas concentration. Water vapor diffuses into the pixel with respect to air concentration, and this effect changes the resistance of the pixel and can be measured. However, not all of the water vapor leaves the pixel when the water vapor concentration surrounding the pixel is reduced. In many circumstances, some of the water remains trapped in the pixel. To get a precise measurement, the pixel must be heated to 100° C. to dry it. Therefore, Rb measures the water vapor concentration since last dried, Rd measures the pixel drying temperature, and Ra measures the clean dry pixel resistance. The difference between Rb and Ra is representative of the water vapor concentration in the air surrounding the pixel. This mode works for other gases such as $CO_2$ and volatile organic compounds.

In the first mode of operation, the curve representing the absorption of the gas as a function of temperature is the error signal (which represents fluctuations of the Rd) at different controlled temperatures when exposed to a gas. At low ppm or ppb gas concentrations this curve is expected to have the same shape, but vary in intensity as gas concentration levels vary.

In the second mode of operation, the indicative parameter of the temperature that eliminates gases from the pixel is Rd. For example, if the pixel is cleared at 100° C., the gas is likely water, if it is cleared at 50° C. the gas may be an alcohol, and if it is cleared at 170° C., the gas is likely $CO_2$. Each specific gas has a unique temperature where it is liberated from the pixel, depending on volatilization temperature and chemical potential between the gas and the pixel chemistry.

In the first mode, if there is a gas mixture present at the pixel, the final signal represents a linear combination of these curves for each gas. The unknown parameters are the concentration levels of each gas. The final signal can be fit to a library (database) of curves in real time by a least square fitting process. The end result would be a table of gas types and concentration levels.

In the second mode, each gas type can be determined as the pixel is heated through elevating temperature and by monitoring Rd. If Rd changes at a specific temperature, the temperature can be used to identify the gas.

Figure 4:
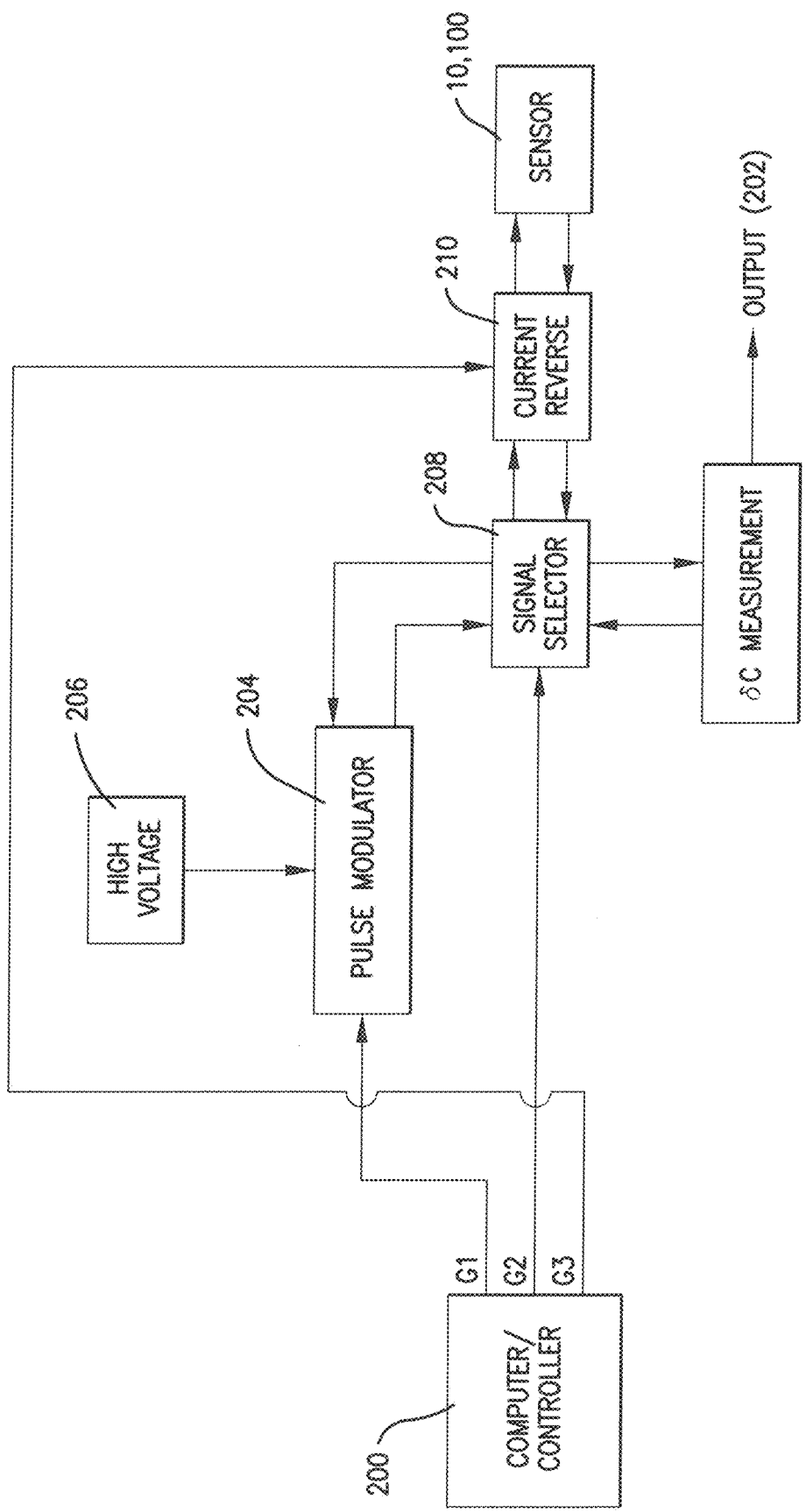
FIG. 4 is an electronic system block diagram for generating the pulse signal timing diagram of FIG. 3.

The electronic block diagram for generating the pulse signal timing diagram shown in FIG. 3 is shown in FIG. 4. The computer 200 controls the timing of the processes performed as described in FIG. 3 by digital control of outputs G1, G2, and G3. The circuit sends the computer 200 information on the active sensing layer 18 DC resistance through an output 202. High energy is provided to the pulse modulator 204 through a high-voltage source 206 shown at the top of FIG. 4. The pulse modulator 204 internally fixes the time between the pulses within the pulse train and the duration of the pulses, T. The total time of the pulse train, $T_1$, and thus the total energy delivered to the active layer is gated or controlled by the computer 200 by G1. The computer 200 selects between the pulse clearing and DC resistance measuring mode of operation by controlling G2 through the signal selector 208 in the center of FIG. 4. The computer 200 can also reverse the current through the active sensing layer 18 through G3 and the current reverse circuit 210. The software controls the time between the Rb, Rd, and Ra measurements, $T_2$, by controlling the signal selector 208 and the pulse modulator 204.

Figure 5:
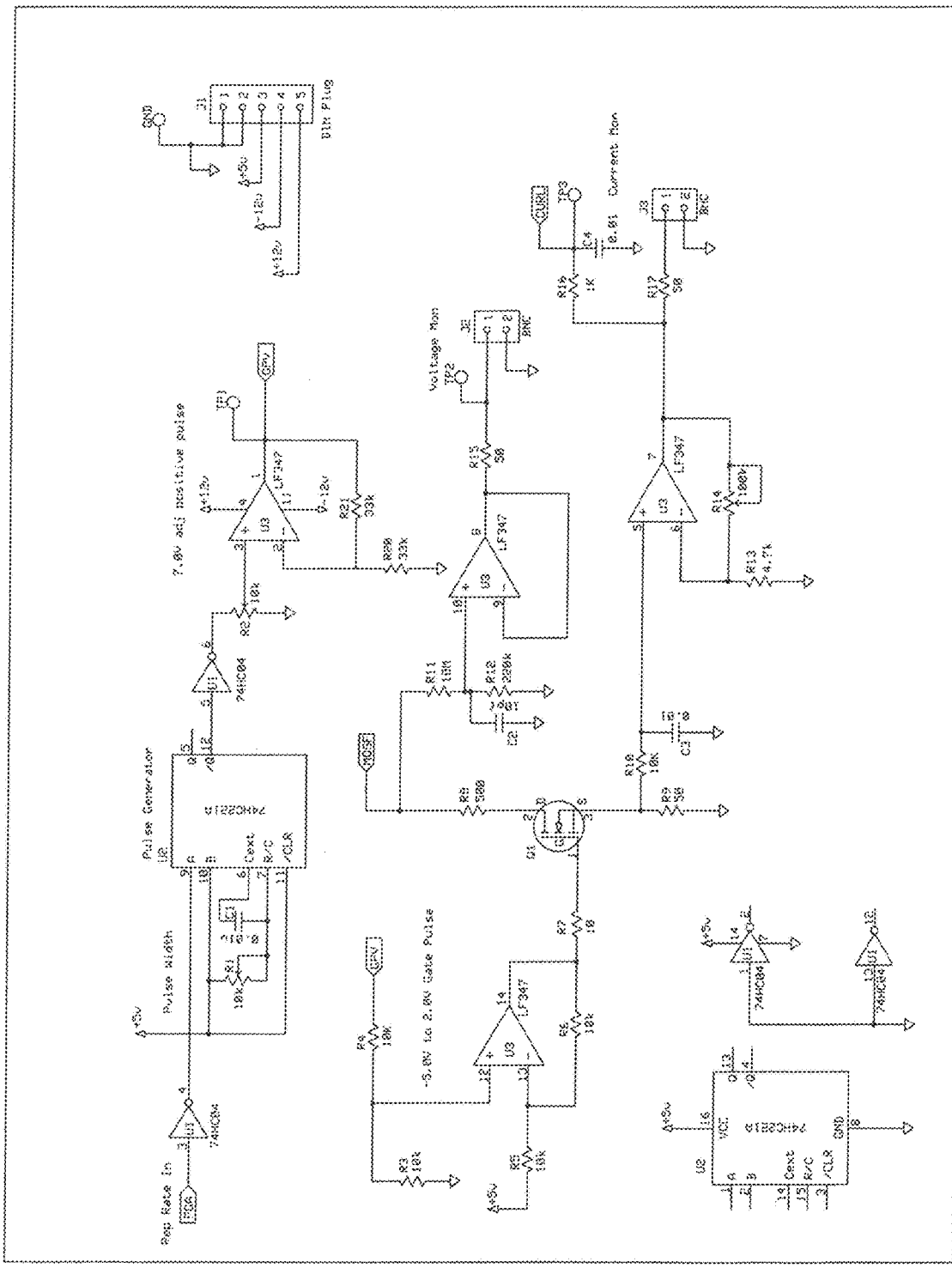
FIG. 5 is a circuit diagram of the pulse amplifier of the embodiment of FIGS. 3-4.
Figure 6:
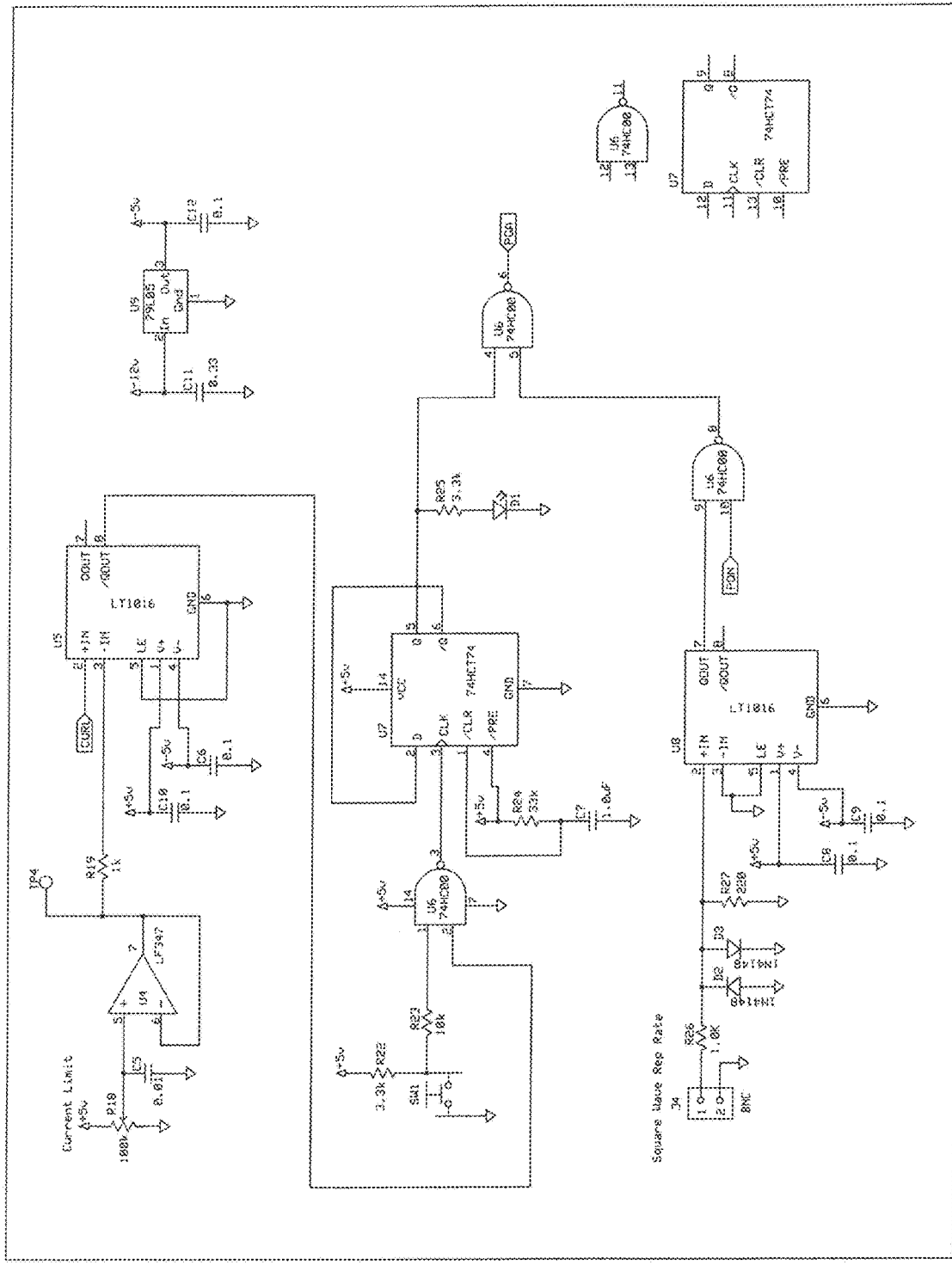
FIG. 6 is a circuit diagram of the pulse amplifier of the embodiment of FIGS. 3-4.

The circuit used in this embodiment is shown in FIGS. 5 and 6. The circuit uses a CMOS 74HC221 (complimentary metal-oxide semiconductor) one-shot device at U2 to provide the fixed pulse width of between 5 µs and 100 µs, adjustable by R1. A square wave signal that is gated or the computer through U6, or G1 in FIG. 4 triggers the integrated circuit U2. The computer G1 controls the time $T_1$ through the gate U6. The device at Q1 is a high performance IXYS IXTP3N100D2 depletion mode MOSFET (metal-oxide field-effect transistor) capable of sourcing 1000 V at a drain current of 3 A. Q1 is held off when the gate is at −5.0 V and pulsed to +2.0 V (as set by U3 and R2) to deliver the high-energy pulses. The operational amplifiers in U4 signal condition the digital outputs from the computer, G2 and G3, to control the signal selector at RLY1 and the current reverse at RLY2. The DC resistance measurement is accomplished through J5 and the active sensing layer 18 is connected to the circuit through J7. This embodiment also includes amplifiers connected to the networks at R11 and R12, and, R9 and R10 to measure the voltage and current respectively in the active sensing layer 18 during the pulse. These outputs can be connected to data acquisition devices at J2 and J3 for this embodiment of the pulse modulator section of the device. The pulses are repeatedly generated by the square wave input at J4 and the comparator at U8.

Figure 7:
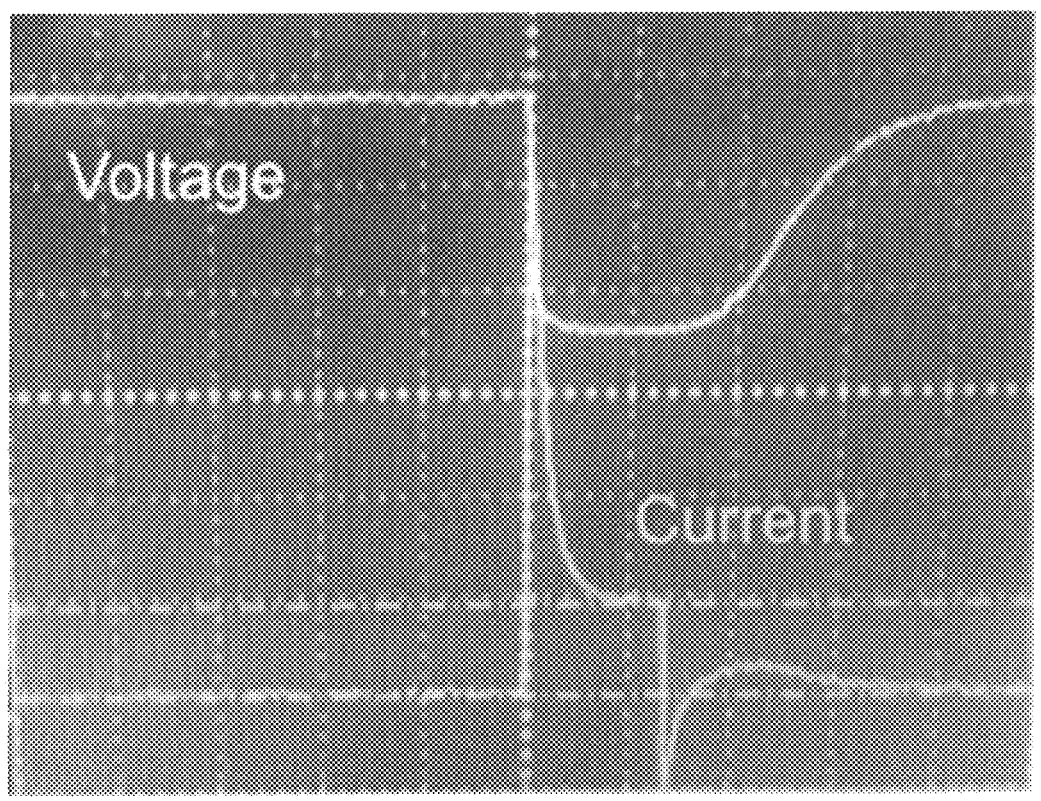
FIG. 7 is a graph depicting the voltage and current (as a function of time) through an inventive sensor device during the pulse train described in FIG. 3.

The output of a pulse peak voltage monitor (top) and pulse peak current monitor (bottom) for an exemplary pulse train is shown in FIG. 7. The pulse trains were incident on a test device and the resulting voltage across and current through the devices during the pulse train as described by FIG. 3 with results shown in FIG. 7. Before and after the pulse train, the resistance of the devices was measured. In this figure, horizontal scale is 50 µs per division and the spikes on either side of the pulse peak current pulse are a result of capacitive coupling when the pulse is quickly turned off and on. After the parasitic capacitor is charged, a steady-state current is evident. The voltage (upper line) is turned on rapidly, but decays slowly once the current pulse is turned off due to a small off resistance of the pulse amplifier. The spikes at either side of the current pulse are a result of stray capacitance in the sample holder.

Control of the temperature of the active layer and surrounding layers is possible by controlling the total incident pulse voltage (and therefore peak pulse energy), the pulse duration, $\tau$, the length of time the pulse train is incident on the active layer, $T_1$, and the pulse repetition rate within the pulse train.

Using this configuration, DC measurement system can be easily interchanged with an AC measurement, if impedance measurements are preferred over resistance measurements.

Method of Use

Temperature control of the active layer can be important in distinguishing between different environmental constituents that have diffused into the active layer and the surrounding region. For example, in $SnO_2$ metal cluster materials, the cluster-to-cluster transport of electrons is a function of $CO^-$ that is weakly bonded to the surface of the clusters. These bonds are broken (and the active layer is cleared of CO) at temperatures greater than 250° C. This is a very similar process to what is occurring between the conducting and insulating regions within the CNT active layer as explained above. Therefore, it would be expected that there would be thermal activation of the environmental interactions with the active layer.

The gas sensor comprises a pixel that includes two electrodes 14, 16 and a conductive active sensing layer 18. The active sensing layer 18 serves two roles in the gas sensor. First, its electronic properties can be affected by interactions with environmental stimuli, such as gases in the air. Preferably, this is a change in resistance between the electrodes 14, 16 as a current passes through the active sensing layer 18, referred to as "interaction resistance." Measurement of the interaction resistance using a low current density can be indicative of the type and amount of stimulus that is present in on the active sensing layer 18. Second, the active sensing layer 18 can serve as a micro- or nano-heater, as its temperature can be controlled by passing high current density between the electrodes 14, 16 through the active sensing layer 18. By varying the temperature of the sensor pixel, its interaction with environmental stimuli can be changed, which will change the electronic properties of the active sensing layer 18, resulting in a different interaction resistance.

Advantageously, the dual use of the active sensing layer 18 in the pixel as both the sensor and the heater offers distinct advantages over prior art gas sensors. While most prior art gas sensors rely on large heaters, the small size and thermal mass of the active sensing layer 18 allows the temperature of the pixel to be varied rapidly, independent of the surrounding device temperature. That is, the pixel has very little thermal inertia, so that temperature ramping, soaking, and sweeping can be achieved in less than a second. Additionally, very little power is consumed in reaching a specific temperature because of the very small heat capacity of the low-mass heater.

By controlling or ramping the temperature of the individual pixel to different temperatures, unique gas absorption characteristics can be measured. For instance, at different temperatures, a gas may adhere more or less strongly to the active sensing layer 18, or it may be driven off completely. These thermally induced different gas absorption characteristics can be used to produce characteristic absorption curves versus temperature for different gases.

Figure 8:
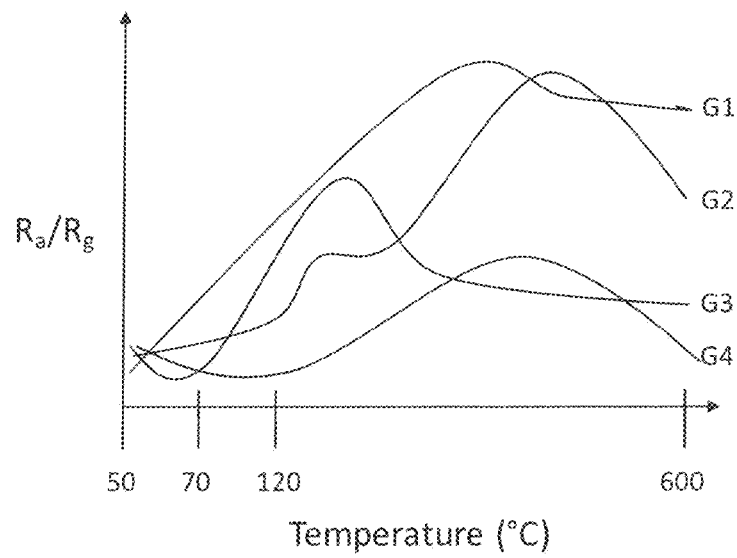
FIG. 8 is a graph showing the hypothetical thermal absorption spectra to illustrate the inventive method of modeling a sensor device response to determine gas composition and concentration.

It is well known that the absorption, adsorption, or reaction of various gases with a material will change the resistance of various materials changes as a function of concentration as well as a function of temperature. FIG. 8 shows four hypothetical gas absorption curves. The curves in FIG. 8 can be used to model the response of a sensor device in determining gas composition and concentration. In the figure, the thermal absorption spectra of different gases are shown by different curves G1 through G4. Each different gas has a different gas absorption spectra as a function of temperature.

Figure 9:
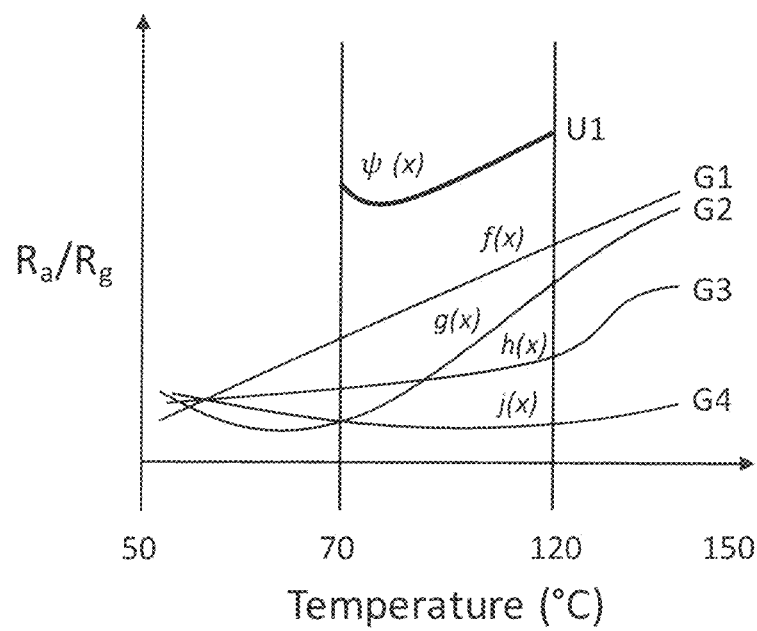
FIG. 9 is a graph showing exemplary curves in the 70-120° C. temperature range of four hypothetical gases.

Also shown in FIG. 8 is a typical temperature range of gas spectra, where the gas absorption process is measured from room temperature to about 600° C. depending on the specific gas type. FIG. 9 shows exemplary curves in a region of 70° C. to 120° C., as curves for gases G1-G4 with characteristic functions f(x), g(x), h(x), and j(x). In operation, the temperature of the active sensing layer 18 can be ramped through this range, the change of resistance of the active sensing layer 18 can be measured during this temperature ramp process. The result could be a curve represented by $\psi(x)$, where $x=T/T_0$ and $T_0$ is a constant characteristic temperature. The gas composition can be obtained to a first approximation as a fit to the equation:

$$\psi(x)=n_1f(x)+n_2g(x)+n_3h(x)+n_4j(x)$$

where the $n_1$, $n_2$, $n_3$, $n_4$ represent the concentrations of gases G1-G4 through their respective functions f(x), g (x), h(x), j (x). For example, if the unknown gas is G1, the gas is determined by matching the curve shape f(x) and concentration is determined by the magnitude $n_1$. If f(x) is linear, then the type is determined by the slope and concentration is determined by the y-intercept.

The measured resistances can be compared to known spectra to determine the identity and concentration of various gases or combinations of gases. As concentration is increased or decreased, the magnitude of the y-intercept of the signal function increases or decreases, but not the slope of the line, which is characteristic of the absorption spectrum shape and will not change at most concentration levels.

Additionally, various signal enhancement layers 20 or filter layers 22 can be used in conjunction with the active sensing layer 18 to further increase the response of the pixel or to increase the selectivity of the pixel. One or more materials that interacts easily with the gas of interest can be used as a signal enhancement layer 20, either incorporated within the active sensing layer 18, or between the active sensing layer 18 and the environment. Such a signal enhancement layer 20 can increase the interaction resistance change, resulting in lower detection thresholds and better signal-to-noise ratios. Alternatively, a filter layer 22 may be positioned between the active sensing layer 18 and the environment to prevent unwanted stimuli from interacting with the active sensing layer 18, which can further increase the sensitivity and specificity of the pixel. It will be appreciated that both a signal enhancement layer 20 or layers and a filter layer 22 or filter layers 22 could be used in conjunction with one another.

Advantageously, multiple pixels can be used together as an array. In one embodiment, each pixel has the same composition. When used with a substrate 12 having a low thermal conductivity, the temperature of each pixel can be controlled independently, and the interaction resistance at various temperatures can be measured simultaneously. This can result in faster sensor speeds, since a range of temperatures can be measured at once, rather than ramping a single sensor pixel through different temperatures.

In another embodiment, one or more pixels (also referred to as pixel sensors) can have a different composition. That is, the pixels can be "mixed and matched," so that some pixels have active sensing layers formed from a single, uniform composition (i.e., the same composition chemically throughout the layer), while some pixels could have active sensing layers that are a mixture of different compositions (e.g., a signal enhancement material intermixed with another material, such as carbon nanotubes). A signal enhancement layer could be avoided in each pixel, or it could be included in one or more (or even every) pixel of the particular sensor array. In this embodiment, each pixel may be controlled to the same temperature, or to different temperatures. Pixels of different compositions will interact with various gases differently, and can be used to determine the identity and concentration of one gas more precisely, or can determine the identity and concentration of more than one gas simultaneously.

Temperature control is tied to sensor precision by the gas absorption curve properties as a function of temperature. If the absorption curve is rapidly changing in the vicinity of the device temperature, control must be maintained so that fluctuations in background temperature do not cause false positive signals. Therefore, additional temperature and relative humidity sensors may be needed to control the baseline of the sensor system. If the background temperature and gas absorption curve are well known, an adjusted energy can be dissipated in the heater to achieve the desired temperature.

In a further embodiment, the invention provides a microheater or even a nanoheater. In this embodiment, a heating layer can be heated by application of a series of electrical pulses. Each individual pulse is preferably less than about 100 microseconds, more preferably less than about 70 microseconds, and even more preferably from about 1 microsecond to about 70 microseconds. A series of pulses can be delivered to the heating layer for a duration of time in order to heat the layer via Joule or ohmic heating. This series of pulses preferably has a short duration, i.e., less than about 5 seconds, preferably less than about 3 seconds, more preferably less than about 1 second, and even more preferably from about 1 microsecond to about 1 second.

The voltage used for these electrical pulses is preferably from about 25 V to about 500 V, preferably from about 50 V to about 350 V, and even more preferably from about 100 V to about 200 V. The electrical carrier current density in the heating layer is varied depending upon the resistance and desired temperature range, but typically it is from about 1,000 A/cm$^2$ to about 10,000 A/cm$^2$, preferably from about 1,500 A/cm$^2$ to about 7,000 A/cm$^2$, and more preferably from about 2,000 A/cm$^2$ to about 5,000 A/cm$^2$. The heating layer experiences an increase in temperature of at least about 50° C., preferably at least about 100° C., more preferably at least about 150° C., and even more preferably from about 200° C. to about 300° C.

The thicknesses of the heating layer, the material of which it is formed, and other properties are the same as those described above with respect to the active sensing layer. However, in a preferred embodiment, the heating layer consists essentially of, or even consists of, carbon nanotubes.

As described previously, this heating feature can be used to "reset" or clear a sensor device, but it will be appreciated that this embodiment of the invention is also useful in other applications outside of the sensor technology. For example, this feature is useful in environments where heating needs to be substantially isolated from layers, components, devices, etc., near the heating layer. This embodiment finds particular use in environments where moisture (such as from water) and/or volatile organic compounds ("VOCs") can be detrimental, and a controlled removal of that moisture and/or VOCs is needed, particularly when that environment is a micro- or even nano-environment. The inventive method will result in removal or evaporation of at least some of that particular target compound to be removed, preferably at least about 70% of the target compound, more preferably at least about 90% of the target compound, and even more preferably about 100% of the target compound.

One example of such an environment is in the microelectronics realm, where even a small amount of moisture that is present can be detrimental to the electronics present, but at the same time heating of those electronics would damage them. In many such environments, the heating layer would be positioned adjacent a polymer layer, light-emitting diodes ("LEDs," but particularly organic LEDs), glass layers, or the like, and the heating layer could be heated to remove any moisture but without heating the polymer layer, LEDs, or other nearby components, which could lead to softening and/or movement thereof. Regardless of the type of layer or component adjacent to the heating layer, that layer or component preferably experiences a temperature increase of less than about 20° C., preferably less than about 10° C., more preferably less than about 5° C., and even more preferably about 0° C.

In some applications, a single series of pulses at the voltage and for the time frames discussed above is all that is needed. For example, if the heating layer is included in a microelectronic device where moisture and/or VOC removal was needed, one series pulse given as described above could be sufficient to remove any moisture or VOC that was present within the device. In some applications, it may be desirable to repeat the series one or more times, with gaps between those repeats.

EXAMPLES

The following examples set forth preferred methods in accordance with the invention. It is to be understood, however, that these examples are provided by way of illustration, and nothing therein should be taken as a limitation upon the overall scope of the invention.

Example 1

Fabrication of a CNT-Active-Layer Environmental Sensor

Figure 10B:
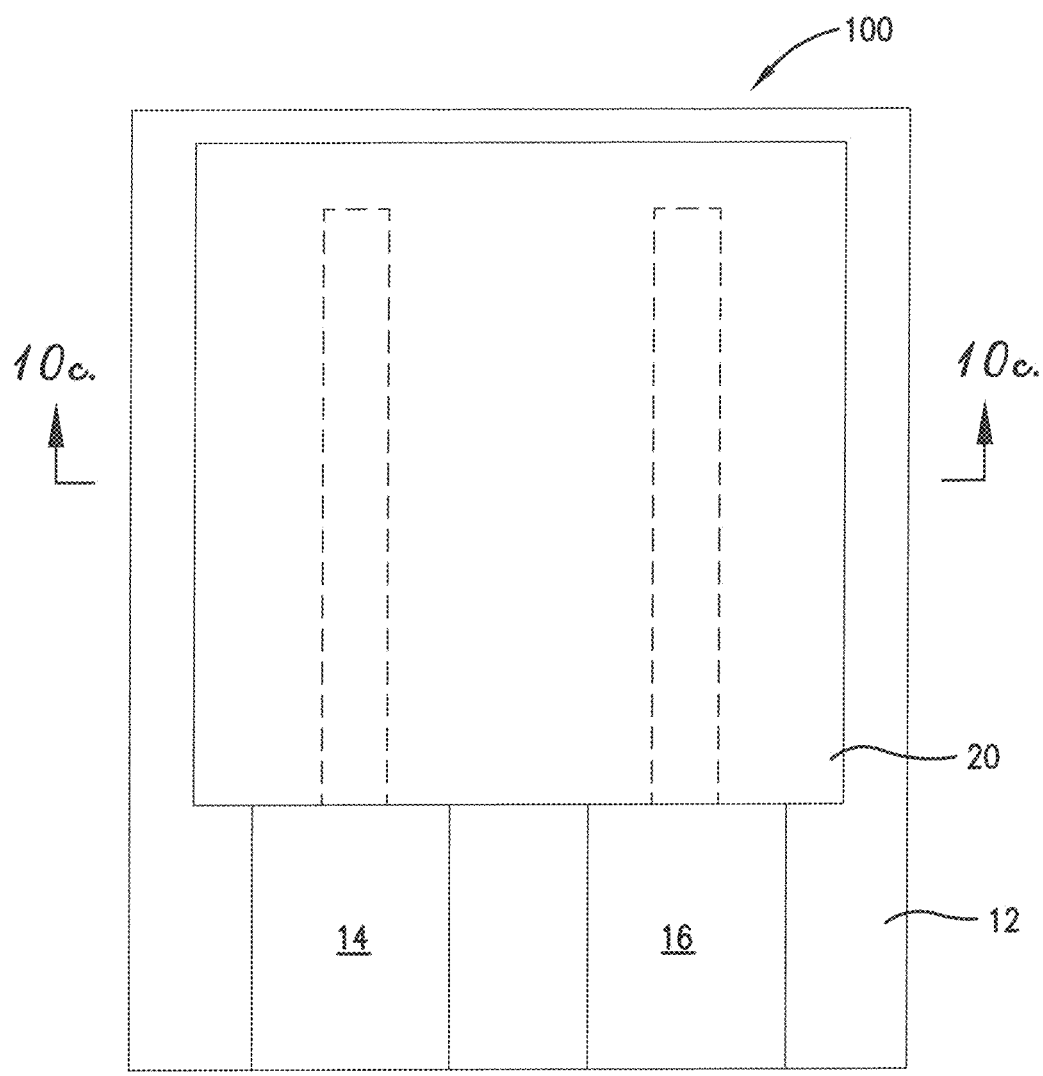
Figure 10C:
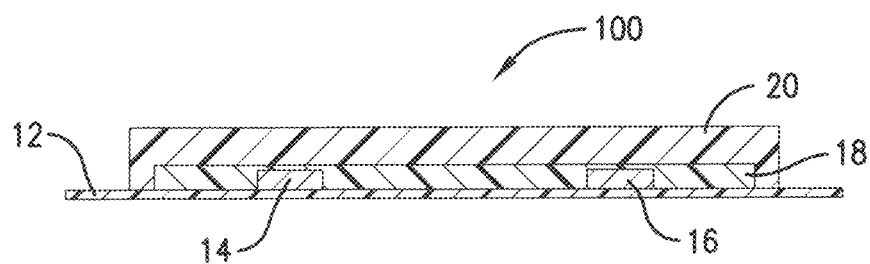
FIG. 10c is a cross-sectional view of the device of FIGS. 10a-10b, taken along lines 10c.
Figure 11:
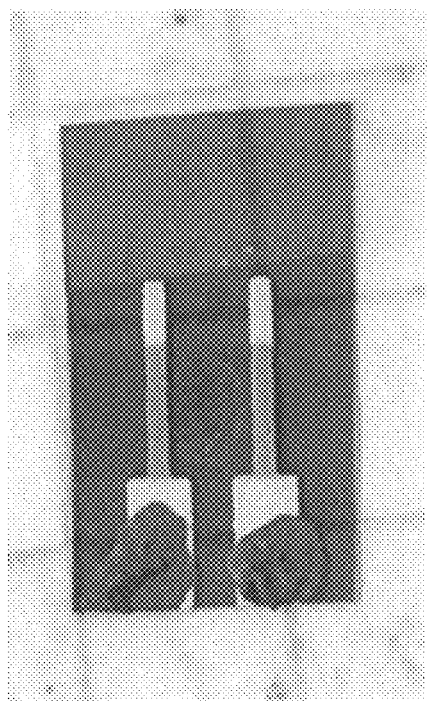
FIG. 11 is a photograph of a sensor device used in Example 1.

A number of sensor test devices, such as a transducer 100, in the configuration shown in FIGS. 10*a*, 10*b*, and 10*c* were synthesized. The substrate 12 for the devices was Kapton® HN film, 125 microns thick (DuPont, Circleville, Ohio). Silver electrodes 14, 16 were then screen printed, using AG-800 silver conductive ink (Conductive Compounds), (screen printer model: AT-60PD, screen: polyester, 230 threads/inch, flood/squeegee speed: 225 mm/s, flood bar pressure: 10 μsi, squeegee pressure: 25 μsi) onto the substrate 12 and cured in the conveyor oven at 130° C. at a 10"/min speed. The cured Ag electrodes 14, 16 had a thickness of 5 μm±2 μm. The CNT active layer (Brewer Science, Inc., Rolla, Mo.) was spray coated across the electrodes 14, 16 using the following parameters: platen temperature: 135° C., scan width: 2 mm, flow rate: 10 ml/hr, scan speed: 60 mm/s, spray head: Sono-Tek, model: 048-00214 using 3 passes across the electrode region. The devices were then spray coated with OptiStack® SOC304 material (Brewer Science, Rolla, Mo.) directly on top of the CNT active layer. The spray coating conditions for the OptiStack® material were: 2 passes at a spray width of 1 mm, at a syringe speed of 10 mL/hr, sonication power set at 2.4 W, air pressure of 1 psi, a scan speed of 60 mm/s, and a platen temperature of 135° C.

Multiple devices were selected for testing. The selected devices were separated and pinned with a short male tin crimp pin, #13595-12 from Nicomatic North America, Inc. (Warminster, Pa.). Starting resistances for the selected devices were nominally between 60 kΩ and 600 kΩ directly after synthesis in normal atmospheric (STP) conditions and 25% RH.

Example 2

Pulse Clearing of a Humidity Sensor

The sensors prepared in Example 1 were measured in an environmental chamber where both the temperature and relative humidity were varied. The DC resistance of the active layers of the samples was measured, first without using pulse clearing, and then using pulse clearing.

Figure 12:
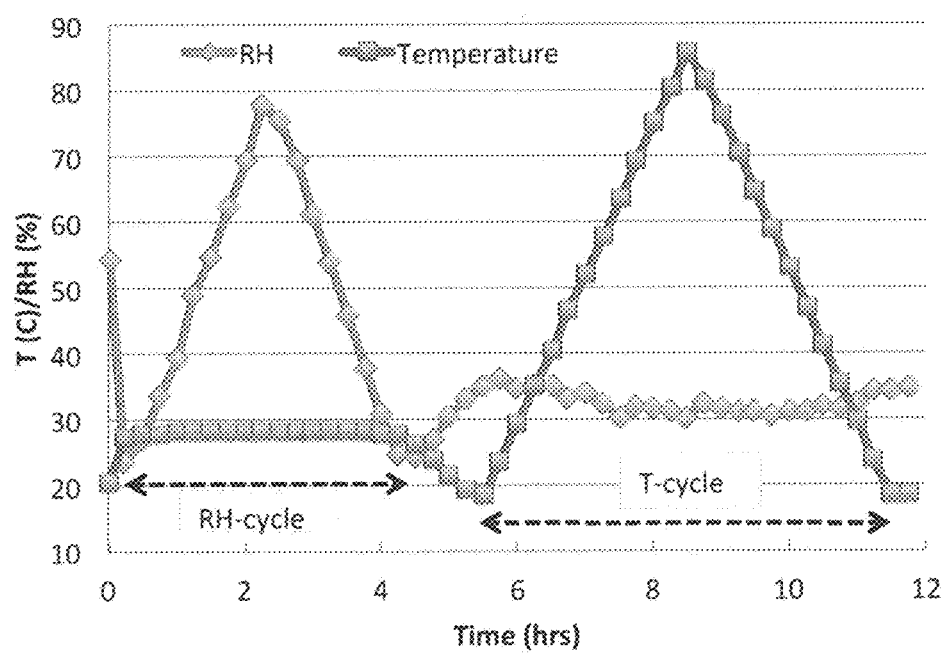
FIG. 12 is a graph depicting the temperature and relative humidity profile of the environmental chamber used in Example 2.

The environmental chamber provided controlled fluctuations in the relative humidity and temperature environment surrounding the samples. The environmental chamber also included also two calibrated, standardized sensors, a Honeywell© HIH-4000-003 humidity sensor and a National Instruments© LM335Z Precision Temperature Sensor, for measuring the relative humidity and temperature inside the environmental chamber in close proximity to sensors under test. The environmental chamber was programmed to produce the environment shown in FIG. 12. The profile was divided into two cycles, a RH cycle and a T cycle. During the RH cycle, the temperature was constant, and during the T cycle the RH was constant. The RH went to 90% after 12 hours (not shown).

In this example, variable electronic current pulse train parameters were a pulse width of 70 μs, a repetition rate of 400 Hz, and a constant peak pulse voltage of 100 V. The electronic pulse train was used to heat the active sensing layer 18 in the pixel for a period of 4.4 seconds, and then the resistance was measured. After an additional 15 minutes where the pixel was allowed to cool and collect moisture, the pulse train was again used to heat the pixel for 4.4 seconds and this pattern was repeated throughout the experiment.

Figure 13:
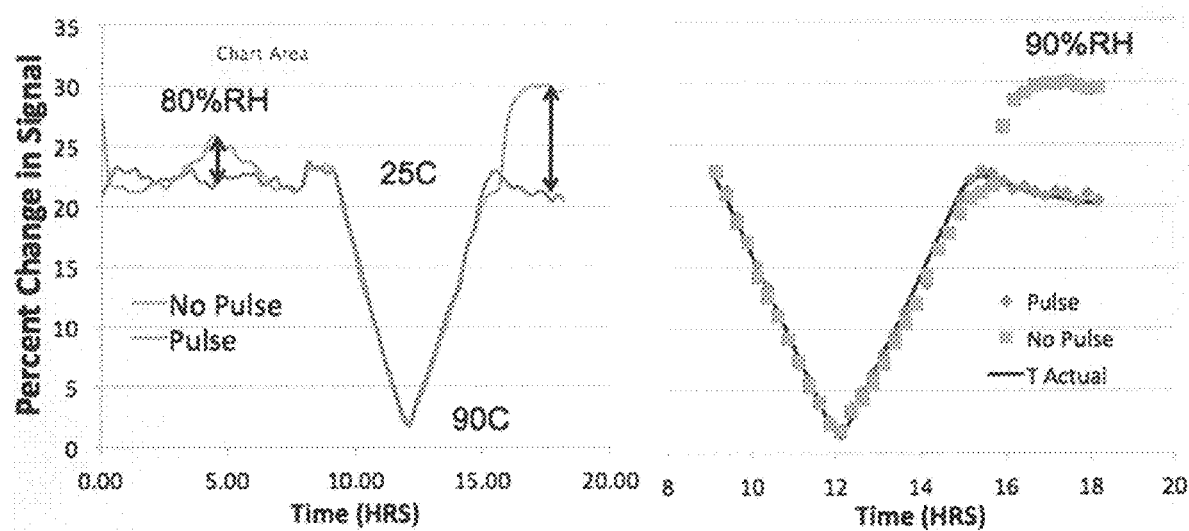
FIG. 13 is a graph showing the signal change vs. time both with and without pulse clearing as described in Example 2.
Figure 14:
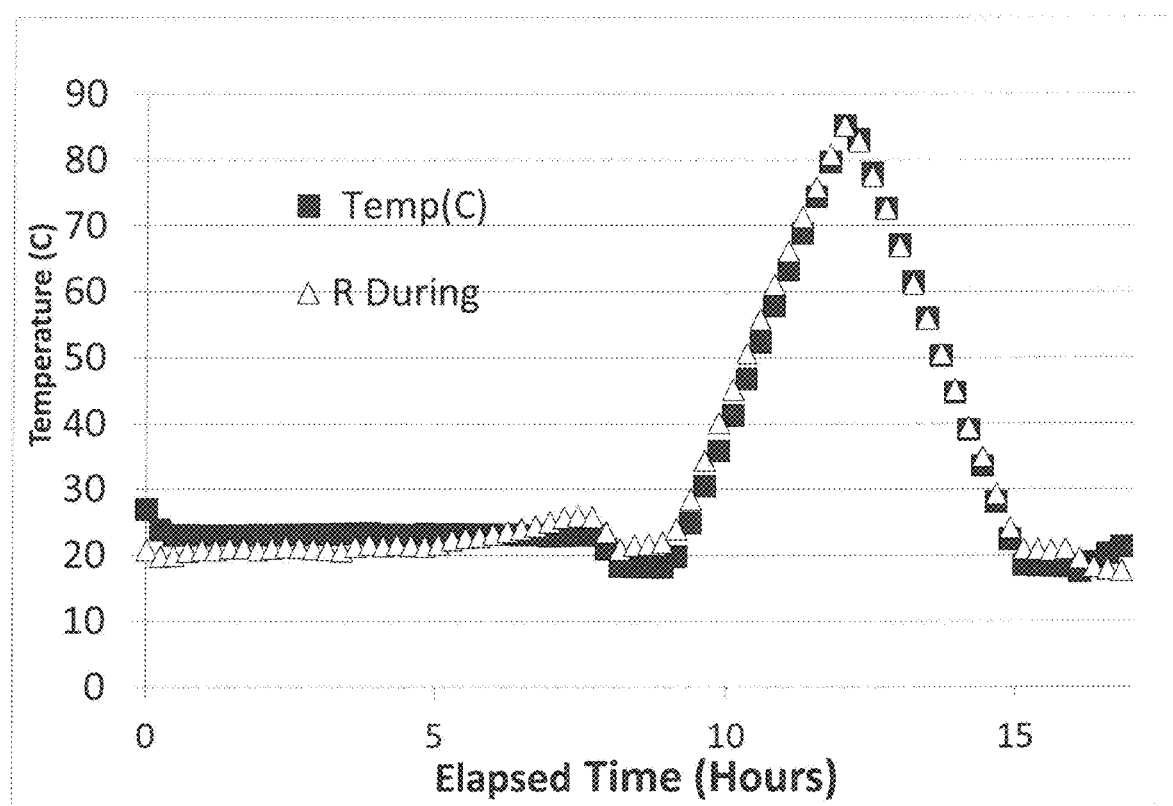
FIG. 14 is a graph showing the actual temperature and device resistance converted to temperature after an inventive device was put through the same temperature and humidity cycle shown in FIG. 12.

The DC resistance of the active layer in the samples was measured just after the pulse clearing train, at a time indicated by Ra in FIG. 3. The current was reversed through the active layer and the DC resistance was measured again. The actual $R_{meas}$ shown in FIG. 13 was then calculated to be the average of the forward and reversed values. In FIG. 13, the blue data represents measurements of the DC resistance without pulse clearing, and the orange data represents measurements with pulse clearing. The data on the right of FIG. 13 clearly shows (red diamonds) that at 90% relative humidity there is a 10% contribution to the conductivity from water vapor inside the active layer and in the surrounding region. After pulse clearing this region of water vapor, the resistance of the sample (blue squares) follows the actual temperature of the sample to better than 1%. Another result is shown in FIG. 14, where the sensor was put through the same temperature and humidity cycle shown in FIG. 12, with the resistance during the pulse converted to a temperature is plotted alongside the temperature measured by the standardized sensor. The correlation between the actual temperature of the device as measured by the standard sensor (square) and the device resistance converted to a temperature (triangle) are shown in FIG. 14. These results indicate that the influence of the environmental humidity on the resistance has been reduced or eliminated.

Figure 15:
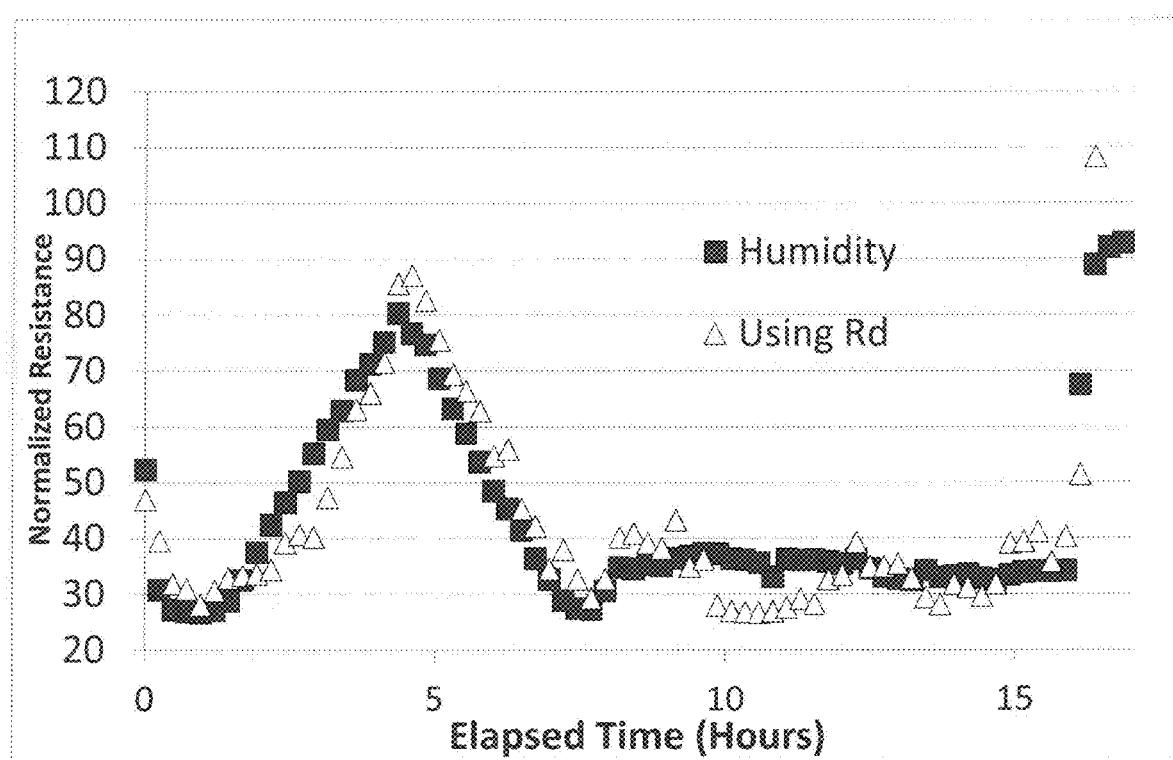
FIG. 15 is a graph depicting the humidity both as measured and as determined by the difference between the resistance before the pulse train and resistance during the pulse train, as described in Example 2.
Figure 16:
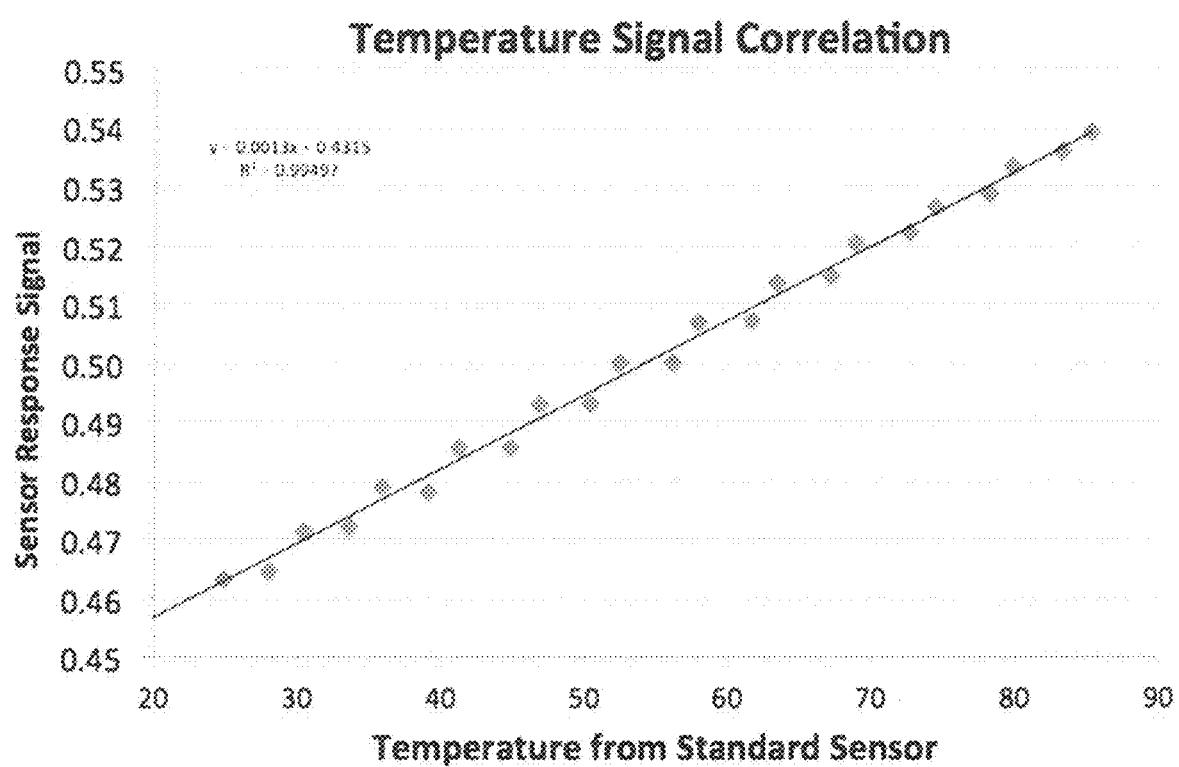
FIG. 16 is a graph of the device current during the pulse train as a function of the temperature of the device during the temperature cycle, as described in Example 2.
Figure 17:
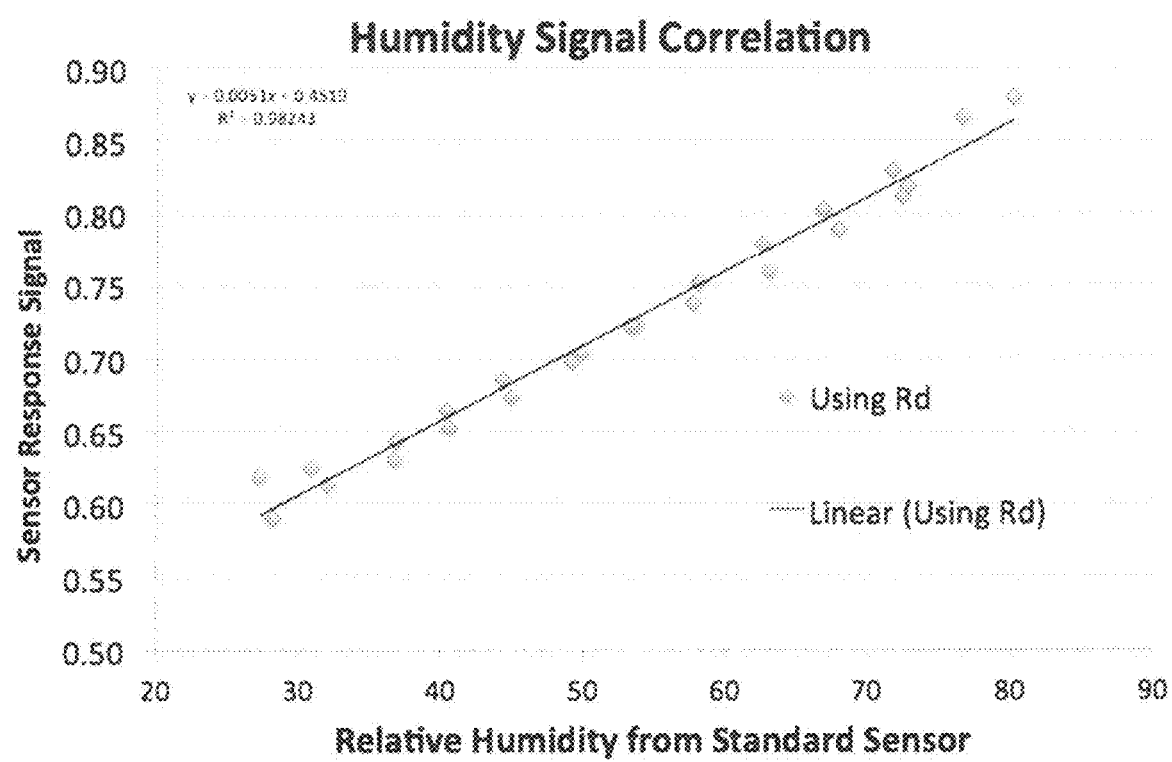
FIG. 17 is a graph showing the sensor signal as the difference in current before and during the pulse train as a function of the device humidity during the RH cycle as described in Example 3.

When used as a humidity sensor, this sensor and pulse clearing technology can determine the difference caused by exposure to humidity by measuring the resistance of the active layer with and without the pulse train as shown in FIG. 15. FIG. 15 shows the humidity as measured by the standard sensor (square) and the humidity as determined by the difference between the resistance before the pulse train and resistance during the pulse train (triangle). These two measurements correlate well with one another and the device is able to measure humidity without a temperature cross-signal during the temperature cycle. By calibrating this difference to the actual RH, the environmental humidity signal can be determined. FIGS. 16 and 17 show how the single sensor can measure both temperature and humidity independent of each other by changing the mode of operation. The temperature can be measured by using the resistance during the pulse train, and humidity can be measured by taking the difference in current before and during the pulse train. FIG. 16 shows the device current (~1/R) during the pulse train as a function of the temperature of the device during the temperature cycle. The linear relationship indicates that in this measurement mode, the sensor is the good temperature sensor. FIG. 17 shows the sensor signal as the difference in current before and during the pulse train as a function of the device humidity during the RH cycle. This linear relationship indicates the sensor is a good humidity sensor when operated in this mode.

Example 3

Prevention of Water Diffusion by Using a CNT Film and Pulse Clearing

A sensor was fabricated as in Example 1, except the substrate 12 used was a transparent PET substrate 12 with a CNT active layer estimated to be 30±20 nm thick. At these very low active layer thicknesses, the mass of the active layer is negligible and thus the temperature rise in the region surrounding the active layer is more a function of heat capacity in the surrounding signal enhancement layers 20 or substrate 12 than it is of the active layer thickness. At these thicknesses, the active layer in the window between the electrodes 14, 16 is transparent, making the entire device (active layer and substrate 12) transparent in this window, which is essential for some applications, such as OLED. In this example, the window between the electrodes 14, 16 was 2.54 mm square, but can be scaled to much larger geometries since the resistance per square is a constant.

The RH in the environmental chamber was held at a constant 88% and the temperature was held constant at 28° C. The sensor was placed in the environmental chamber for three hours so that it could reach equilibrium with the surrounding environment. After three hours, the resistance of the sample dropped by 12%. This change was a result of the net effect of an increased temperature that drops the resistance and an increased humidity that raises the resistance.

By using computer control of the gate at U6 as described above, a 4.5-second pulse train that generated heat in the active layer was followed by a 900-second interval where no heat was produced in the active layer. This low duty cycle process was used to minimize the average power dissipation in the active layer required to keep the region surrounding the active layer dry. Although the speed of the diffusion of water through the dielectric films is slow, this process demonstrates that very low average powers with short high peak energies can effectively block water from the active layer even in very hot and humid conditions. At these low pulse train duty cycles (4.5/900=0.5%) the total energy required for the blocking of water diffusion is small and the technology has practical value, such as for water-sensitive OLEDs.

Figure 18:
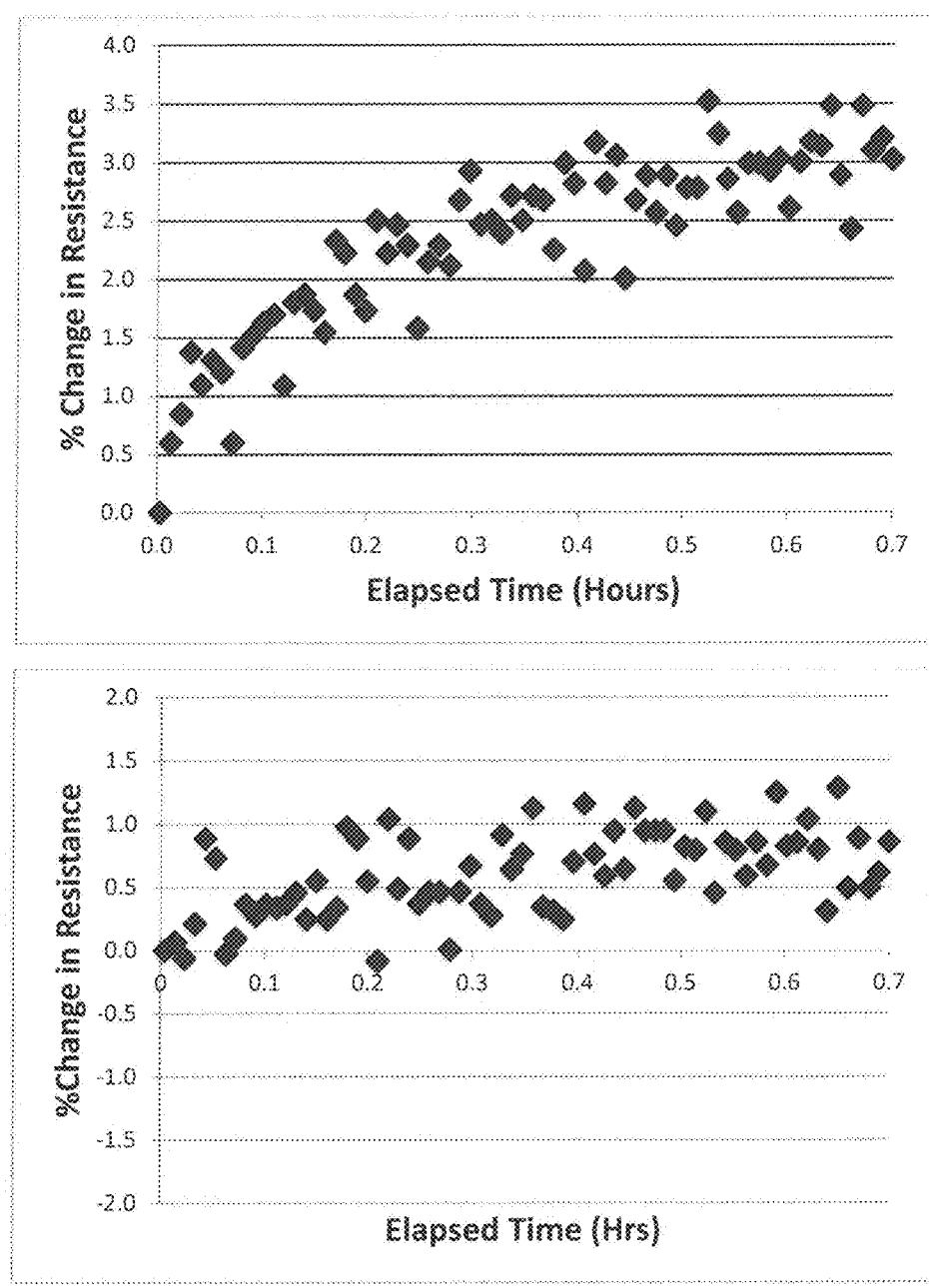
FIG. 18 is a graph of the resistance of the sensor of Example 3 with pulse trains at 15-minute intervals.

FIG. 18 shows the results for the resistance of the active layer as a function of time given a pulse-clearing signal of the form shown in FIG. 3. The upper graph shows the drying process after the sample device was in the chamber at 88% RH and 28° C. for three hours. The lower graph is an expanded scale for times immediately after the upper graph. The specific conditions of the signal were: a $T_1$ of 4.5 seconds, $T_2$ of 15 minutes, T of 68 µs, N of 6,800, and a pulse energy of 104 µJ. As can be seen from the data shown in FIG. 18 (as time progresses from the top graph in the figure through the bottom graph in the figure), the resistance stabilizes and does not systematically fluctuate during the 15-minute intervals between the measurement points. This demonstrates that the water vapor continues to diffuse out of the active layer and surrounding regions, and does not diffuse back in when the pulse train is off for as long as 15 minutes.

Of primary concern in this example is the average energy required by the pulse clearing technology to keep the active layer and regions below the active layer dry. Since the pulses are only 68 µs long and there are 6,800 per 15-minute interval, each with an energy of 104 µJ, the average power can be calculated as 0.8 mW. This corresponds to a maximum average current required by the pulse clearing technology to keep the sensor dry of about 100.0 µA. At these low current levels, an AA battery could supply enough energy to keep the sensors dry for 10,000 hours. This low energy requirement is a reflection of the very thin region that is being heated, but can effectively block water diffusion.

Example 4

Temperature Control within a Pulse-Cleared Device

Figure 19:
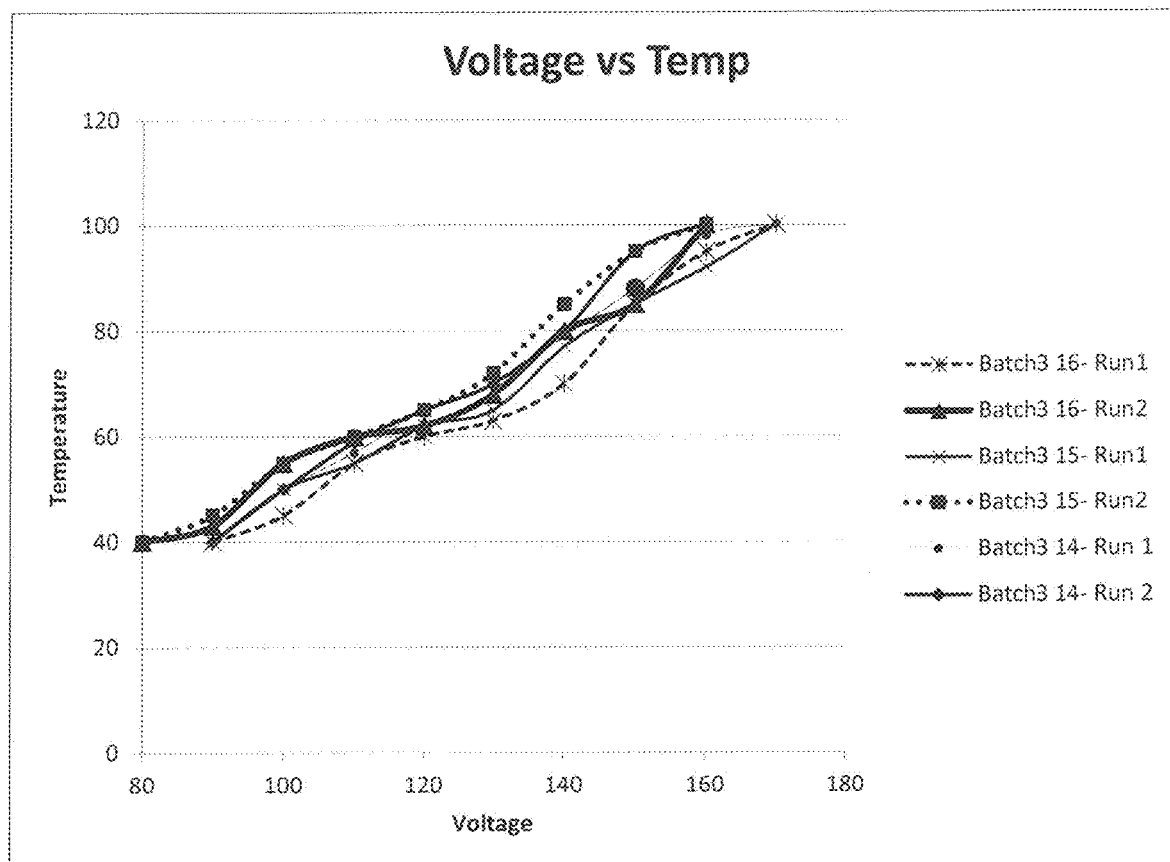
FIG. 19 is a graph depicting the surface temperature obtained as a function of peak pulse voltage during the pulse clearing described in Example 4.

The sensors fabricated in Example 1 (all chosen to be in the range of 60 kΩ) were mounted to a thermally isolated structure in air, and were pulsed with varying energy and the temperature of the active layer was measured with a IR camera (Fluke Model TiR3) calibrated to read temperatures up to 100° C. The camera was positioned about 50 cm from the front surface of the sample. The temperature of the front surface was measured by placing the measurement cursor on the IR camera display over the image of the front surface. As the temperature of the sensor surface increased during the pulse train, and, reached equilibrium after about 2.0 seconds, the camera (sampling refresh rate of 133 ms) measured the maximum temperature. For this example, the following conditions were used: a $T_1$ of 4.5 seconds, $T_2$ of 15 minutes, τ of 68 µs, and a N of 6,800. The energy of each pulse was varied by varying the peak voltage, $V_p$, during the pulse so energy was calculated as $V_p^2/R_{meas}$. In FIG. 19, the temperature obtained on the surface of the sensor as a result of the pulse clearing is plotted against the peak pulse voltage, $V_p$. Variation in $V_p$ among these patches is a result of $R_{meas}$ variation. The graph clearly shows that the temperature and thus type of volatile forced from the active layer can be controlled by controlling the peak pulse energy. This technology will enable selective determination of the volatile in the external sample environment.

Figure 20:
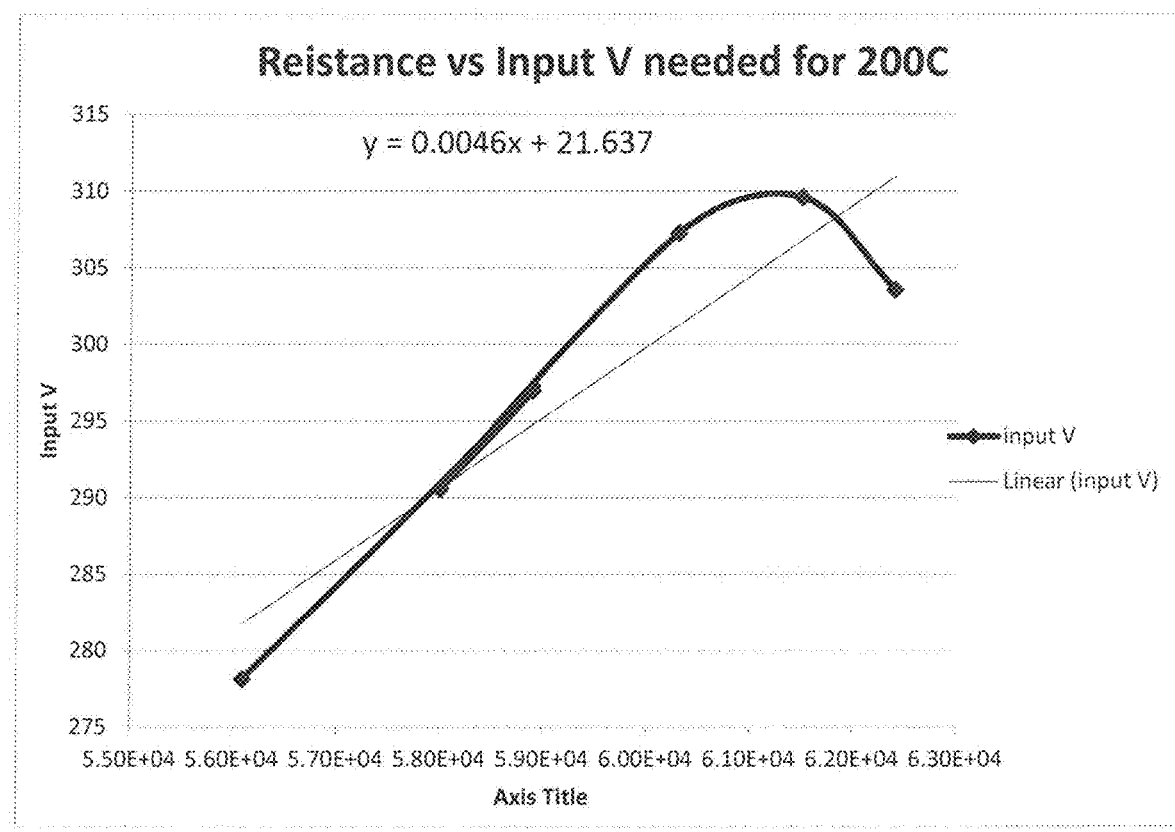
FIG. 20 is a graph showing the peak pulse voltage needed to reach 200° C. on the surface of the sample described in Example 4 as a function of $R_{meas}$ (horizontal axis)

FIG. 20 shows the $R_{meas}$ and the $V_p$ required to consistently produce a temperature of about 200° C. This final temperature is based on the linear nature of the convective heat transfer process dominant in this temperature realm and a linear extrapolation of the measured data to 100° C. on the surface of a sensor fabricated in Example 1. The voltage required to reach 200° C. increases linearly with the resistance of the sensor from a combination of the resistance decreasing exponentially with temperature and the power going up with the square of voltage for resistances below about 61 kOhms. For resistances above 61 kOhms, the voltage level plateaus and decreases, since at this combination of voltage and resistance (and corresponding electric fields) additional carriers are forced from the conducting grains in the active layer onto the insulating regions referred to as a carrier avalanche effect. For comparison purposes, a linear response throughout the region is shown by the black line.

Example 5

High Temperatures Using Pulse Heating

Figure 21:
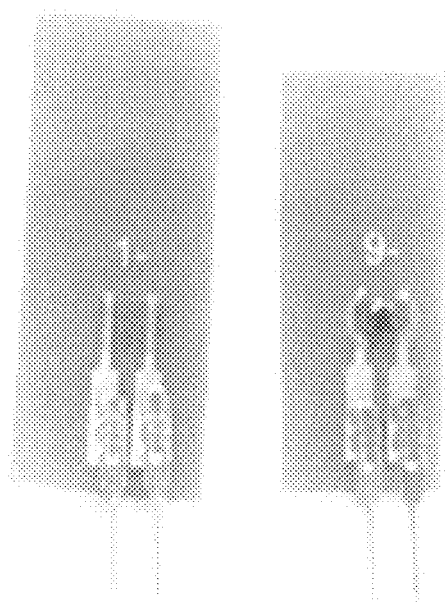
FIG. 21 is a photograph of the pyrolyzed sensor (left) and the unpyrolyzed sensor (right) of Example 5.

Pulse heating was used to produce very high temperatures on the surface of the sensors fabricated in Example 1. At pulse conditions of $T_1$ of 4.5 seconds, $T_2$ of 20 minutes, τ of 68 µs, and a N of 9,067, with pulse peak voltages of $1.01 \times R_0$ (where $R_0$ was the initial room temperature resistance of the devices), the SOC material was decomposed at approximately 250° C. The Kapton® film substrate 12 was pyrolyzed at approximately 600° C. using pulse conditions of $T_1$ of 4.5 seconds, $T_2$ of 20 minutes, τ of 68 µs, and a N of 9,067 with peak pulse voltages of about $1.35 \times R_0$. For example, a device with a room temperature resistance of 281 kOhms pyrolyzed at 380 Volts. Below pyrolyzation temperatures, the CNT active layer of the sample is undamaged and does not show significant changes in room temperature resistance. FIG. 21 shows an image of the pyrolyzed sensor.

Example 6

Fabrication of a Cnt/Palladium Gas Sensing Device

A device was fabricated as shown in FIGS. 10a, 10b, and 10c on a Melinex® ST730 PET substrate 12. Silver electrodes 14, 16 were then screen printed, using AG-800 silver conductive ink (Conductive Compounds), (screen printer model: AT-60PD, screen: polyester, 230 threads/inch, flood/squeegee speed: 225 mm/s, flood bar pressure: 10 µsi, squeegee pressure: 25 µsi) onto the substrate 12 and cured in the conveyor oven at 130° C. at a 10"/min speed. The cured Ag electrodes 14, 16 had a thickness of 5 µm. A CNT active sensing layer 18 (Brewer Science, Inc., Rolla, Mo.) was spray coated across the electrodes 14, 16 using the following parameters: platen temperature: 135° C., scan width: 2 mm, flow rate: 10 ml/hr, scan speed: 60 mm/s, spray head: Sono-Tek, model: 048-00214) using 3 passes across the electrode region. An insulating palladium layer was then DC sputtered on the surface at a pressure of about 120 mTorr and plasma current of around 30 mA for 350 seconds. The thickness of the palladium layer is a function of the sputter time and was adjusted so that the atomic or molecular morphology was that of a clusters or islands that were non-electrically conducting. 32 devices were fabricated in this manner.

Example 7

Fabrication of 4-Pixel Gas Sensor

Figure 22:
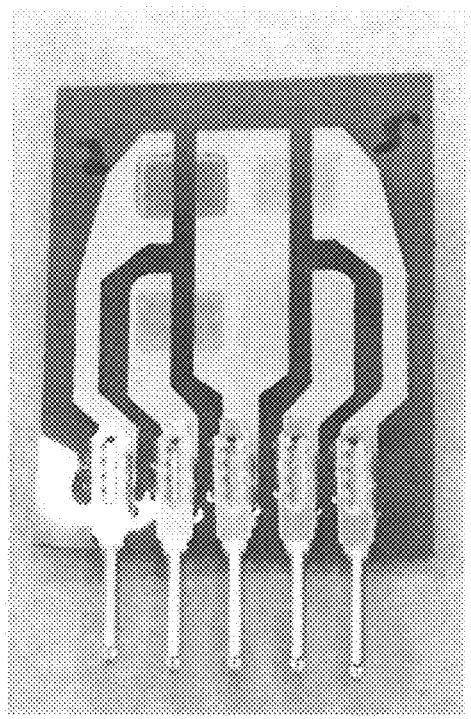
FIG. 22 is a photograph of the four-pixel printed electronic device fabricated in Example 7.

Sensors were fabricated according to four-pixel device diagram shown in FIG. 2. Each of the four rectangles is a CNT-based "pixel", while the other five shapes are electrodes. A picture of the four-pixel device is shown in FIG. 22.

The four pixels were identical in composition and were formed from a CNT ink functionalized with $SnO_2$. An oven dried three-neck flask equipped with a dried reflux condenser under nitrogen and a dried addition funnel were placed in an oil bath. 20 milliliters of anhydrous 1,3-butanediol (Sigma Aldrich product number: 309443, Lot# SHBG0918V) were placed in the addition funnel and added to the flask and were stirred at 350 rpm. Then, 2.5 milliliters (0.00070411 mol) of tin(IV) isopropoxide (10% in IPA/toluene, Sigma Aldrich product number: 760153, MW=355.06) were placed into the reaction flask via syringe. This was heated to 100° C. in the oil bath. The solution was not cloudy, indicating that the $SnO_2$ had not formed. Twenty-five milliliters of functionalized Tubal carbon nanotubes (Brewer Science, Inc., Rolla, Mo., optical density at 550 nm=47.8) dispersed in 2-methyl-1,3-propanediol (Sigma Aldrich, St. Louis, Mo., product number 375721) were added to the flask through one of the side arms.

After reacting for 30 minutes, the temperature was set to 200° C. and a timer set to 1200 minutes. After 1200 minutes, the reaction turned off and cooled to room temperature. This ink was collected and printed without further processing.

The silver electrodes of four pixels of the device shown in FIG. 2 were printed using an ATMA AT-60PD screen printer on a Kapton® substrate 12 and thermally cured prior to the pixel screen print procedure. The $SnO_2$-coated carbon nanotube ink was screen printed on top of the silver electrodes. The squeegee speed was set to 125 mm/s. A 123-70 PET mesh screen was used with an 8 μm emulsion (E80 supplied by Sefar, Inc.). The ink was dried in a conveyor oven at 280° F., with the belt run at 46 in/min. No encapsulation layer was printed on the surface of the pixels.

The resistances of the pixels were measured one day after device synthesis process and are shown in Table 1. The table shows the resistances of each four-pixel device in kOhms after the screen printing process. Each device on the substrate 12 is identified by a [row]-[column] nomenclature on the top. The four values below are the individual pixel resistances.

After the four-pixel devices were characterized, a palladium metal physical vapor deposition (PVD) process was performed to produce palladium metal islands over the $SnO_2$-functionalized CNT screen printed layer of each pixel. 5 Å of palladium was e-beam deposited on the surface of the pixels, one sheet at a time. This process was performed by Center for Applied Science and Engineering at the JVIC facility. After this palladium PVD process, the individual pixel resistances were measured again. Table 2 shows the resistances after the palladium deposition.

TABLE 2

Resistance of 4-pixel devices after palladium deposition

| 1-1 | | 1-2 | | 1-3 | | 1-4 | | 1-5 | |
|---|---|---|---|---|---|---|---|---|---|
| 4.059 | 5.125 | 8.17 | 8.82 | 7.07 | 15.15 | 2.98 | 3.39 | 4.43 | 3.95 |
| 4.36 | 9.38 | 6.44 | 7.51 | 6.09 | 5.78 | 3.62 | 3.19 | 3.79 | 3.98 |
| 2-1 | | 2-2 | | 2-3 | | 2-4 | | 2-5 | |
| 2.31 | 2.78 | 6.82 | 7.31 | 10.42 | 3.93 | 8.33 | 13.13 | 2.59 | 2.05 |
| 2.39 | 2.7 | 4.08 | 3.92 | 8.8 | 8.61 | 5.62 | 3.68 | 3.35 | 2.49 |
| 3-1 | | 3-2 | | 3-3 | | 3-4 | | 3-5 | |
| 2.7 | 2.6 | 2.77 | 3.43 | 4.19 | 3.56 | 4.02 | 4.4 | 5.13 | 2.72 |
| 2.7 | 2.73 | 3.13 | 3.35 | 2.8 | 2.94 | 3.39 | 3.61 | 2.98 | 3.62 |

After the four-pixel devices were characterized, a palladium metal physical vapor deposition (PVD) process was performed to produce palladium metal islands over the $SnO_2$-functionalized CNT screen printed layer of each pixel. 5 Å of palladium was e-beam deposited on the surface of the pixels, one sheet at a time. This process was performed by Center for Applied Science and Engineering at the JVIC facility. After this palladium PVD process, the individual pixel resistances were measured again. Table 2 shows the resistances after the palladium deposition.

TABLE 2

Resistance of 4-pixel devices after palladium deposition

| 1-1 | | 1-2 | | 1-3 | | 1-4 | | 1-5 | |
|---|---|---|---|---|---|---|---|---|---|
| 4.059 | 5.125 | 8.17 | 8.82 | 7.07 | 15.15 | 2.98 | 3.39 | 4.43 | 3.95 |
| 4.36 | 9.38 | 6.44 | 7.51 | 6.09 | 5.78 | 3.62 | 3.19 | 3.79 | 3.98 |
| 2-1 | | 2-2 | | 2-3 | | 2-4 | | 2-5 | |
| 2.31 | 2.78 | 6.82 | 7.31 | 10.42 | 3.93 | 8.33 | 13.13 | 2.59 | 2.05 |
| 2.39 | 2.7 | 4.08 | 3.92 | 8.8 | 8.61 | 5.62 | 3.68 | 3.35 | 2.49 |
| 3-1 | | 3-2 | | 3-3 | | 3-4 | | 3-5 | |
| 2.7 | 2.6 | 2.77 | 3.43 | 4.19 | 3.56 | 4.02 | 4.4 | 5.13 | 2.72 |
| 2.7 | 2.73 | 3.13 | 3.35 | 2.8 | 2.94 | 3.39 | 3.61 | 2.98 | 3.62 |

Example 8

Assembly of Bench for Trace Gas Testing

Figure 23:
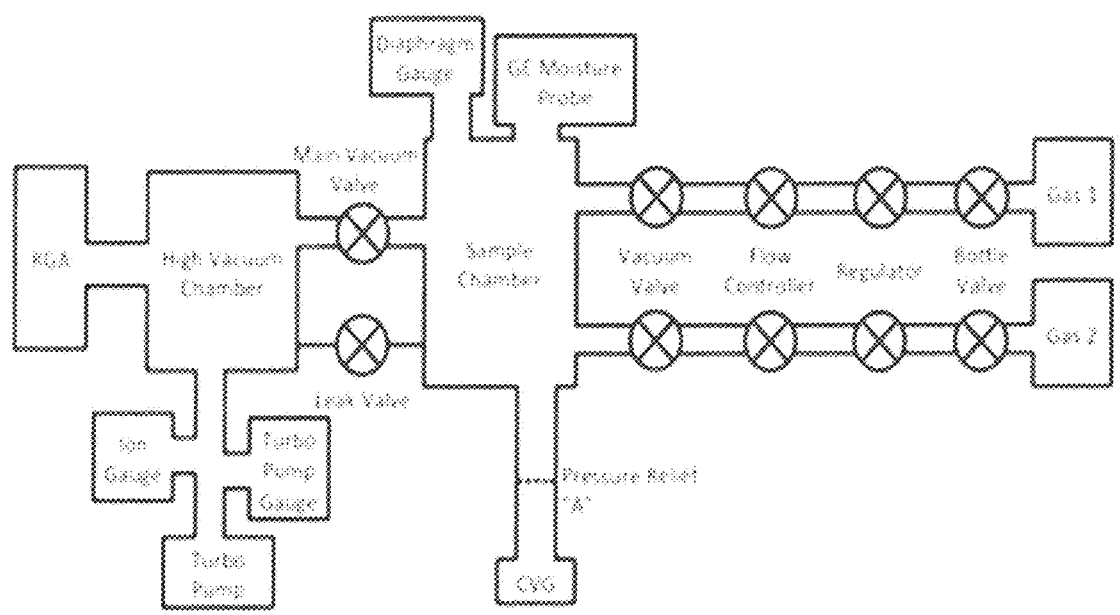
FIG. 23 is a gas test bench block diagram of the gas test bench used in Example 8.

A trace gas test bench was constructed as shown by the block diagram in FIG. 23.

The sensor under test is mounted with electrical vacuum feedthrough connections in the Sample Chamber. Before testing, the Sample Chamber is evacuated to less than 100 mTorr, as measured by the convection gauge (CVG), by opening the Main Vacuum Valve and turning on the Turbo Pump. The Vacuum Valves that control the gas inlets to the sample chamber are also turned on to evacuate the lines running from the gas Flow Controllers to the Sample Chamber. The Bottle Valves for the gases are opened and the regulator is set for standard room pressure. Gas 1 is connected to room air, and, Gas 2 is connected to the gas under test. The pressure in the sample chamber during testing is held slightly below normal room pressure (760 Torr), at 600 Torr. A safety pressure relief value releases slightly 740 Torr at "A" in FIG. 23. This valve has a very large throughput to the Sample Chamber, so contents are immediately vented if activated.

The MKS Type 1179A and 2179A Mass-Flo® controllers working with two MKS Type 179A Mass-Flo Meters are used to precisely measure the amount of gas that flows into the sample chamber. These meters are factory calibrated to $N_2$ gas, and gauge correction factors can be used to convert these numbers into flow rates for other gases. For example, the gauge factor for $N_2$ is defined as 1.00. For example, when using hydrogen, the gauge factor must be calculated from the specific heat, density, and diatomic nature of hydrogen. Using these numbers, the gauge factor for hydrogen is 1.011. The gauge factor is multiplied by the readout on the Gas 2 Mass-Flo Meter to determine the actual hydrogen flow rate into the Sample Chamber.

The total volume of the Sample Chamber was precisely determined by introducing STP $N_2$ flowing at a rate of 10.0 SCCM (STP cubic cm per minute) into the Sample Chamber at a constant temperature and measuring the total pressure using the Diaphragm Gauge. The Diaphragm Gauge is an Omega Model DPG8001 with a displayed precision of 0.1 Torr and a range of 5 to 1000 Torr. The mass (or number of moles) of gas that have flowed into the Sample Chamber as a function of time can be calculated by using the 179A Mass-Flo Meter, the molar volume at STP (22.4 L/mole), and, the molecular weight of the gas. If the number of moles flowing into the Sample Chamber as a function of time is plotted against the pressure in the Sample Chamber as a function of time, the result is a very nearly linear graph (ideal gas law) where the slope is proportional to the total volume of the Sample Chamber. Using the ideal gas constant, and the constant background temperature, the total volume of the Sample Chamber was determined to be 942.4 $cm^3$.

After the Sample Chamber containing the test sensor is evacuated, the Main Vacuum Valve is closed, and room air flows into the system through the Flow Controller at Gas 1. The room air Flow Controller is turned off when the total pressure in the Sample Chamber as read by the Diaphragm Gauge is 600 Torr. This is the background air that is required for the operation of the solid-state metal/metal oxide detection process to work.

After background signals have been established, the test gas flows into the system at a rate determined by the Gas 2 flow controller. The precise amount of test gas introduced into the Sample Chamber is determined by the flow rate set on the controller, the gauge factor, and the amount of time the flow controller is on. These parameters are set by the details of the specific experiment. The sensor response is relative to the background signal before the test gas flow controller is turned on.

In this mode of operation, the system is a gas mixing chamber, rather than a gas flow chamber. It can also be used as a gas flow chamber if the Leak Valve is opened and the gases flow through the system past the test sensor. In the gas mixing mode of operation, the test gas must diffuse from the gas input lines to the test sensor which takes a period of time (diffusion time).

Example 9

Testing of Pixel Temperature

Figure 24A:
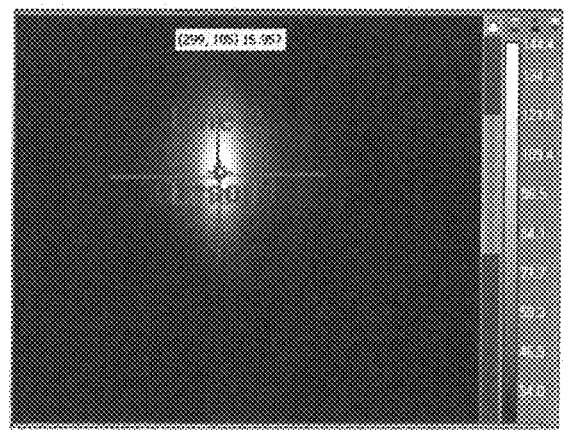
FIG. 24a is a FLIR camera photograph showing the $SNO_2$/palladium single pixel oriented with the electrodes in the x-direction that was activated in Example 9.
Figure 24B:
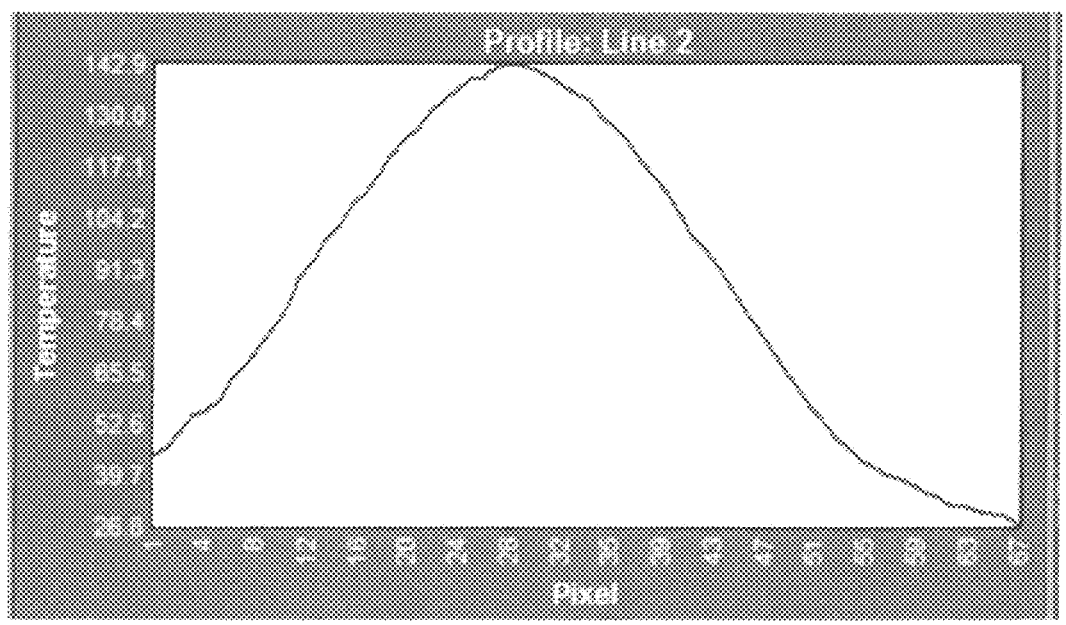
FIG. 24b is a graph showing the temperature measured by a FLIR camera showing the temperature profile in the x direction of the single pixel of FIG. 24a during a heating pulse train cycle.
Figure 24C:
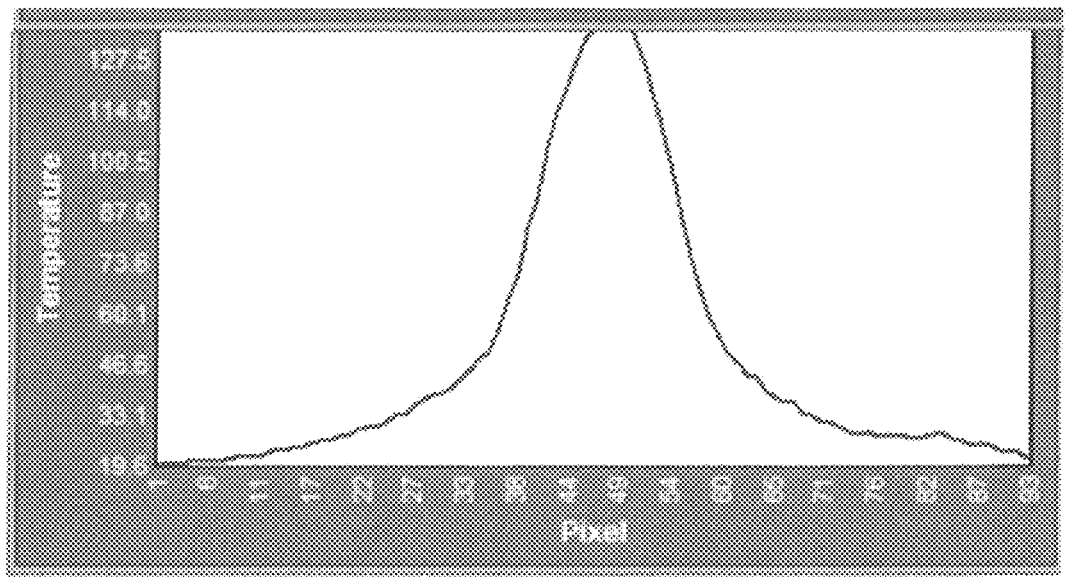
FIG. 24c is a graph showing the temperature measured by a FLIR camera showing the temperature profile in the y direction of the single pixel of FIG. 24a during a heating pulse train cycle.
Figure 24D:
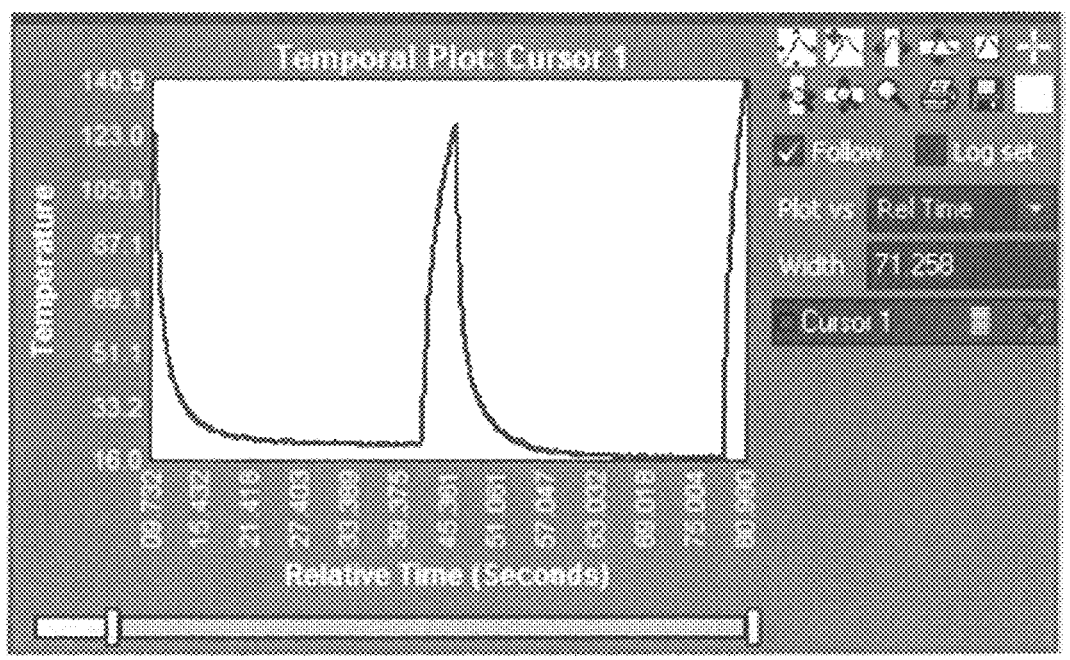
FIG. 24d is a graph showing the temperature versus time as measured by a FLIR camera showing the longer-term cycling of the single pixel of FIG. 24a, as described in Example 9.

A FLIR Camera Model AX5 was used to measure the temperatures generated within the individual pixels during the heating of the active sensing layer 18 as a result of the pulse train. The camera was positioned 5 cm from the surface of a $SNO_2$/palladium four-pixel device as fabricated in Example 7. Camera settings included a frame refresh rate of 30 Hz and a low input bandpass setting to measure temperatures above 100° C. Only one of the four pixels was activated; whose image is shown in FIG. 24a. In FIG. 24a, the pixel is shown as the white (or hot) regions behind the horizontal and vertical lines. The horizontal and vertical lines represent the temperature profiles in the x and y directions, respectively, within the pixel during a heating pulse train cycle. These temperature profiles are shown in FIGS. 24b (x direction) and 24c (y direction). The profile indicates a typical Gaussian distribution of temperature with the center of the pixel reaching the highest temperature. For this test, the pulse train parameters were a pulse width of 68 μs, a repetition rate of 500 Hz, and a constant peak pulse voltage of 100 V.

This pulse train heated the active sensing layer 18 of the pixel for a period of 4.4 seconds. After an additional 30 seconds, where the pixel was allowed to cool, the pulse train was again used to heat the pixel for 4.4 seconds. This pattern was repeated for the duration of the experiment. The results for one heating pulse train are shown in FIG. 24. This longer-term cycling can be seen in FIG. 24d, with the heat pulses repeating every 30 seconds. It should be noted that the FLIR camera measures the surface temperature of the pixel, the micro- and nano-regions where the heat is being generated may be much hotter.

Figure 25:
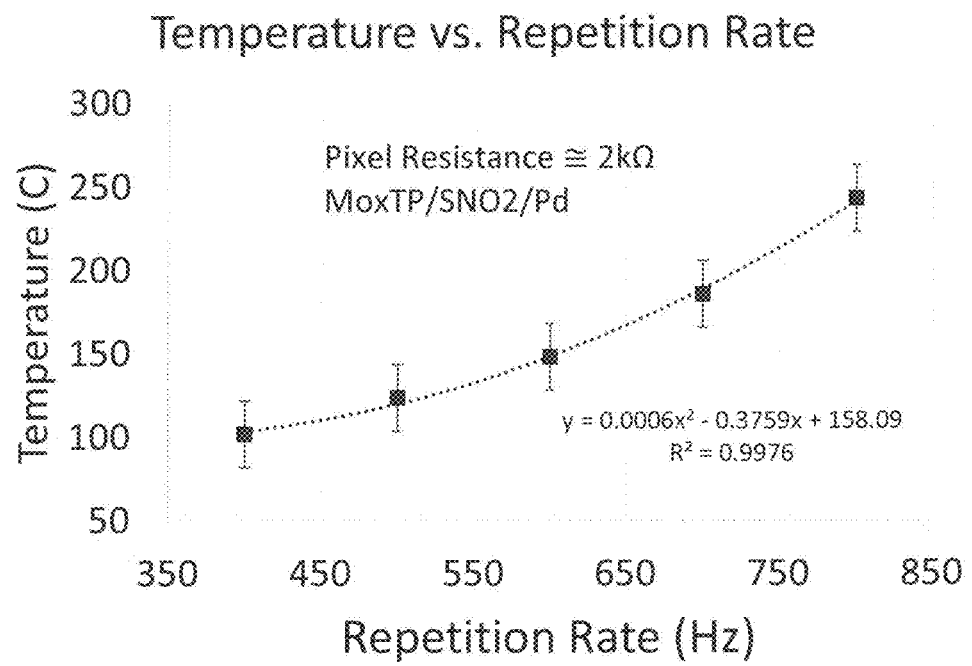
FIG. 25 is a graph depicting the temperature vs. repetition rate for pixels of two different resistances as described in Example 9.
Figure 25:
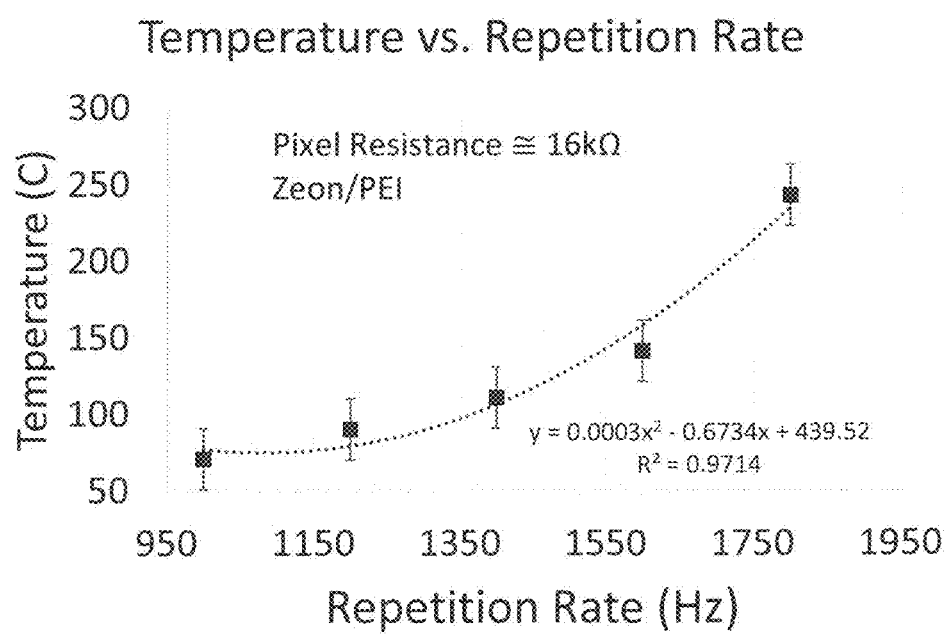

The average pixel temperature (measure by the FLIR camera) as a function of pixel resistance and repetition rate is shown in FIG. 25. Higher repetition rates are required by pixels with a higher resistance to achieve the same temperatures. This is a result of the lower currents at 100 V when the pixel resistance is higher. In all cases the pulse width was fixed at 68 μs. The power fit shown in the figure is indicative of the power law ohmic heating process.

Figure 26:
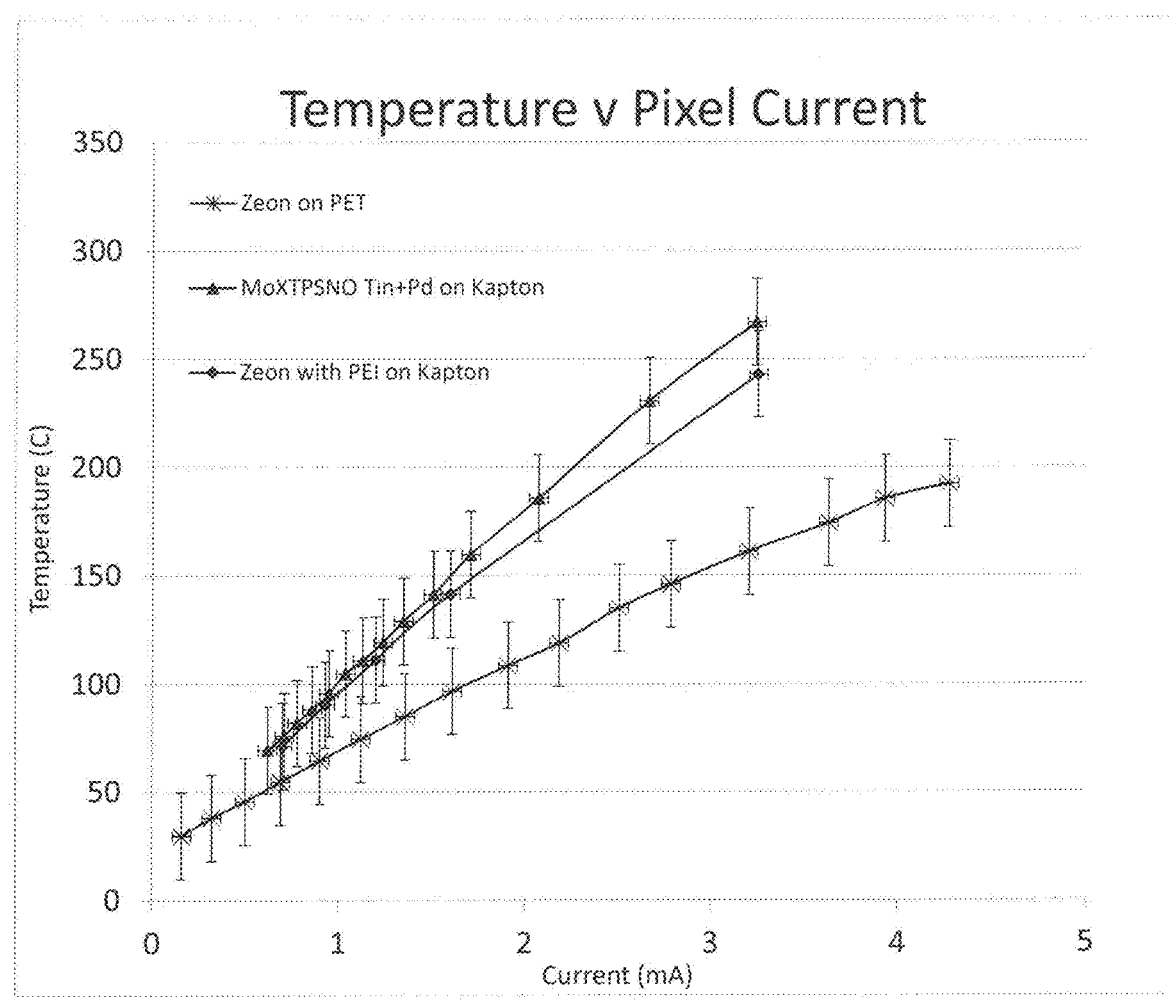
FIG. 26 is a graph illustrating the variation of pixel temperature with current through the pixel as described in Example 9.

FIG. 26 shows the temperature of the pixels for different pixel compositions and average pixel current during the pulse train. The graph eliminates the temperature dependence of the pixels on the pixel resistance, however pixel current is a more difficult parameter to control during the pulse train compared to repetition rate. In order to fix a pixel average current, the voltage would need to be varied.

Example 10

Hydrogen Testing with Pulsed Electronics

Figure 27:
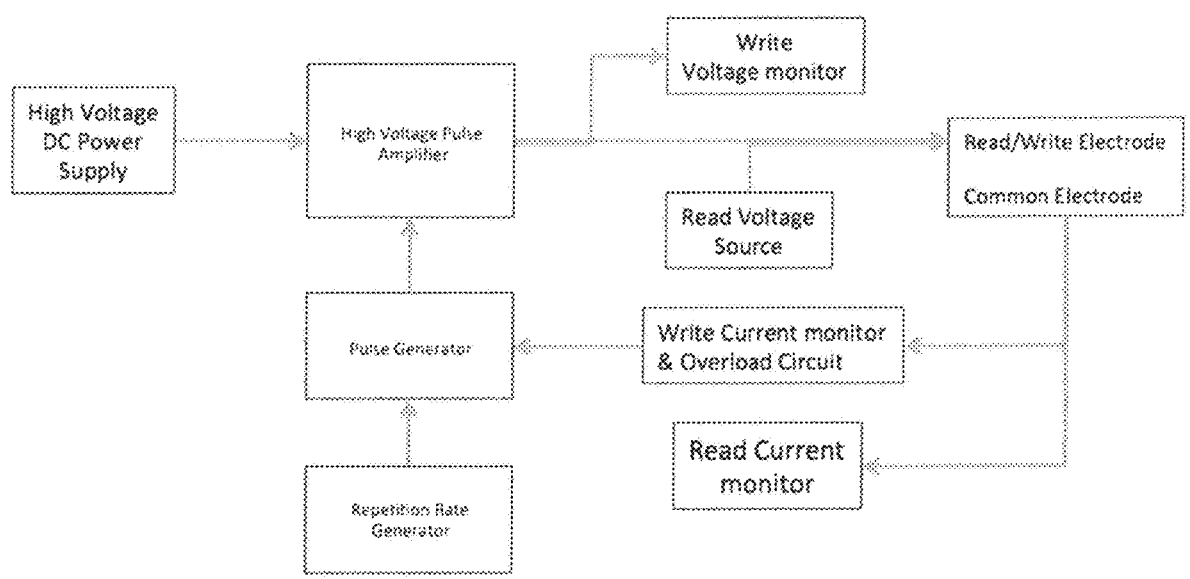
FIG. 27 shows the test setup followed in Example 10.

The test sensor fabricated in Example 6 was mounted and tested in the system described in Example 8 using the gas mixing mode of operation. The sample was tested using the circuit shown in FIG. 27 with variable electronic current pulse train parameters of a pulse width of 70 μs, a repetition rate of 625 Hz, and a constant peak pulse voltage of 100 V.

Figure 28:
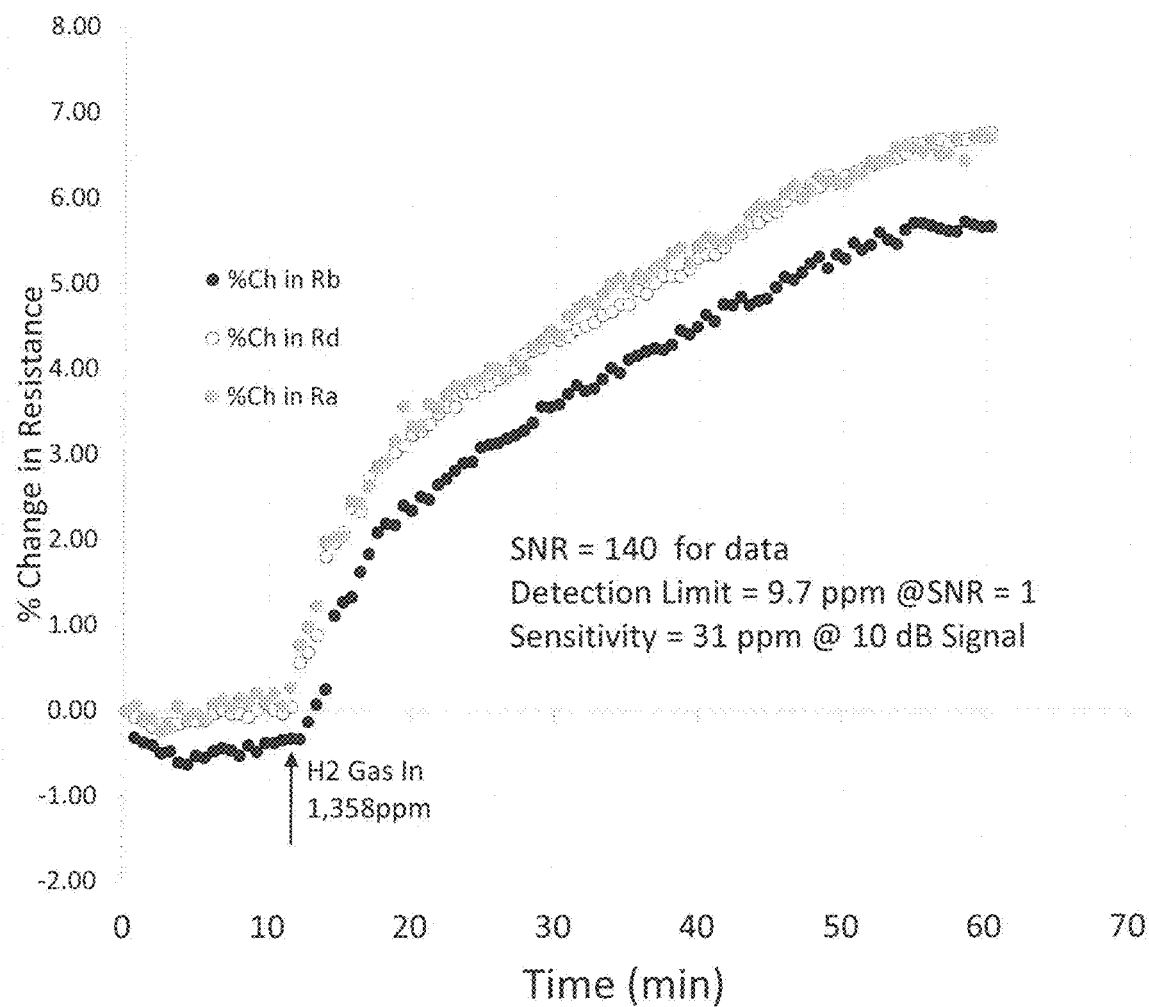
FIG. 28 is a graph showing the signal response as % resistance change over time for the sensor device tested in Example 10.

This pulse train heated the active sensing layer 18 in the pixel for a period of 4.4 seconds. The pixel was then allowed to cool for 30 seconds, after which the pulse train was again used to heat the pixel for 4.4 seconds. This pattern was repeated for the duration of the experiment. At an elapsed time of 11:30 minutes (as shown by the blue arrow in FIG. 28) the hydrogen flow controller was turned on for 20 seconds with a setting of 3.0 SCCM. Using the volume of the chamber (determined in Example 8), the ratio of the mass of the hydrogen introduced into the Sample Chamber to the mass of air inside the chamber was calculated to be 1,358 ppm. As shown in the figure, the sensor picked up the trace hydrogen signal immediately and the sensor signal continued to rise as the hydrogen gas diffused from the inlet to the sensor within the chamber. In FIG. 28, each point represents a 3-second heating cycle. Rb is the signal before heating, Rd is the signal during heating and Ra is the signal after heating.

Figure 29:
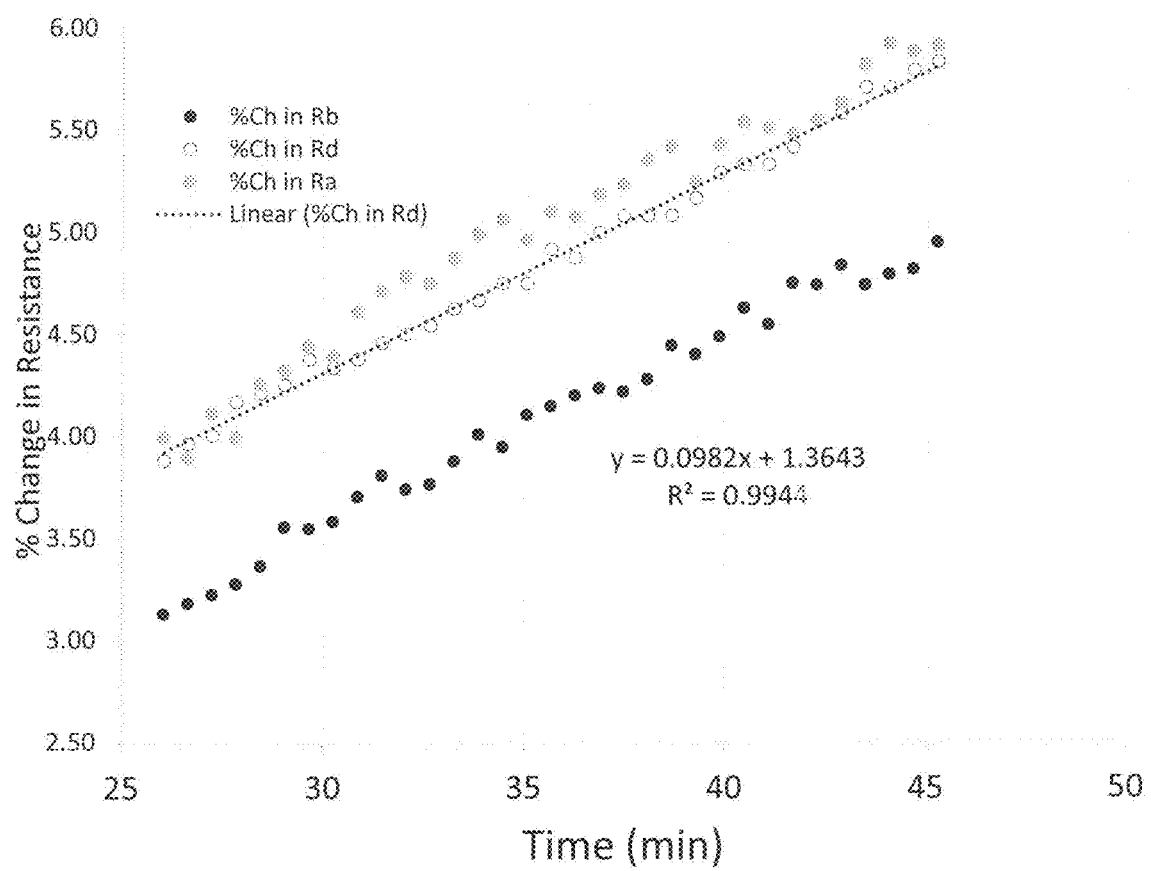
FIG. 29 is a graph illustrating how, in the region where the signal was a result of the diffusion of hydrogen gas to the sensor, the sensor response slowly varied (Example 10)

The sensitivity of the sensor can be determined by the ratio of the observed signal compared to the fluctuating noise, or the signal-to-noise ratio (SNR). The SNR for the sensor was determined using the data shown in a linear region of FIG. 28, which is shown in FIG. 29. From the graph, the noise can be calculated from the average fluctuations about a linear best fit to the data, as shown by the dashed line in FIG. 29, and the signal can be calculated from the high and low limits of the line. Using this method, the SNR for this sensor is 140. At a SNR of 1.0, the signal is equal to the noise, and therefore, at the detection limit of the sensor. This implies the sensor is at its detection limit with a signal of 9.7 ppm hydrogen. However, to register a good SNR, normally a signal of 10 dB over the noise is desired. For a 10-dB SNR (i.e. more signal than noise) the sensor device used in this example would require a hydrogen concentration of 31 ppm.

This example demonstrates that at maximum concentrations of hydrogen of 1,338 ppm, and the pulse heat parameters set above, the sensor theoretically can detect hydrogen trace gas concentrations of 31 ppm at a SNR of 10 dB.

Example 11

Hydrogen Testing with Pulsed Electronics and Higher Pixel Temperature

The test sensor fabricated in Example 6 was mounted and tested in the system described in Example 8 using the gas mixing mode of operation. The sample was tested in the same manner as in Example 10, but with variable electronic current pulse train parameters of a pulse width of 70 µs, a repetition rate of 800 Hz, and a constant peak pulse voltage of 100 V.

As in Example 10, this electronic pulse train heated the active sensing layer 18 within the pixel for a period of 3.0 seconds. After an additional 30 seconds where pixel was allowed to cool, the pulse train was again used to heat the pixel for 3.0 seconds and this pattern was repeated throughout the experiment. The pulse repetition rate is the parameter that determines the final temperature of the pixel. As the repetition rate increases, the current duty cycle increases (provided the pulse width remains the same), creating a larger average current within the active sensing layer 18 heater. This larger current flow produces more heat dissipation within the active sensing layer 18, and results in a higher temperature after the same 3-second pulse train period.

Figure 30:
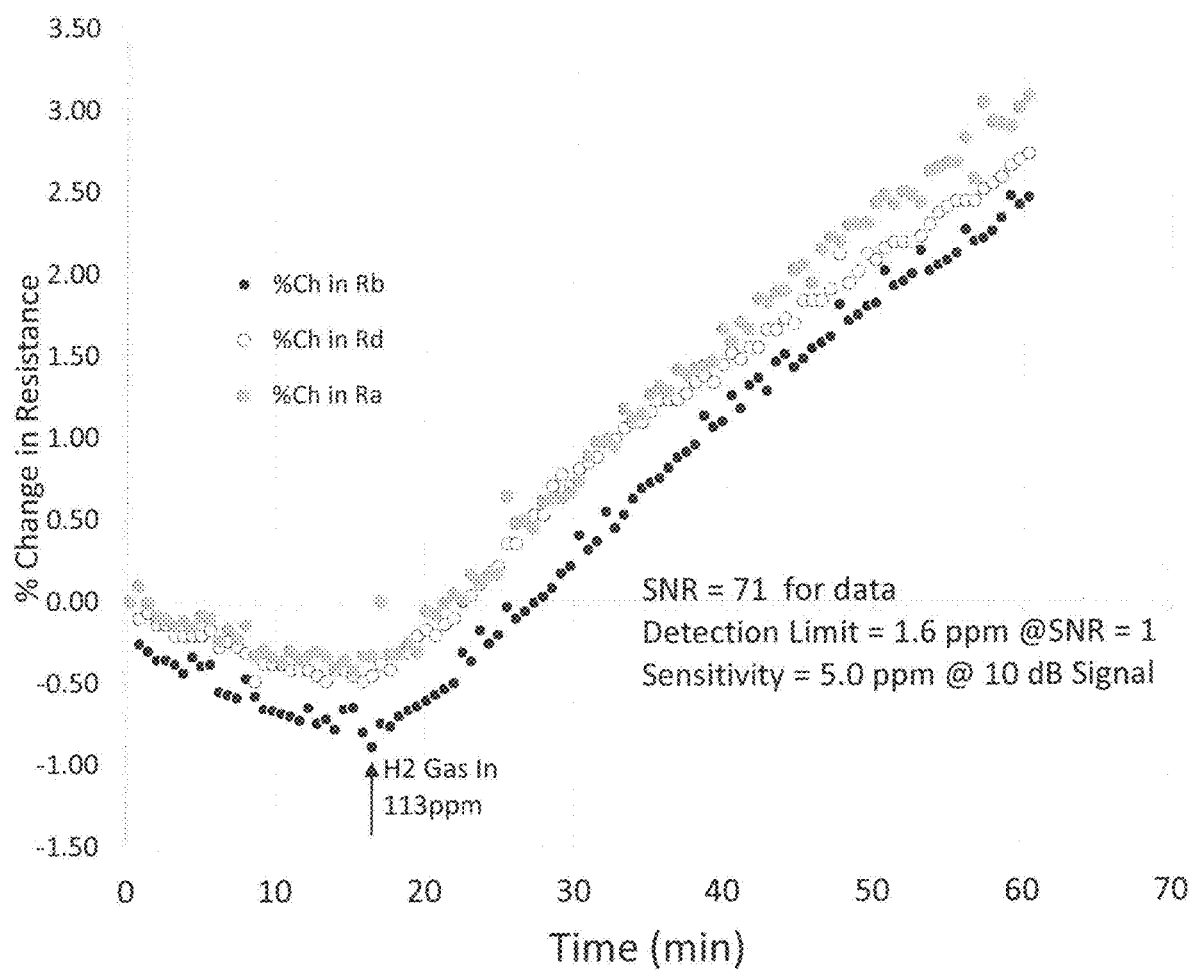
FIG. 30 is a graph showing the signal response as % resistance change over time for the sensor device tested in Example 11.

The results of this experiment are shown in FIG. 30. At this higher pixel temperature, the sensor device was more sensitive to hydrogen trace concentrations. At an elapsed time of 16:30 minutes, a signal of only 113 ppm of hydrogen was introduced into the Sample Chamber. The sensor device responded with a detection limit of 1.6 ppm, and, a 10 dB signal of 5.0 ppm. The signal level continued to increase as the hydrogen in the inlet diffused to the sensor. At 800 Hz, the device operated in a much more sensitive way than when operated at 625 Hz (Example 3) where the 10 dB signal was 31 ppm. In FIG. 30, each point represents a 3-second heating cycle. Rb is the signal before heating, Rd is the signal during heating and Ra is the signal after heating.

In terms of hydrogen gas specificity or selectivity, one pixel of the device shown in FIG. 2 could run at 625 Hz, and another could run at 800 Hz. As a result, each of the pixels would be at different final temperatures after the 3-second pulse train. As shown in this example and Example 10, this would result in different signals as a result of the different sensitivities of the pixels (5 ppm, 31 ppm respectively). Therefore, with these two pixels, the slope of the unique palladium metal cluster absorption of hydrogen as a function of temperature can be determined, making the device much more hydrogen gas specific than current single-temperature/single-pixel devices.

Example 12

Testing of 4-Pixel Gas Sensor with Carbon Monoxide

In this example, the pulse-heated sensitivity to carbon monoxide of the CNT/$SNO_2$/palladium device fabricated in Example 7 was measured. The performance of this device was determined in the same way as described in Example 10 to measure the change in resistance of the active sensing layer 18 before, during, and after the pulse train, but with variable electronic current pulse train parameters of a pulse width of 70 µs, a repetition rate of 400 Hz, and a constant peak pulse voltage of 100 V.

This electronic pulse train heated the active sensing layer 18 within the pixel for a period of 4.4 seconds. The pixel was then allowed to cool for 30 seconds, and the pulse train was again used to heat the pixel for 4.4 seconds. This pattern was repeated throughout the experiment. In this example, the pulse repetition rate was set to 400 Hz as a result of a smaller 3 k$\Omega$ pixel impedance. The temperature of the pixel during testing was approximately 122° C.

Figure 31:
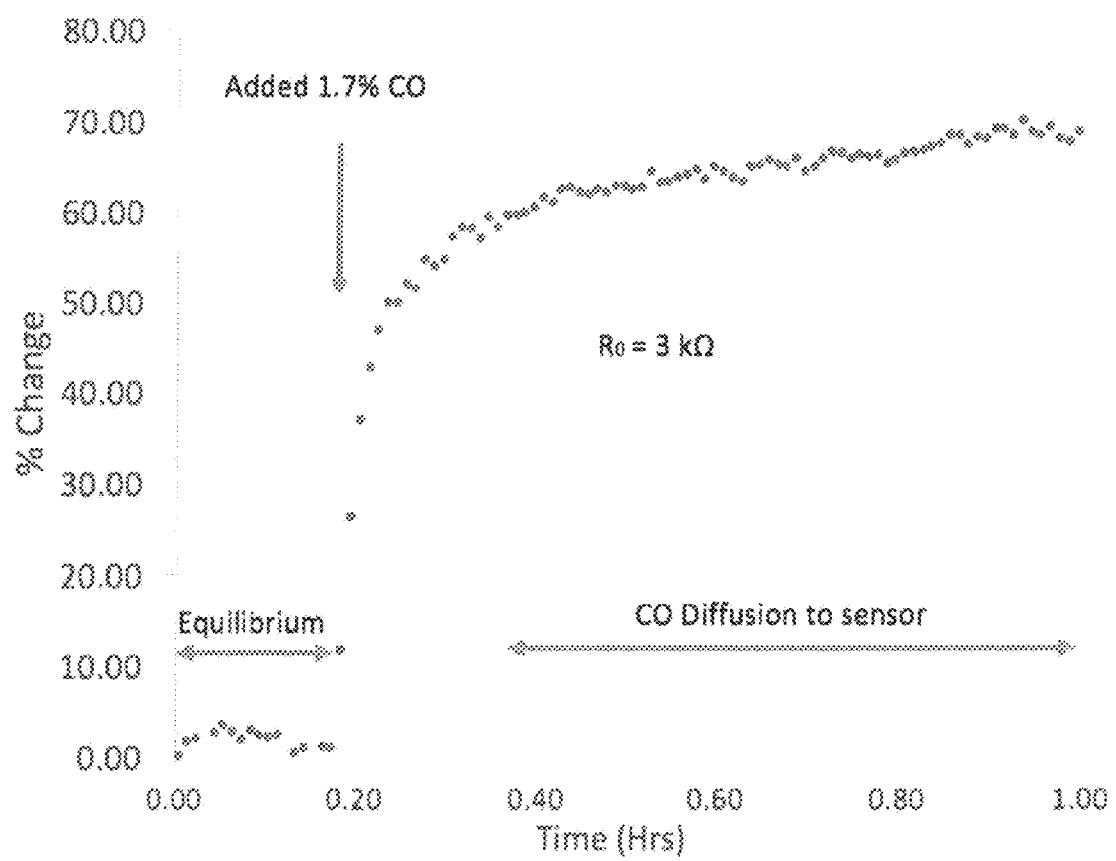
FIG. 31 is a graph depicting the results of Example 12, where a $CNT/SNO_2$/palladium device was exposed to CO (400 Hz)
Figure 32:
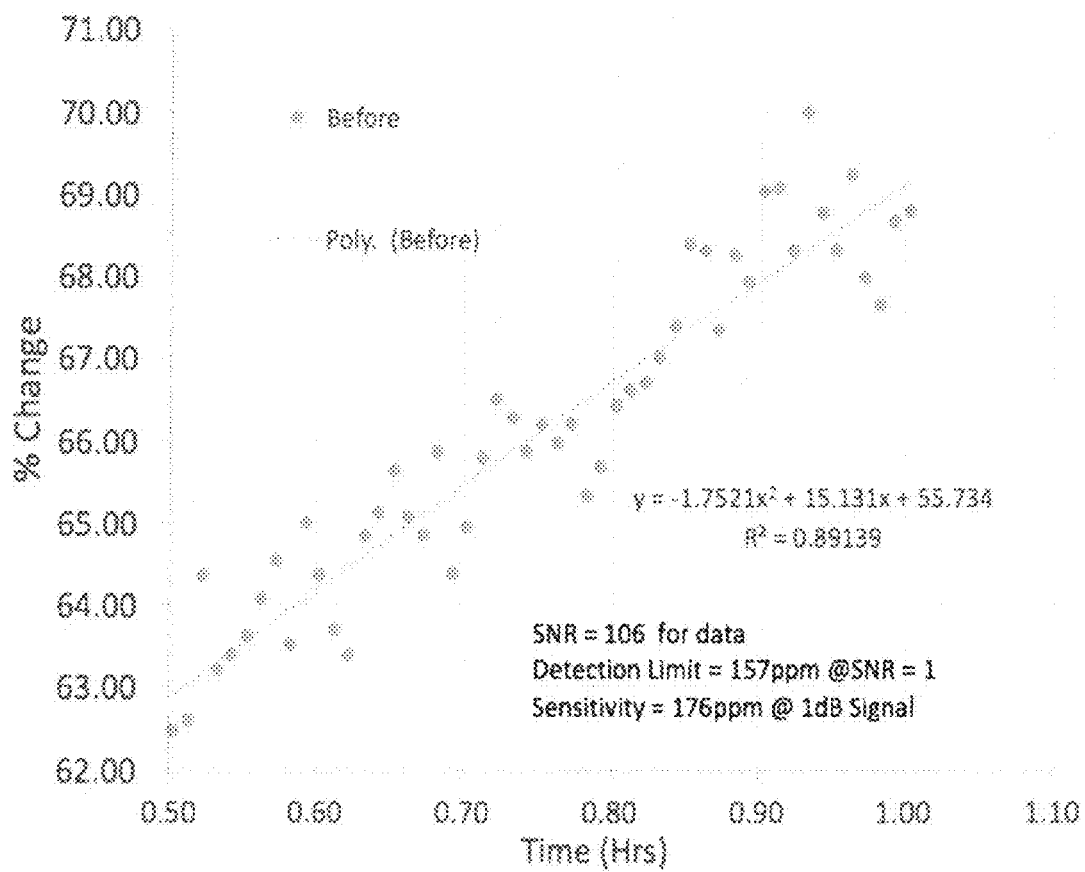
FIG. 32 is a graph of the signal-to-noise ratio analysis carried out in Example 12 to demonstrate the sensitivity of the device to CO gas concentration (400 Hz)

The results of this example experiment are shown in FIGS. 31 and 32. At an elapsed time of 11:30 minutes, a signal of 1.7% CO was introduced into the Sample Chamber. The sensor device responded with a detection limit of 156 ppm, and, a 1.0 dB signal of 176 ppm. The signal level continued to increase as the CO in the inlet diffused to the sensor and then leveled off as expected.

Figure 33:
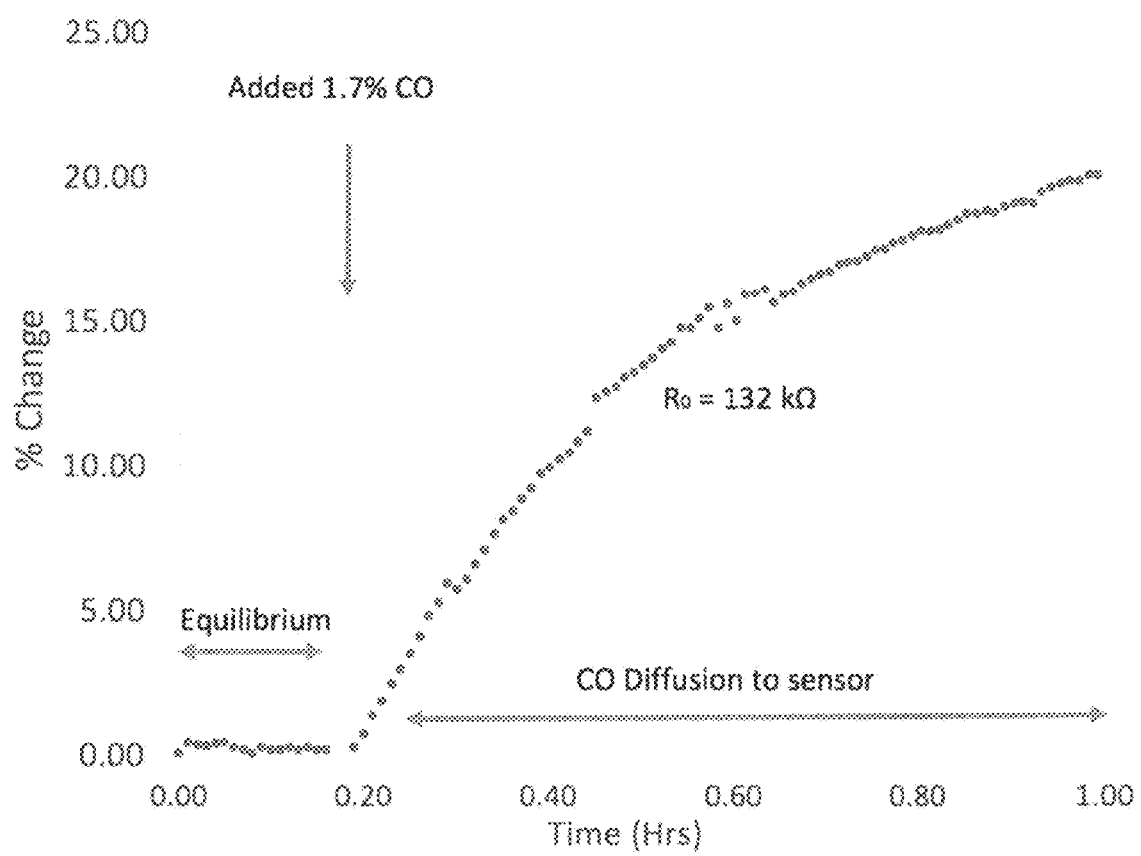
FIG. 33 is a graph depicting the results of Example 12, where a $CNT/SNO_2$/palladium device was exposed to CO (200 Hz)
Figure 34:
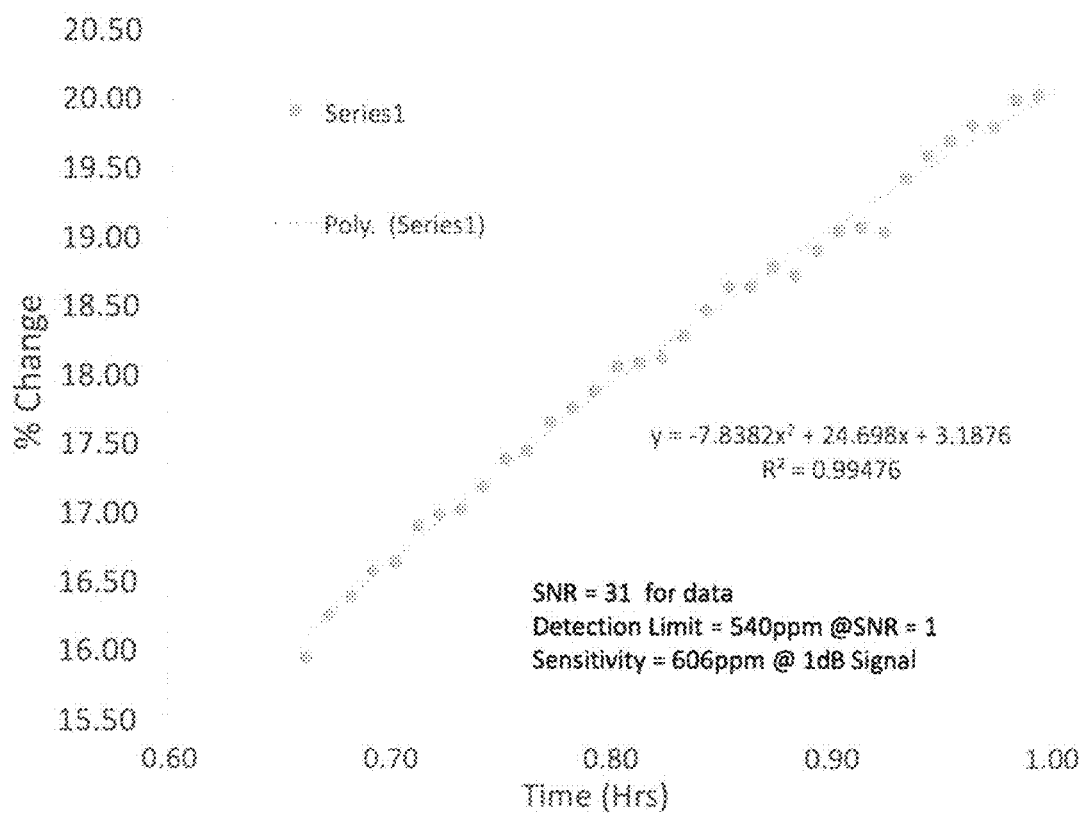
FIG. 34 is a graph of the signal-to-noise ratio analysis carried out in Example 12 to demonstrate the sensitivity of the device to CO gas concentration (200 Hz)

The experiment was repeated again with a lower pulse repetition rate, and consequently, a lower temperature. A repetition rate of 200 Hz was used, resulting in a temperature of about 70° C. In the lower-temperature run, the same amount of CO gas was introduced into the sample chamber. FIGS. 33 and 34 show the response at the lower pulse rate. A lower CO sensitivity (for a 1.0 dB signal) was observed at this lower temperature, at 540 ppm. This lower sensitivity was a direct result of the difference in the CO absorption curves as a function of temperature. The change in sensitivity divided by the change in temperature for the two temperatures is unique to the CO gas thermal absorption spectra in the pixel enhanced layer.

Example 13

Testing of 4-Pixel Gas Sensor with Methane

In this example, the pulse-heated sensitivity to methane of the CNT/$SNO_2$/palladium device fabricated in Example 7 was measured. The performance of this device was determined in the same way as described in Example 10 to measure the change in resistance of the active sensing layer 18 before, during, and after the pulse train, but with variable electronic current pulse train parameters of a pulse width of 70 µs, a repetition rate of 400 Hz, and a constant peak pulse voltage of 100 V.

This electronic pulse train heated the active sensing layer 18 within the pixel for a period of 4.4 seconds. The pixel was then allowed to cool for 30 seconds, and the pulse train was again used to heat the pixel for 4.4 seconds. This pattern was repeated throughout the experiment. In this example, the pulse repetition rate was set to 400 Hz as a result of a smaller 3 kΩ pixel impedance. The temperature was approximately 122° C.

Figure 35:
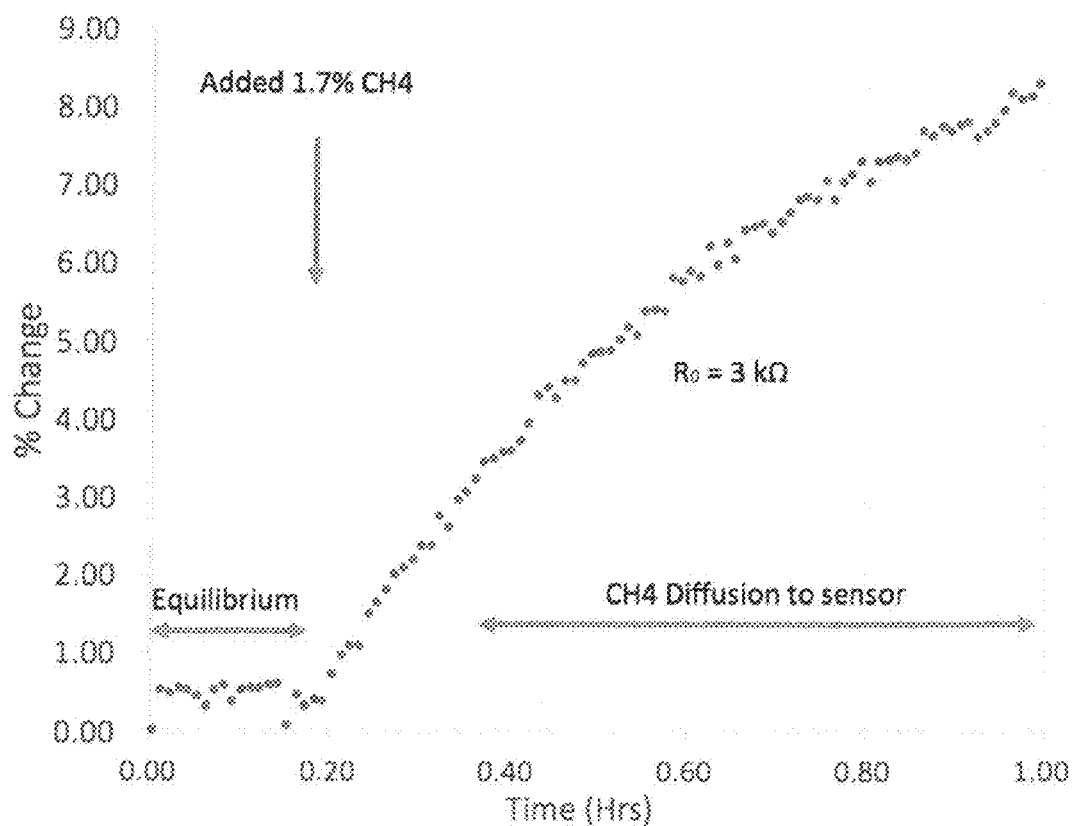
FIG. 35 is a graph depicting the results of Example 13, where a $CNT/SNO_2$/palladium device was exposed to $CH_4$ (400 Hz)
Figure 36:
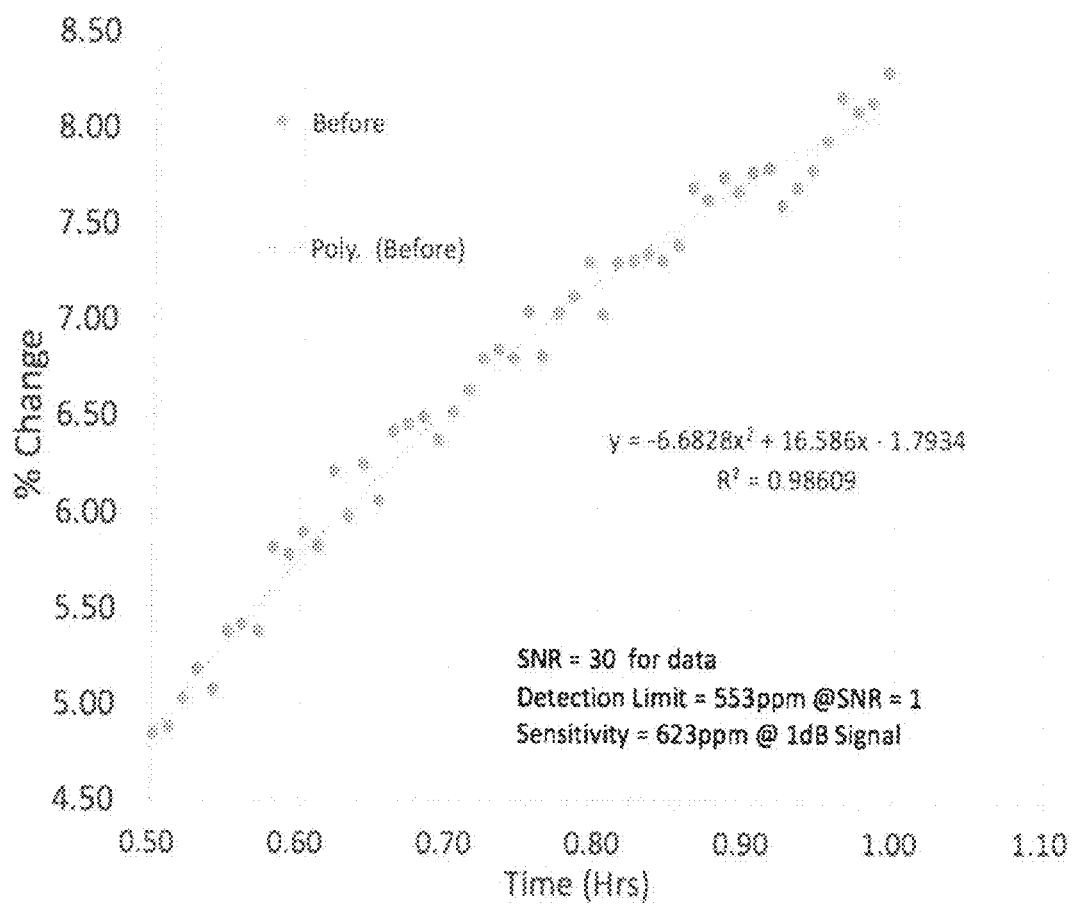
FIG. 36 is a graph of the signal-to-noise ratio analysis carried out in Example 13 to demonstrate the sensitivity of the device to $CH_4$ gas concentration (400 Hz)

The results of this experiment are shown in FIGS. 35 and 36. At an elapsed time of 11:30 minutes, a signal of 1.7% $CH_4$ was introduced into the Sample Chamber. The sensor device responded with a detection limit of 553 ppm, and, a 1.0 dB signal of 623 ppm. The signal level continued to increase as the $CH_4$ in the inlet diffused to the sensor and then leveled off as expected.

Figure 37:
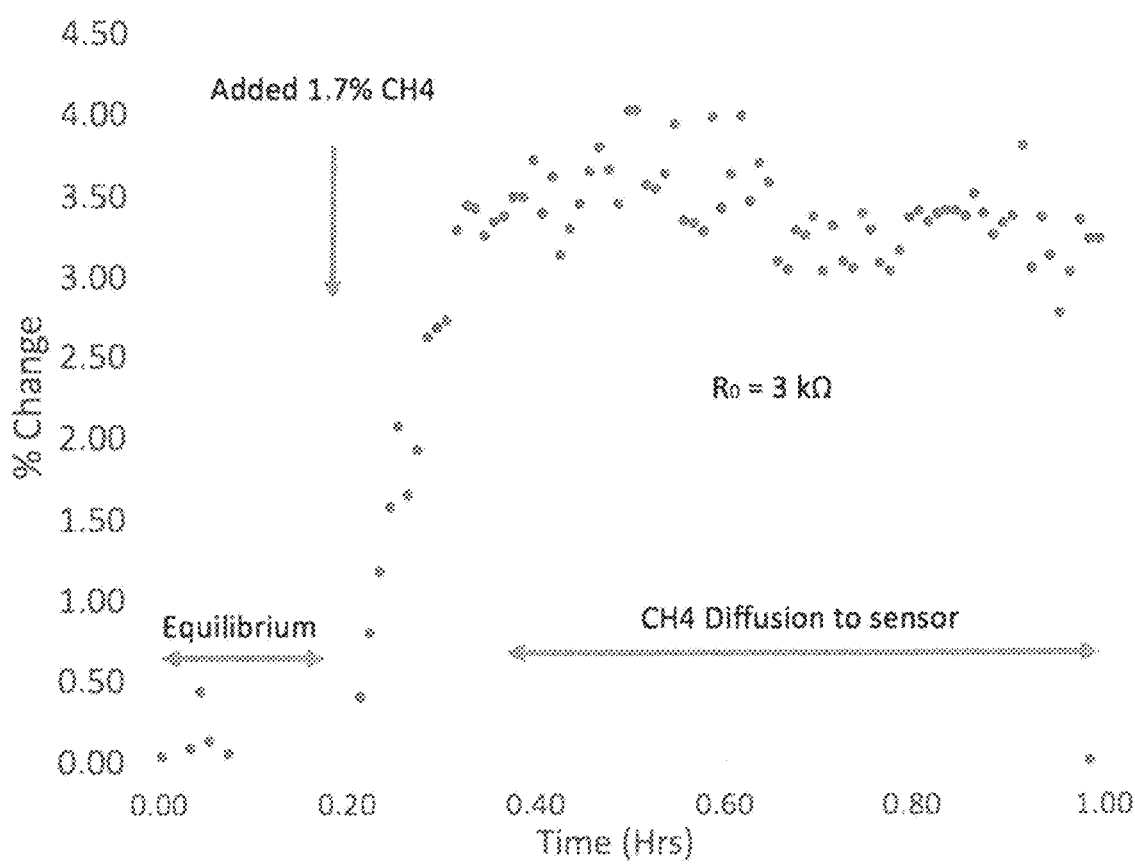
FIG. 37 is a graph depicting the results of Example 13, where a $CNT/SNO_2$/palladium device was exposed to $CH_4$ (200 Hz)
Figure 38:
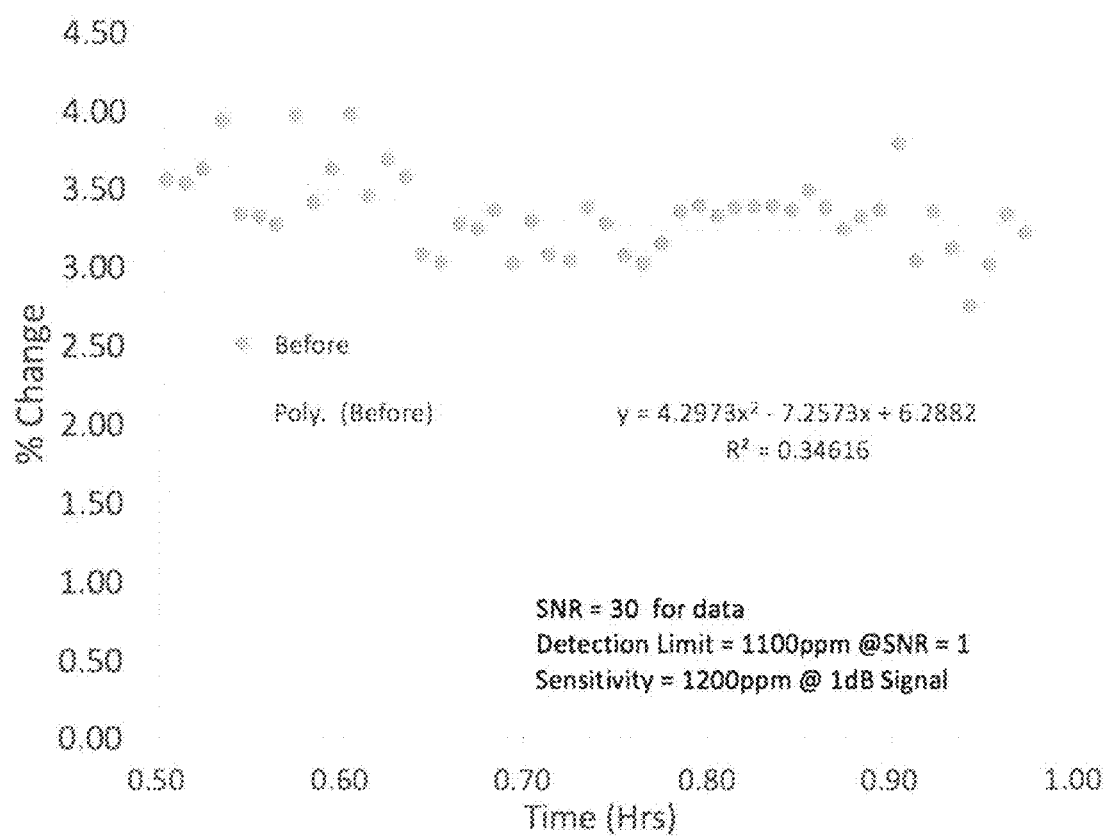
FIG. 38 is a graph of the signal-to-noise ratio analysis carried out in Example 13 to demonstrate the sensitivity of the device to $CH_4$ gas concentration (200 Hz)

The experiment was repeated again with a lower pulse repetition rate, and consequently, a lower temperature. A repetition rate of 200 Hz was used, resulting in a temperature of about 70° C. As in the lower-temperature run, the same (1.7%) of $CH_4$ gas was introduced into the sample chamber. FIGS. 37 and 38 show the response at the lower temperature. A lower $CH_4$ sensitivity (for a 1.0 dB signal) was observed at this lower temperature, at 1100 ppm. This lower sensitivity was a direct result of the difference in the $CH_4$ absorption curves as a function of temperature.

Example 14

Testing of Gas Sensor with Water

Figure 39:
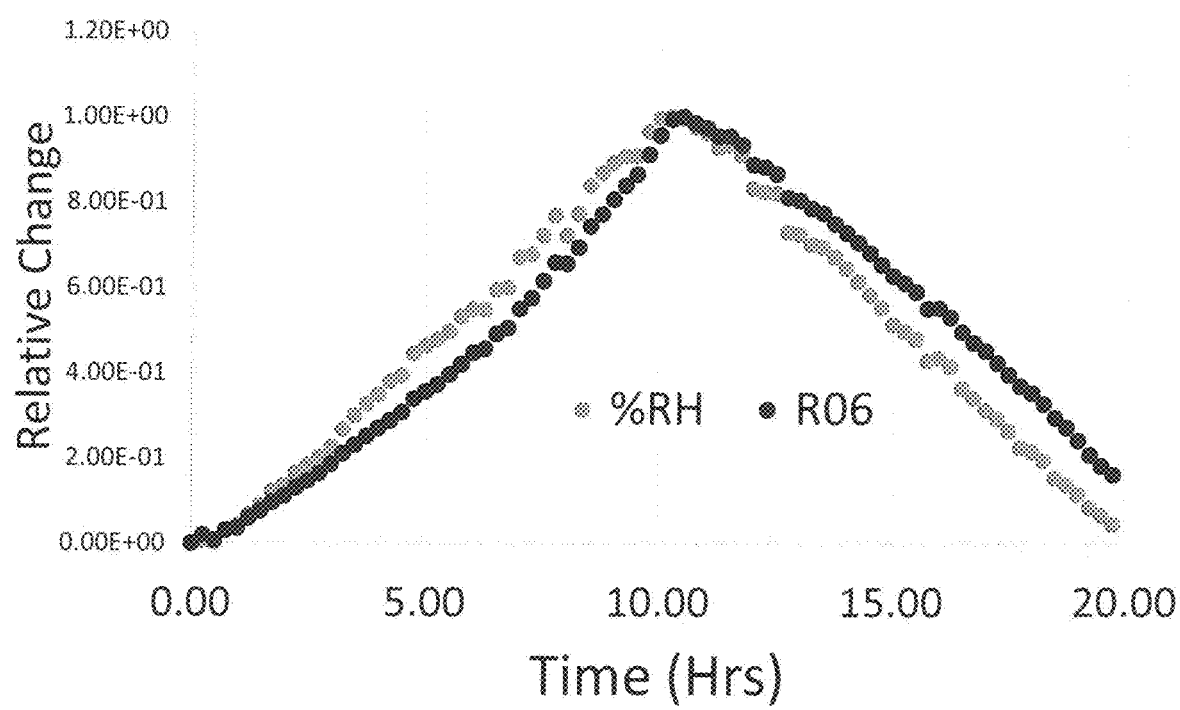
FIG. 39 is a graph showing the response to water vapor of the gas sensor of Example 14.

FIG. 39 shows the relative change of the response of the sensor tracked with the change in relative humidity in the environmental chamber at 200 Hz and otherwise the same pulse parameters as the 400 Hz case shown above. Specifically, a pulse width of 70 μs, a repetition rate of 400 Hz, and a constant peak pulse voltage of 100 V was used. The electronic pulse train was used to heat the active sensing layer 18 in the pixel for a period of 4.4 seconds, and then the resistance was measured. After an additional 15 minutes where the pixel was allowed to cool and collect moisture, the pulse train was again used to heat the pixel for 4.4 seconds and this pattern was repeated throughout the experiment. The relative humidity was ramped from 20% to 80% and back down again. The resistance change at this peak is about 16%. Therefore, the $H_2O$ vapor absorption curve for a four-pixel gas sensor would have the end points of a change in resistance of 16% when the pixel in pulsed at a rate of 200 Hz, and 0% when pulsed at 400 Hz. This unique slope as a result of water vapor absorption can be distinguished from the gas absorption resistance changes, giving the device gas selectivity.

Example 15

Sensitivity and Selectivity Demonstration of Sensors

Two different mean pixel temperatures (70° C. and 122° C.) were selected to show the slopes of the change in resistance values at these temperatures are indicative of the different thermal gas spectra for the gases CO, $CH_4$, $H_2$, and $H_2O$. The slope between these points is indicative of the gas type.

The pixel temperatures for these two points were measured by a FLIR AX5 IR research camera as described in Example 9. A device as fabricated in Example 7 was sliced from the sheet and electrical connections were made to the electrodes using tin-coated crimp pins. The device was mounted and tested in the system described in Example 8 and tested using the gas mixing mode of operation. The procedure used to measure the response of a single-pixel or 4-pixel device was the same as in previous examples, but with variable electronic current pulse train parameters of a pulse width of 70 μs, a repetition rate of 200 Hz for 70° C. and 500 Hz for 122° C., and a constant peak pulse voltage of 100 V.

Figure 40:
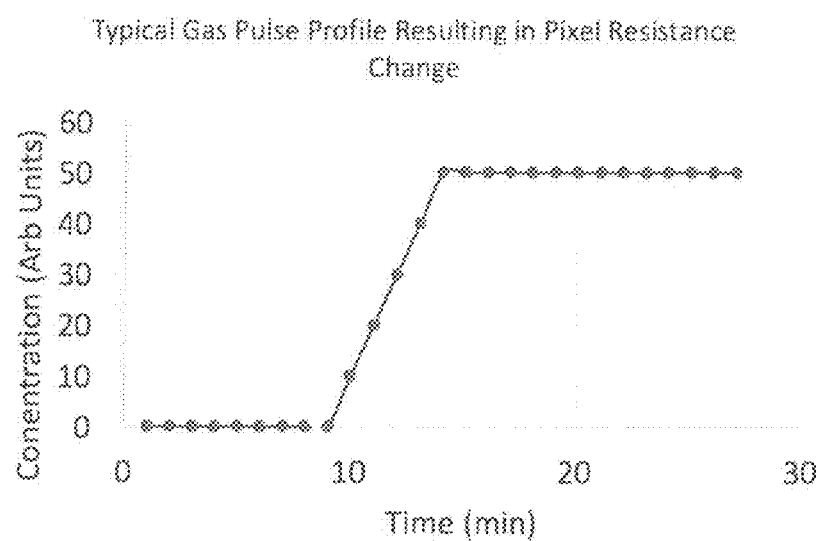
FIG. 40 is a graph depicting the generalized test gas concentration pulse as a function of time as described in Example 15.
Figure 41:
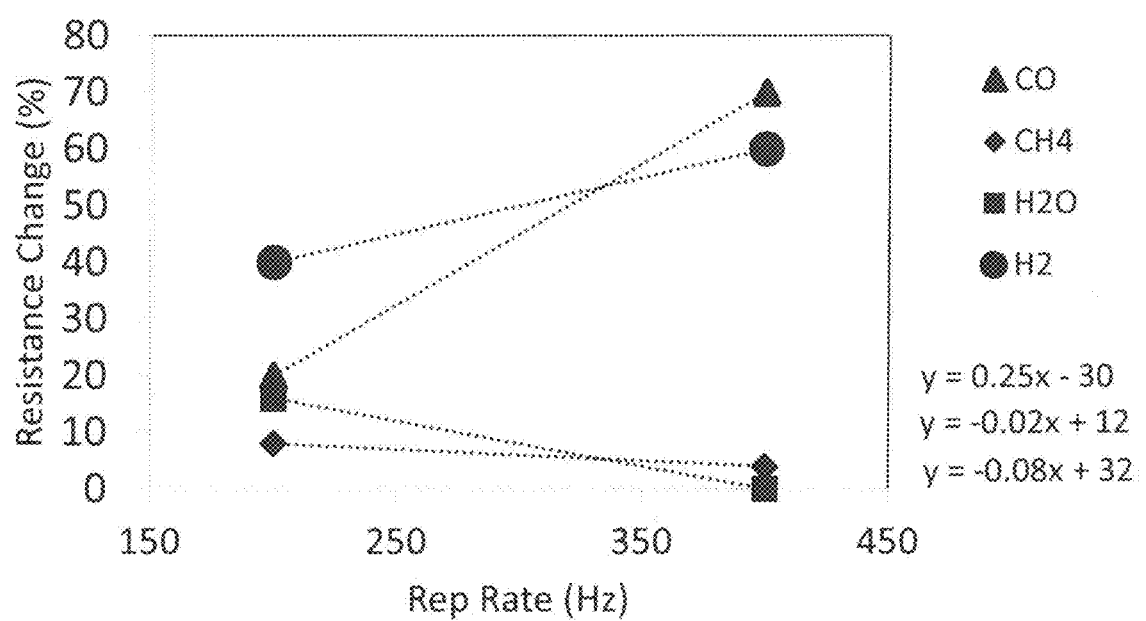
FIG. 41 is a graph showing varying slopes of resistance change for varying gases as described in Example 15.

The gases CO, $H_2$, $H_2O$, and $CH_4$ were introduced to the device environment as a function of time in a stepwise fashion as shown in FIG. 40. The results for the resistance measurements just after the pulse train are shown in FIG. 41. For a linear interpolation between the temperature measurements, the slope of the line connecting the two measurements is indicative of the gas type.

As shown in FIG. 41, there is no water signal at a pixel temperature of 122° C. since the sensor is dry at temperatures above 100° C.

Example 16

Determination of Speed and Hysteresis

Figure 42:
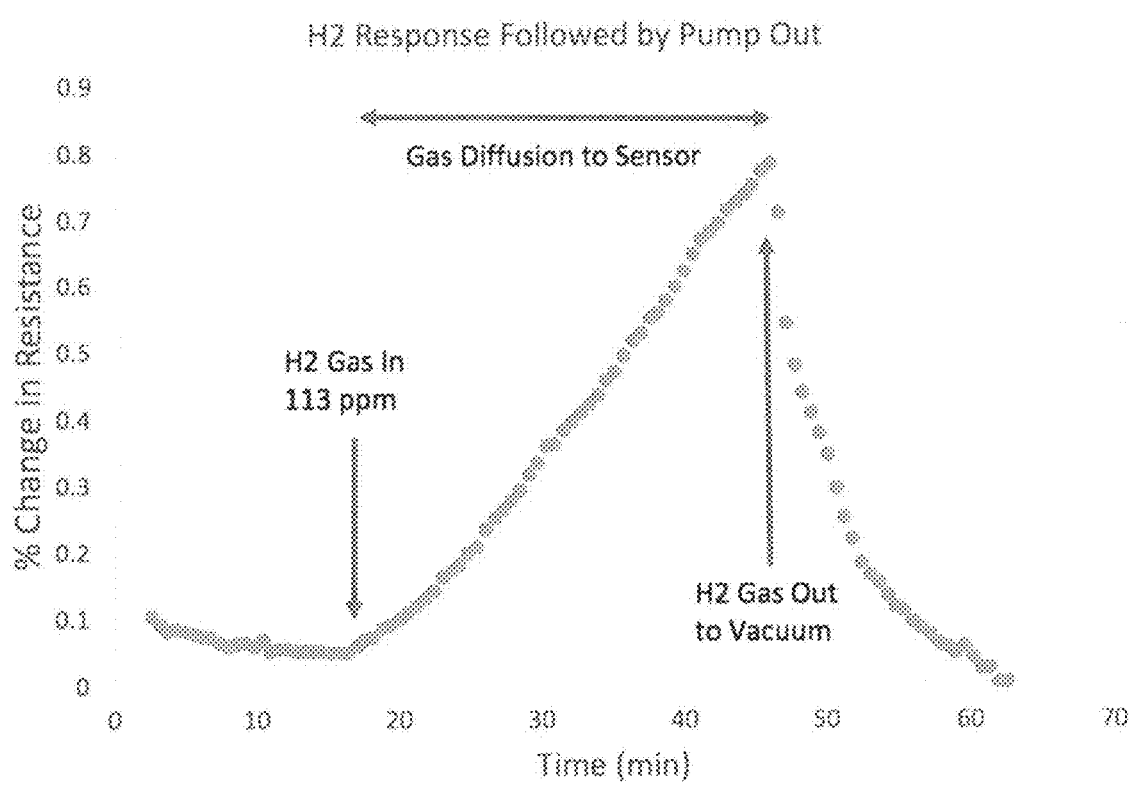
FIG. 42 is a graph of the resistance change in the device of Example 16 as a function of time with ramped hydrogen concentration.

A device as fabricated in Example 6 was first exposed to 113 ppm hydrogen in air and then the sample chamber was pumped to a vacuum. As shown in FIG. 42, the device first responded to the hydrogen in a very similar manner to those shown in FIG. 30, then after the hydrogen was removed, the signal returned to the original baseline before the $H_2$ was introduced. The faster response of the lowering of the hydrogen concentration is due to the fast vacuum pump throughput of the system compared to the slower diffusion of the gas from the inlet to the sample. This data indicates the speed of the device is faster than the diffusion time from the gas inlet to the sample.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:
1. An environmental sensor comprising:
 first and second electrodes formed from electrically conductive material, the electrodes spaced apart from one another and positioned on a substrate,
 the first and second electrodes configured to receive a sequence of electric voltage pulses from a high voltage source of about 25 V to about 500 V and a pulse modulator,
 the electric voltage pulses having a duration of less than about 100 microseconds;
 wherein the pulse modulator fixes a time between the pulses within a pulse train and the duration of the pulses; and
 an active sensing layer, the active sensing layer positioned on the substrate and in direct contact with a top surface and left and right side surfaces of each electrode, the active sensing layer configured to experience a change in an electrical characteristic in response to a change in a characteristic of a constituent gas in proximity to the active sensing layer and further configured to receive energy directly from the electric voltage pulses from the electrodes to set a temperature of the active sensing layer to a specific value.

2. The environmental sensor of claim 1, wherein the electrical characteristic is an electrical resistance.

3. The environmental sensor of claim 1, further comprising a signal enhancement layer positioned in contact with a top surface of the active sensing layer and configured to react with the constituent gas when contacted by the constituent gas and enhance the change in the electrical characteristic of the active sensing layer.

4. The environmental sensor of claim 3, wherein the signal enhancement layer is formed from a material selected from the group consisting of selective gas-absorbing materials, selective gas-adsorbing materials, and mixtures thereof.

5. The environmental sensor of claim 4, wherein the signal enhancement layer includes metal oxides.

6. The environmental sensor of claim 1, further comprising a filter layer positioned in contact with a top surface of the active sensing layer and configured to isolate the active sensing layer from selected environmental stimuli.

7. The environmental sensor of claim 1, wherein the active sensing layer comprises carbon nanotubes.

8. The environmental sensor of claim 1, wherein the active sensing layer is configured to receive thermal energy.

9. An environmental sensor array comprising:
   a plurality of pixel sensors, each pixel sensor including first and second electrodes formed from electrically conductive material, the electrodes spaced apart from one another and positioned on a substrate,
   the first and second electrodes configured to receive a sequence of electric voltage pulses from a high voltage source of about 25 V to about 500 V and a pulse modulator,
   the electric voltage pulses having a duration of less than about 100 microseconds;
   wherein the pulse modulator fixes a time between the pulses within a pulse train and the duration of the pulses; and
   an active sensing layer, the active sensing layer positioned on the substrate and in direct contact with a top surface and left and right side surfaces of each electrode,
   the active sensing layer configured to experience a change in an electrical characteristic in response to a change in a characteristic of a constituent gas in proximity to the active sensing layer and further configured to receive energy directly from the electric voltage pulses from the electrodes to set a temperature of the active sensing layer to a specific value.

10. The environmental sensor array of claim 9, wherein the active sensing layer of each pixel sensor is individually formed from:
    a. a single, uniform composition; or
    b. a mixture of compositions.

11. The environmental sensor array of claim 10, wherein the active sensing layer of at least one pixel sensor is formed from a single, uniform composition and the active sensing layer of at least one pixel sensor is formed from a mixture of compositions.

12. The environmental sensor array of claim 10, wherein at least one pixel sensor comprises a signal enhancement layer positioned in contact with a top surface of the active sensing layer and configured to react with the constituent gas when contacted by the constituent gas and enhance the change in the electrical characteristic of the active sensing layer.

13. The environmental sensor array of claim 12, wherein the signal enhancement layer comprises metal oxides.

14. The environmental sensor array of claim 10, wherein the mixture of compositions comprises a signal enhancement material.

15. The environmental sensor array of claim 14, wherein the signal enhancement material includes metal oxides.

16. The environmental sensor array of claim 10, wherein the active sensing layer of each pixel sensor is individually formed from:
    a. carbon nanotubes; or
    b. carbon nanotubes mixed with a signal enhancement material responsive to a specific constituent gas, the mixture of the carbon nanotubes and the signal enhancement material forming a single layer.

17. The environmental sensor array of claim 16, wherein the active sensing layer of at least one pixel sensor is formed from carbon nanotubes and the active sensing layer of at least one pixel sensor is formed from carbon nanotubes mixed with a signal enhancement material.

18. The environmental sensor array of claim 9, wherein the electrical characteristic is an electrical resistance.

19. A method of determining a constituent gas with an environmental sensor, the method comprising:
    a. generating a train of electrical pulses that is received by the first and second electrodes of the environmental sensor of claim 1, the train of electrical pulses configured to set a temperature of the environmental sensor;
    b. measuring a first electrical resistance between the first and second electrodes of the environmental sensor during the generation of the train of electrical pulses;
    c. repeating a. and b. a plurality of times such that each train of electrical pulses sets the environmental sensor to a different temperature resulting in a first spectrum including a plurality of first resistance measurements, one first resistance measurement for each temperature; and
    d. comparing the first spectrum to a plurality of response spectra, each response spectrum corresponding to a thermal spectral response of a successive one of a plurality of constituent gases.

20. The method of claim 19, further comprising determining which response spectrum most closely matches the first spectrum.

21. The method of claim 19, wherein each response spectrum corresponds to a thermal spectral response of a plurality of constituent gases in combination and the method further comprises determining which response spectrum most closely matches the first spectrum.

22. The method of claim 19, further comprising determining a combination response spectrum for each of a plurality of combinations of constituent gases and determining which combination response spectrum most closely matches the first spectrum.

23. The method of claim 19, wherein each electrical pulse is a pulse of electrical voltage.

24. The method of claim 19, wherein each electrical pulse is a pulse of electrical current.

25. The method of claim 19, wherein each train of electrical pulses is generated for a first time period and includes a plurality of electrical pulses, each electrical pulse having a pulse width time duration with the train of electrical pulses being generated at a repetition rate.

26. The method of claim 19, further comprising waiting for a second time period between generating successive trains of electrical pulses.

27. The method of claim 19, wherein each first electrical resistance measurement is an average value of a plurality of electrical resistance measurements made during one train of electrical pulses.

28. A method of determining a constituent gas with an environmental sensor array including a plurality of pixel sensors, the method comprising:
  a. generating a train of electrical pulses that is received by the first and second electrodes of each pixel sensor of the environmental sensor array of claim 9, the train of electrical pulses configured to set a different temperature for each pixel sensor;
  b. measuring a plurality of electrical resistances, each electrical resistance measured between the first and second electrodes of successive pixel sensors during the generation of the train of electrical pulses, resulting in a spectrum including one electrical resistance measurement for each temperature; and
  c. comparing the spectrum to a plurality of response spectra, each response spectrum corresponding to a thermal spectral response of a successive one of a plurality of constituent gases.

29. The method of claim 28, further comprising determining which response spectrum most closely matches the spectrum.

30. The method of claim 28, wherein each response spectrum corresponds to a thermal spectral response of a plurality of constituent gases in combination and the method further comprises determining which response spectrum most closely matches the spectrum.

31. The method of claim 28, further comprising determining a combination response spectrum for each of a plurality of combinations of constituent gases and determining which combination response spectrum most closely matches the spectrum.

32. The method of claim 28, wherein each electrical pulse is a pulse of electrical voltage.

33. The method of claim 28, wherein each electrical pulse is a pulse of electrical current.

34. The method of claim 28, wherein each train of electrical pulses is generated for a first time period and includes a plurality of electrical pulses, each electrical pulse having a pulse width time duration with the train of electrical pulses being generated at a repetition rate.

35. The method of claim 28, further comprising waiting for a second time period between generating successive trains of electrical pulses.

36. The method of claim 28, wherein each electrical resistance measurement is an average value of a plurality of electrical resistance measurements made during one train of electrical pulses.

37. A method of determining a constituent gas concentration with an environmental sensor, the method comprising:
  d. measuring a first electrical resistance between first and second electrodes of the environmental sensor of claim 1;
  e. generating a train of electrical pulses that is received by the first and second electrodes, the train of electrical pulses configured to set a temperature of the environmental sensor;
  f. measuring a second electrical resistance between the first and second electrodes after the generation of the train of electrical pulses;
  g. subtracting the second electrical resistance measurement from the first electrical resistance measurement; and
  h. determining a value of a constituent gas concentration in proximity to the environmental sensor corresponding to the difference between the first resistance measurement and the second resistance measurement.

38. The method of claim 37, wherein the constituent gas is a combination of two or more gases.

39. The method of claim 37, wherein the first electrical resistance measurement is an average value of two electrical resistance measurements, one electrical resistance measurement having a first polarity and the other electrical resistance measurement having a second, opposing polarity.

40. The method of claim 37, wherein the second electrical resistance measurement is an average value of two electrical resistance measurements, one electrical resistance measurement having a first polarity and the other electrical resistance measurement having a second, opposing polarity.

41. The method of claim 37, further comprising measuring a third electrical resistance during the train of electrical pulses and using the third electrical resistance to adjust one or more parameters of the train of electrical pulses in order to control the temperature of the environmental sensor.

42. The method of claim 37, wherein the train of electrical pulses is applied for a first time period and at a repetition rate, each electrical pulse having a pulse width time duration and a magnitude value, wherein the first and second electrodes transfer thermal energy to an active sensing layer of the environmental sensor which sets the temperature.

43. The method of claim 37, wherein each electrical pulse is a pulse of electrical voltage.

44. The method of claim 37, wherein each electrical pulse is a pulse of electrical current.

45. A method of heating an environmental sensor, the method comprising:
  applying a train of electrical pulses to the first and second electrodes of the environmental sensor of claim 1,
  the train of electrical pulses being applied for a first time period and at a repetition rate, each electrical pulse having a pulse width time duration and a magnitude value,
  wherein the first and second electrodes transfer thermal energy to the active sensing layer which sets the environmental sensor to a temperature.

46. The method of claim 45, wherein a combination of two or more of the first time period, the repetition rate, the pulse width time duration, and the magnitude value determines the temperature of the environmental sensor.

47. The method of claim 45, wherein the combination is chosen to set the temperature of the environmental sensor to evaporate or decompose a constituent gas diffused in the active sensing layer.

48. The method of claim 45, further comprising measuring an electrical resistance during the train of electrical pulses and using the electrical resistance to adjust one or more of the first time period, the repetition rate, the pulse width time duration, and the magnitude value in order to control the temperature of the environmental sensor.

49. The method of claim 45, wherein each electrical pulse is an electrical voltage pulse applied across the first and second electrodes, the electrical pulse having an electrical voltage magnitude value.

50. The method of claim 45, wherein each electrical pulse is an electrical current pulse injected in either the first electrode or the second electrode, the electrical pulse having an electrical current magnitude value.

51. An environmental sensor comprising:
  first and second electrodes formed from electrically conductive material, the electrodes spaced apart from one another and positioned on a substrate, the first and second electrodes configured to receive a sequence of electric voltage pulses from a high voltage source of about 25 V to about 500 V and a pulse modulator, the electric voltage pulses having a duration of less than about 100 microseconds;

an active sensing layer, the active sensing layer positioned on the substrate and in direct contact with a top surface and left and right side surfaces of each electrode, the active sensing layer configured to experience a change in an electrical characteristic in response to a change in a characteristic of a constituent gas in proximity to the active sensing layer and further configured to receive energy directly from the electric voltage pulses from the electrodes to set a temperature of the active sensing layer to a specific value;

a first signal enhancement layer positioned in contact with a top surface and left and right side surfaces of the active sensing layer and configured to enhance the change in the electrical characteristic of the active sensing layer; and a first filter layer positioned in contact with a top surface of the first signal enhancement layer and configured to contact the constituent gas and isolate the active sensing layer from selected environmental stimuli.

52. The environmental sensor of claim 51, further comprising:

a second signal enhancement layer positioned in contact with a bottom surface of the active sensing layer and configured to enhance the change in the electrical characteristic of the active sensing layer; and a second filter layer positioned in contact with a bottom surface of the second signal enhancement layer and configured to isolate the active sensing layer from selected environmental stimuli.

* * * * *